(12) United States Patent
Lexow

(10) Patent No.: US 6,723,513 B2
(45) Date of Patent: Apr. 20, 2004

(54) SEQUENCING METHOD USING MAGNIFYING TAGS

(75) Inventor: Preben Lexow, Bergen (NO)

(73) Assignee: Lingvitae AS, Oslo (NO)

( * ) Notice: Subject to any disclaimer, the term of this patent is extended or adjusted under 35 U.S.C. 154(b) by 0 days.

(21) Appl. No.: 09/886,223

(22) Filed: Jun. 22, 2001

(65) Prior Publication Data

US 2002/0028458 A1 Mar. 7, 2002

Related U.S. Application Data

(63) Continuation of application No. PCT/GB99/04417, filed on Dec. 23, 1999.

(30) Foreign Application Priority Data

| | | |
|---|---|---|
| Dec. 23, 1998 | (NO) | 986133 |
| Feb. 26, 1999 | (NO) | 996330 |
| Mar. 19, 1999 | (NO) | 996331 |
| Apr. 13, 1999 | (NO) | 996332 |
| Apr. 14, 1999 | (NO) | 996333 |
| Apr. 16, 1999 | (NO) | 996334 |
| Apr. 19, 1999 | (NO) | 996335 |
| Jun. 11, 1999 | (NO) | 996336 |
| Jun. 15, 1999 | (NO) | 996337 |
| Aug. 26, 1999 | (NO) | 996338 |
| Sep. 10, 1999 | (NO) | 996339 |

(51) Int. Cl.$^7$ .......................... C12Q 1/68; C07H 21/02; C07H 21/04
(52) U.S. Cl. ........................ 435/6; 536/23.1; 536/24.3
(58) Field of Search ............................ 435/6; 536/23.1, 536/24.3

(56) References Cited

U.S. PATENT DOCUMENTS

| | | | |
|---|---|---|---|
| 5,552,278 A | * | 9/1996 | Brenner |
| 5,888,737 A | * | 3/1999 | DuBridge et al. |
| 6,150,516 A | * | 11/2000 | Brenner et al. |

* cited by examiner

*Primary Examiner*—Ethan Whisenant
(74) *Attorney, Agent, or Firm*—Sughrue Mion, PLLC

(57) ABSTRACT

The present invention provides a method of sequencing all or part of a target nucleic acid molecule by determining the sequence of a portion of said nucleic acid molecule in addition to information regarding the position of said portion and in particular provides a new method of sequencing involving the magnification of one or more bases of said bases to aid identification.

24 Claims, 36 Drawing Sheets

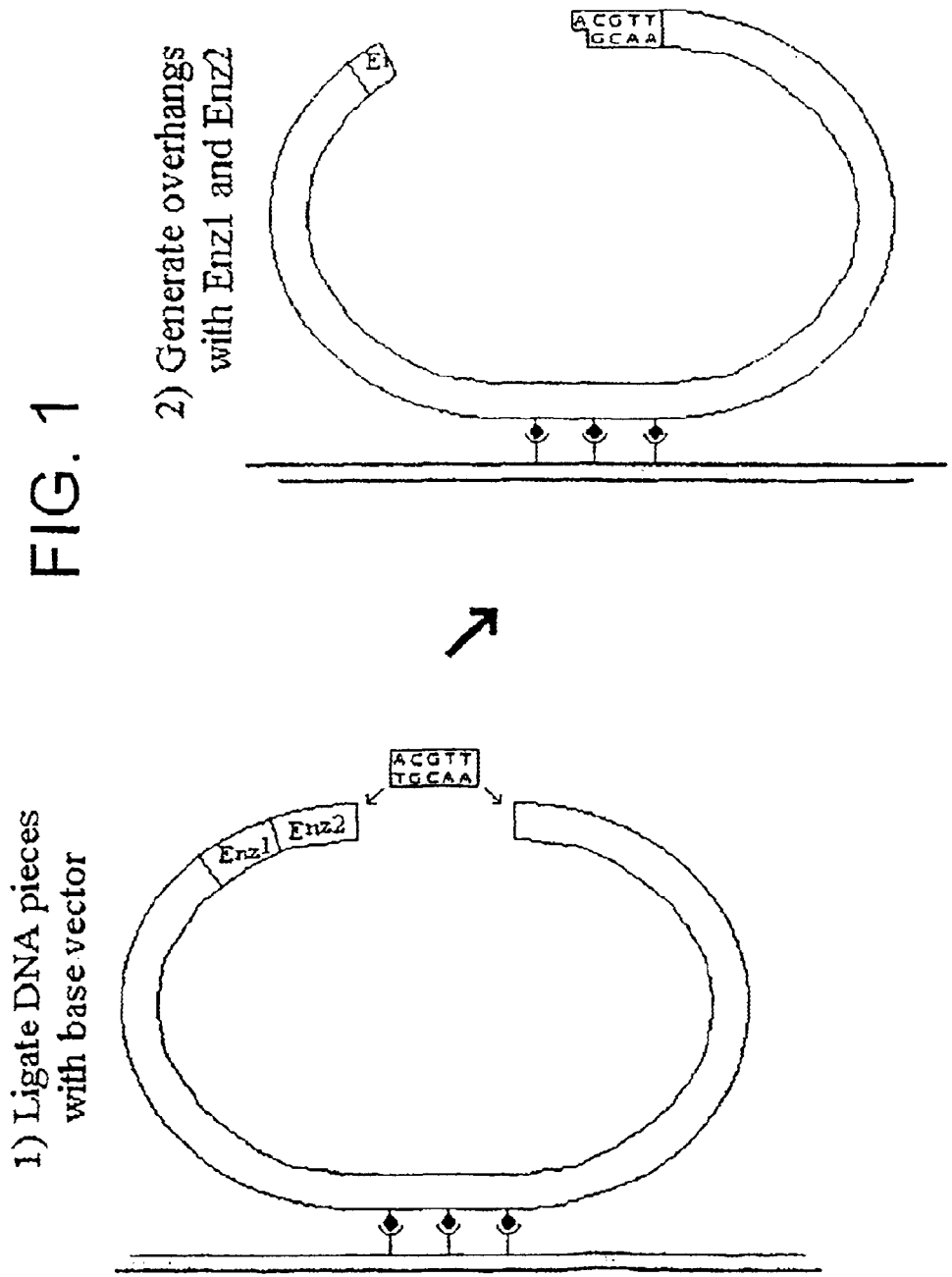

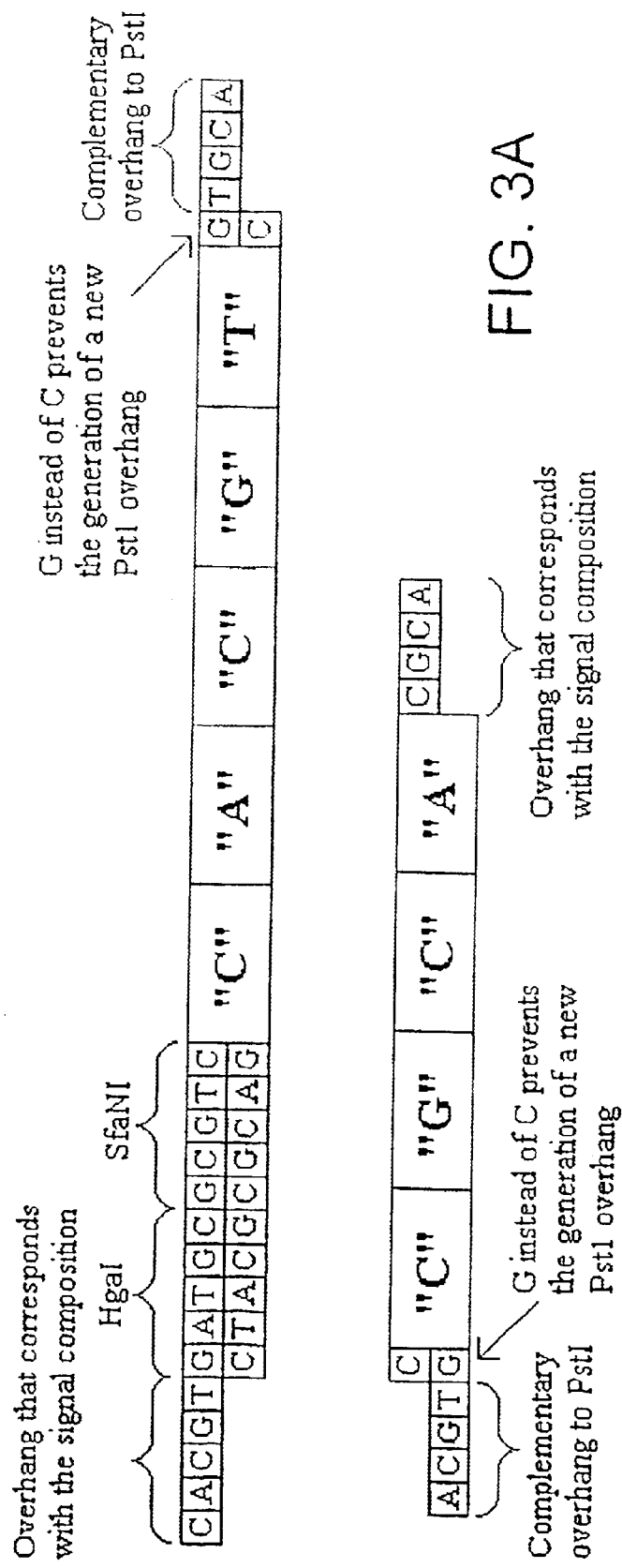

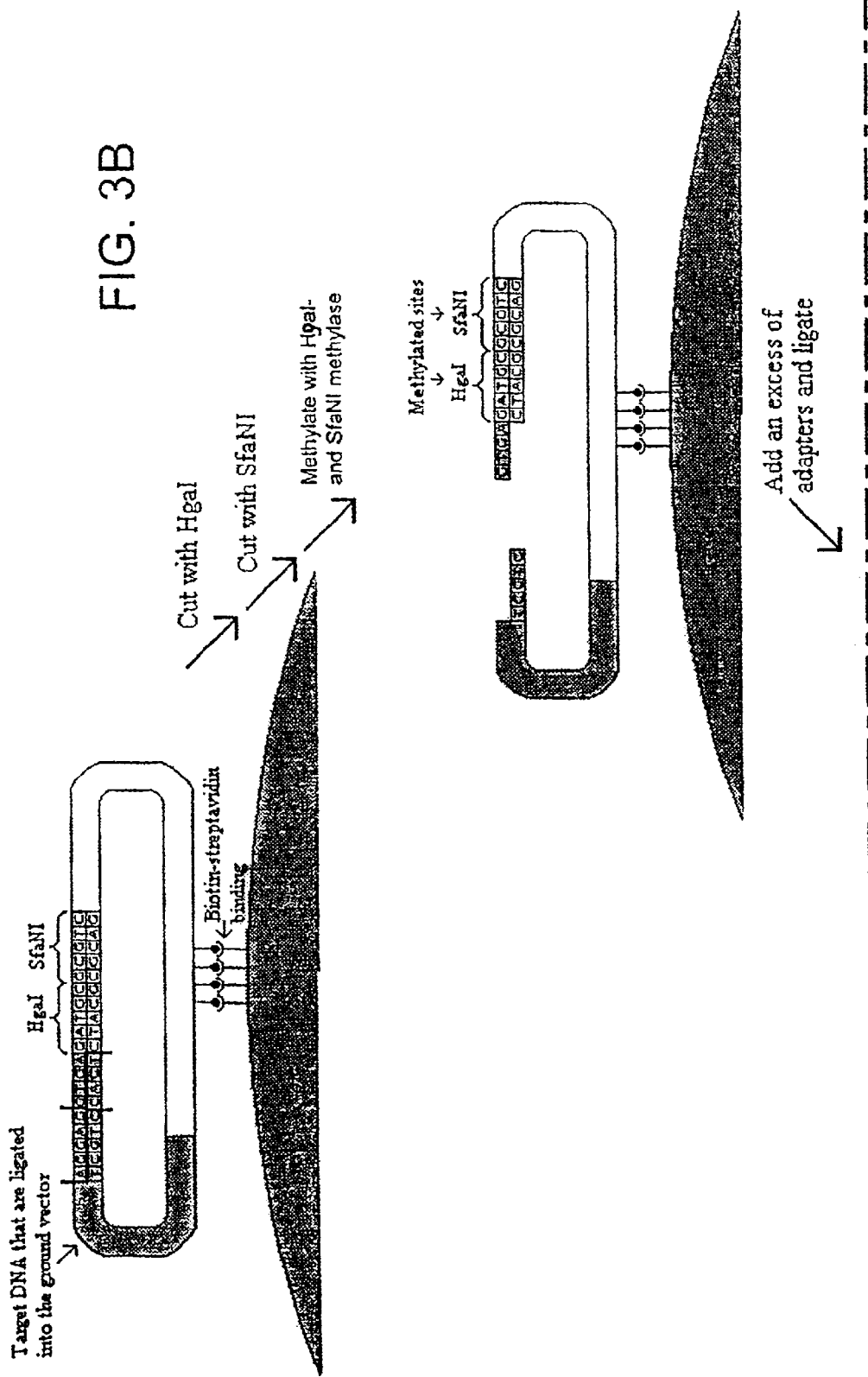

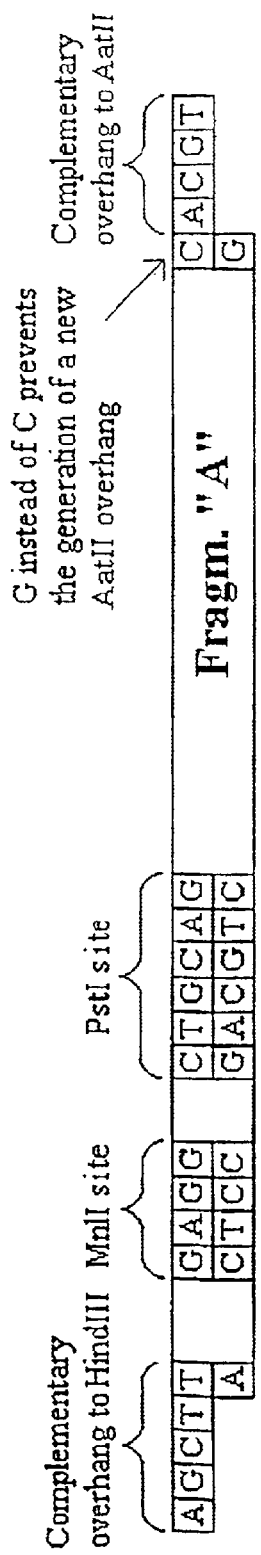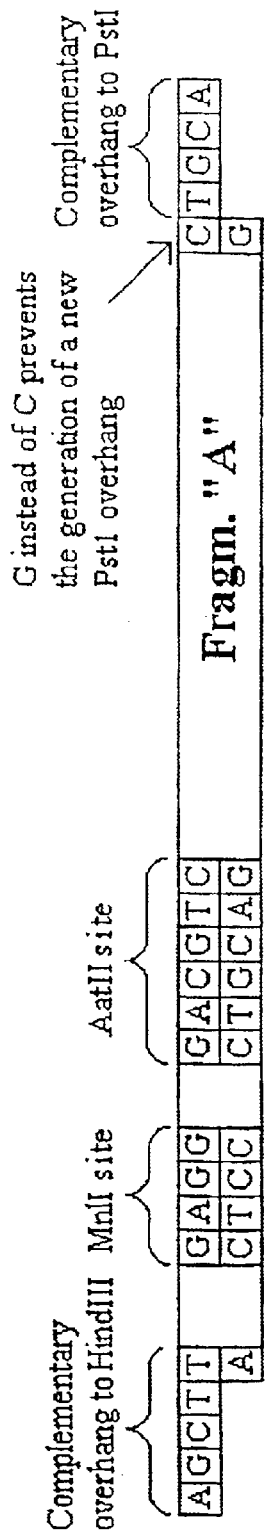
FIG. 4A
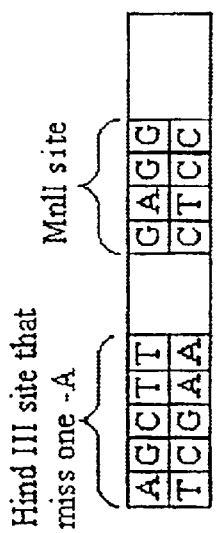
FIG. 4B

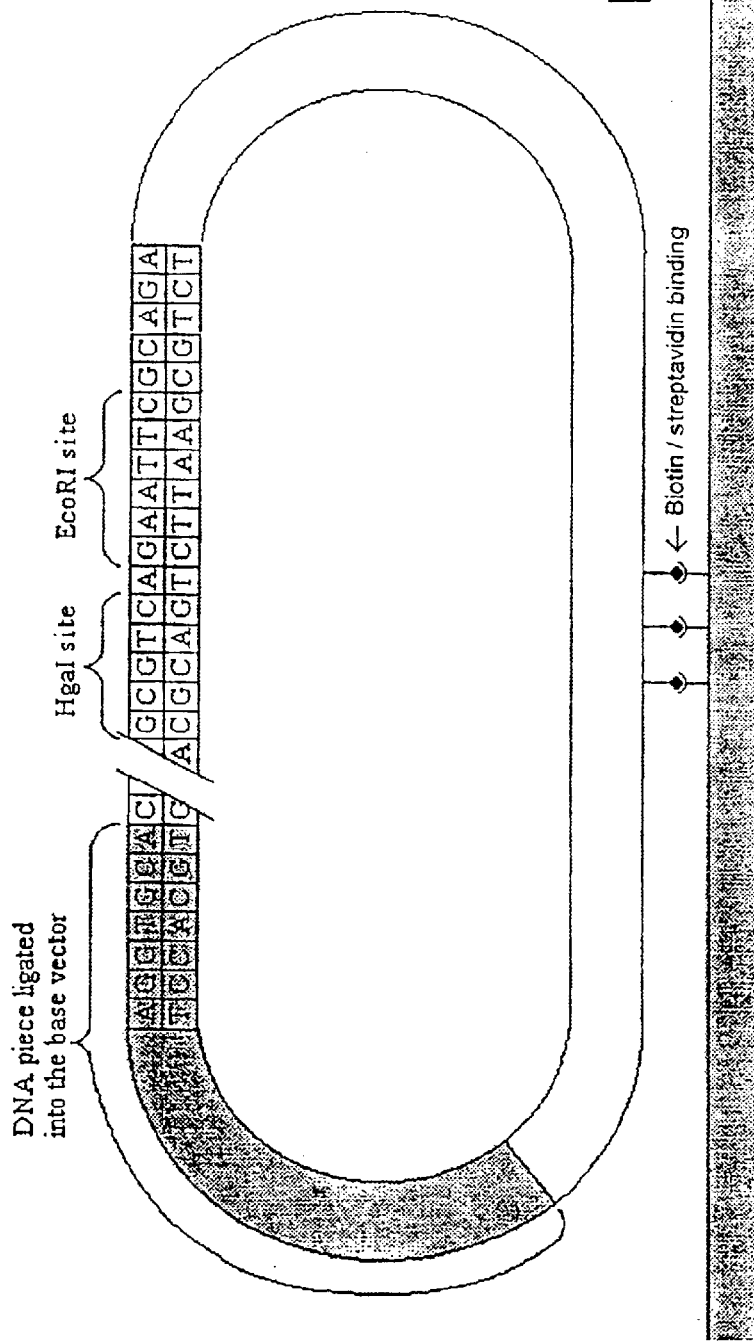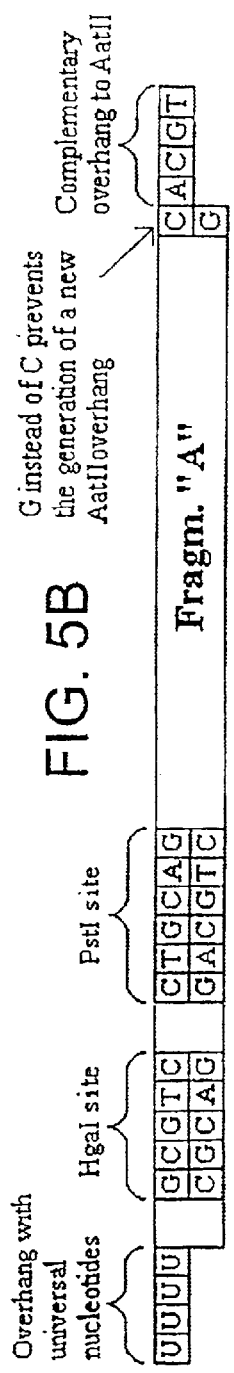
FIG. 5A
FIG. 5B

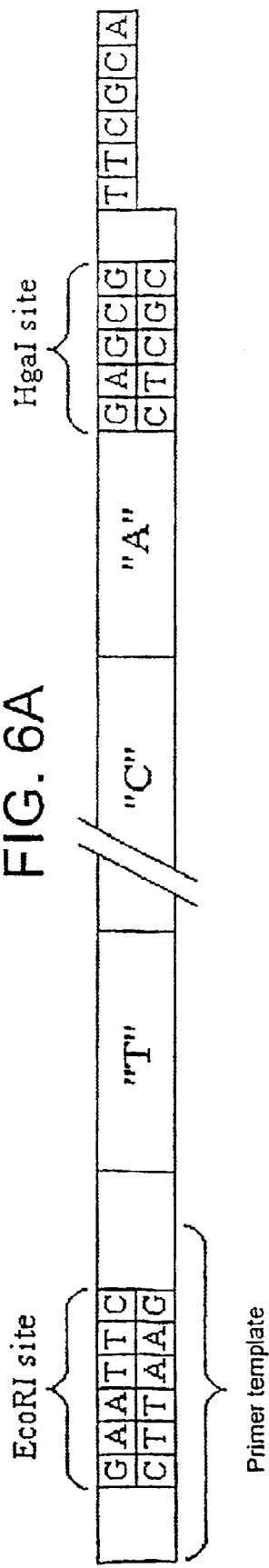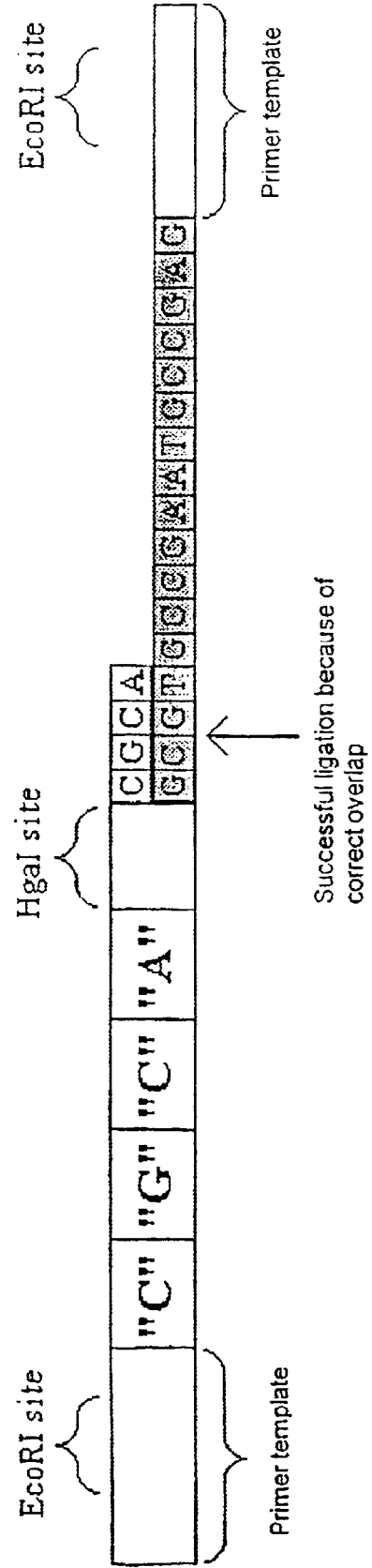
FIG. 6A
FIG. 6B

FIG. 16B
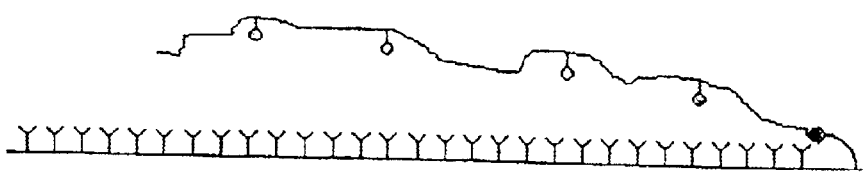
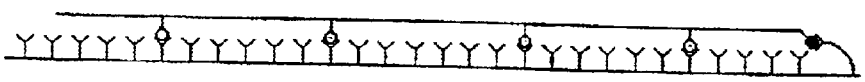
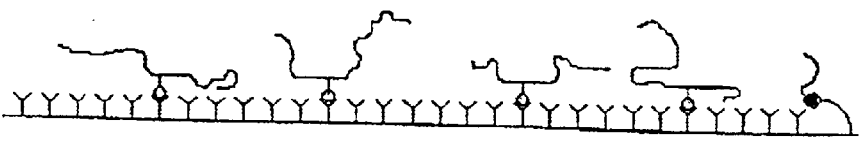
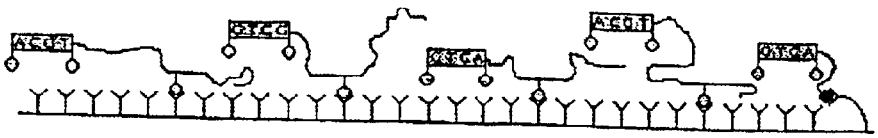
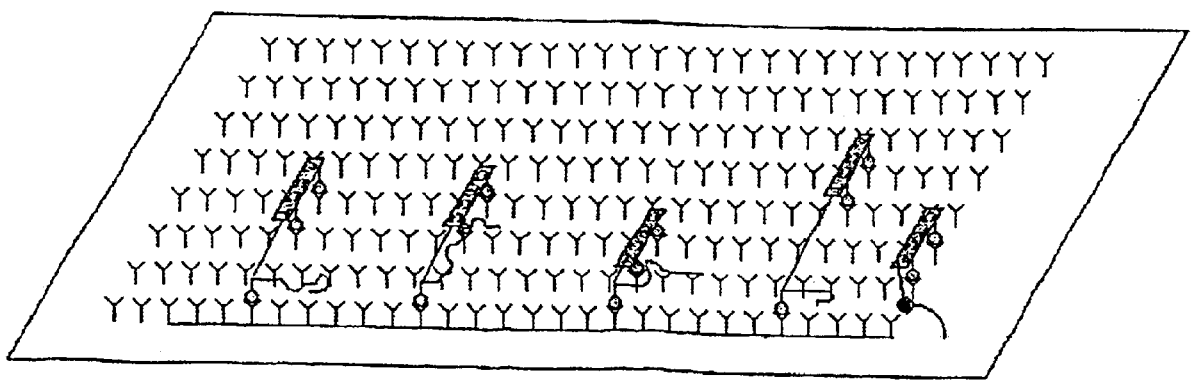
FIG. 18

SEQUENCING METHOD USING MAGNIFYING TAGS

This Application is a Continuation of PCT/GB99/04417 (published under PCT Article 21(2) in English) filed Dec. 23, 1999. The disclosure of PCT/GB99/04417 is incorporated herein by reference.

The present invention relates to new methods of sequencing in which the information embodied by each base is effectively magnified, and methods which are particularly suitable for sequencing long nucleic acid molecules in which sequence information for portions of the sequence and details on the portions, positions within the sequence is combined, and kits for performing such methods.

Ever since Watson and Crick clarified the structure of the DNA molecule in 1953, genetic researchers have wanted to find fast and cheap ways of sequencing individual DNA molecules. Sanger/Barrell and Maxam/Gilbert developed two new methods for DNA sequencing between 1975 and 1977 which represented a major breakthrough in sequencing technology. All methods in extensive use today are based on the Sanger/Barrell method and developments in DNA sequencing in the last 23 years have more or less been modifications of this method.

In 1988, however, DNA sequencing technology acquired an entirely new focus. Led by the US, eighteen countries joined together in perhaps the largest individual project in the history of science, the sequencing of the entire human genome of $3 \times 10^9$ bp (the Human Genome Project, also called HGP), in addition to several other smaller genomes. As of today, the objective is to be finished during the year 2003. In spite of the fact that the project ties up large scientific resources and carries a large price tag, the gains of the project are considered sufficiently important to justify the cost.

An important part of the project is to develop new methods of DNA sequencing that are both reasonably priced and faster than current technology in principle, these can be divided into gel based (primarily new variants of the Sanger/Parrell method) and non gel-based techniques. The non gel-based techniques probably have a greater potential and mass spectrometry, flow cytometry, and the use of gene chips that hybridize small DNA molecules are some of the approaches that are being tested. Methods that are substantially better than current methods would result in a revolution not only for gene research but also for modern medicine since they would provide the opportunity for extensive patient gene testing and may play an important role in identification and development of drugs. The economic potential of such methods are naturally very great.

Using the currently known sequencing techniques, it has proved difficult to extend the length of the sequences that can be read for each sequencing reaction, and most methods used today are limited to about 7–800 base pairs per sequencing reaction. Nor is it possible to sequence more than one sequence per sequencing reaction with the methods widely used today.

To sequence many or long sequences, it is generally necessary to perform many parallel sequencing reactions (e.g. to sequence a diploid human genome of 6 billion base pairs, several million parallel sequencing reactions would be necessary). This is a considerable bottleneck because the total number of processes, the use of enzymes and reagents, the number of unique primers required, etc. are often directly proportional to the number of sequencing reactions that have to be performed. Furthermore, resources often have to be devoted to sequencing overlapping sequences. In addition, different types of organisation work must be performed, such as setting up and sorting a DNA library. It is also necessary to expend resources in order to isolate a possible target sequence if it is found among other sequences.

In order to illustrate the fundamental problems that limit the length of sequencing reactions, it is appropriate to divide the sequencing methods currently used and under development into two large groups (there are individual methods that fall outside this division, but they represent a small minority). In the first group, we have methods based on the size range of polynucleotides. The starting point is to make one or more polynucleotide ladders in which all molecules have one common and one arbitrary end. For example, the classical sequencing methods of Sanger and Maxam-Gilbert are based on four sequence ladders that represent each of the four bases A, C, G, and T.

The limiting factor with respect to the length of a sequencing reaction that can be read is that one must be able to distinguish between polynucleotides that only vary with one monomer. The longer the polynucleotides in the sequence ladder, the smaller the relative differences in size between the polynucleotides. Most of the methods for determining the size of molecules thus quickly reach a limit where it is not possible to distinguish between two adjacent polynucleotides.

In the other group the methods are based on a different principle. By identifying short pieces of sequences that are present in a target molecule, the target sequence can be reconstructed by utilising the overlaps between the sequence pieces.

Thus, in many sequencing methods target molecules are fragmented into smaller pieces, the composition of each fragment is deduced and by finding overlapping sequences the original sequence is constructed. For example, microarrays have been created with 65,536 addresses where each address contains unique octamers. All permutations with octamers ($4_8 = 65,536$) are thus covered. If the target molecules then are tagged with fluorescence and hybridised with the octamers, the information about what sequence pieces are present in the target sequence can be obtained by registering the addresses that have been labelled with fluorescence.

An important limiting factor with respect to the length of sequencing reactions that can be read is the following combinatorial problem. The longer the sequencing reaction that is to be performed, the longer the sequence pieces must be in order to make reconstruction of the target sequence possible. However, the number of permutations that have to be tested increases exponentially with the length of the sequence pieces that are to be identified. This increases the need for unique addresses on the microarrays in a corresponding manner.

An alternative use for microarrays is resequencing of known sequences, e.g. by screening for gene mutations in a population. For this purpose, oligonucleotides can be adjusted to the known sequence so that the number of addresses required can be reduced and the length of the sequence pieces that are identified can be increased. However, designing microarrays for specific purposes is expensive and resource demanding, and at present there are only microarrays for a few DNA sequences. Since the human genome consists of somewhere between 100–140,000 genes, it would be very resource demanding to mass-sequence human genomes in this manner.

Another disadvantage with using microarrays is that the limitations of current construction technology (e.g.

photolithography) does not make it possible to create pixels of less than about 10×10 micrometers. Thus, only a fraction of the resolution potential of the fluorescence scanner is utilised. Current fluorescence scanners are capable of distinguishing pixels of 0.1×0.1 micrometer, which means that microarrays can contain 10,000 times as much information as they currently contain.

It would therefore be advantageous to develop new methods/principles of identifying long sequence pieces where the combination problems mentioned above could be avoided. It would likewise be advantageous to develop new methods/principles that make it possible to sequence long target sequences without having the length of the sequence pieces that must be identified increase exponentially with the length of the target sequence.

Another sequencing method (for example as embodied in U.S. Pat. No. 5,714,330) that is based on identification of sequence pieces consists of distributing fragmented target DNA over a reading plate. Thereafter, the target DNA is treated so that a fluorescence signal representing one or several of the first base pairs is fixed to the target DNA. The fluorescence signals for each position is read before the procedure is repeated with the next base pair(s) in the target DNA. When the DNA molecules have fixed positions on the reading plate, it becomes possible to construct longer pieces with sequence information by running several cycles.

The ability to read several base pairs per cycle is limited because the number of unique fluorescence signals that are required increase exponentially with the number of base pairs. In order to read one base pair, four colours are required, two requires 16, three requires 64, etc. It is uncertain whether current technology makes it possible to distinguish between 64 different fluorescence colours. Regardless, the demands on reading time and the costs would increase considerably with the use of multiple colours. The solution would then be to perform many cycles. This in turn means an increase in the number of enzymatic steps and fluorescence readings.

Even if it were possible to identify relatively long pieces of sequence with the above-mentioned strategy, important problems would be encountered in the reconstruction. Biological DNA is very non-randomised in its composition. Short and long-sequences are often repeated in several places on a "macro" and "microscopic" level. Reconstruction is particularly difficult in areas with repetitive DNA sequences. These can often be of biological interest; e.g. the length of trinucleotide "repeats".

A new approach which allows the above mentioned problems to be overcome has now been developed. Surprisingly it has been found that if sequence information is obtained which is linked to positional information (ie. information of the position of that sequence within a target sequence), long sequences can be identified accurately. Furthermore, the present invention provides new methods of sequencing which may be used with or without positional information in which the signal associated with one or more bases is amplified, referred to herein as magnification.

Thus according to a first aspect the present invention provides a method of sequencing all or part of a target nucleic acid molecule comprising at least the steps of:
a) determining the sequence of a portion of said nucleic acid molecule;
b) determining the position of said portion within said nucleic acid molecule; and
c) combining the information obtained in steps a) and b) to obtain the sequence of said molecule.

Conveniently, the sequence and position of multiple portions are determined and this information is combined.

As used herein the target nucleic acid molecule refers to any naturally occurring or synthetic polynucleotide molecule, e.g. DNA, such as genomic or cDNA, RNA, e.g. mRNA, PNA and their analogs, which where appropriate may be single, double or triple stranded. The part to be sequenced preferably comprises all of the target molecule, but may for example be less than the entire molecule, e.g. between 4 bases and 1 kb, e.g. 4 to 100 bases.

Preferably the portion which is sequenced has 4 or more bases and/or the position of said portion within said target molecule is determined with an accuracy of less than 1 kb (ie. to a resolution of less than 1 kb), particularly preferably less than 100 bases, especially preferably less than 10 bases. At a resolution of a few kb or better, it is usually not necessary to obtain sequence information on fragments of longer than 8–10 bases which is readily achieved by the methods described herein.

Sequence information may be obtained in any convenient manner and is appropriately obtained for one or more bases, especially preferably 2 or more bases, e.g. 2 to 20 bases, conveniently 4 to 10 bases. As will be appreciated it is imperative that the sequencing technique described above which relies on placement of the sequence portions within the target molecule, allows the retention of positional information which may be assessed simultaneously or separately to the sequence information. A number of appropriate techniques are described below.

Positional information may similarly be obtained in a number of convenient ways and these methods are also described below.

As mentioned above, in this aspect of the invention, the sequence which is obtained must be informationally linked to its position in the target sequence. This may be achieved in a number of ways, for example by sequencing the end or internal region of a nucleic acid molecule and establishing its position by reference to a positional indicator which may for example be the size of the molecule (e.g. length or volume), the intensity of a generated signal or the distance to a positional marker or anchor. Sequence information may be obtained by conducting one or more cycles of a sequencing reaction.

As mention previously, one of the difficulties in sequencing long molecules is that it becomes increasingly difficult to distinguish the different relative sizes of molecules which vary only by a single base as they become longer. In one embodiment, the present invention overcomes this particular problem by "magnifying" the difference in size, intensity, length or signal between molecules. Thus, in a preferred aspect the present invention provides a method of sequencing all or part of the sequence of a target nucleic acid molecule wherein 2 or more bases (e.g. 3 or more, preferably 4 or more) are sequenced per cycle of sequencing and/or the signal associated with each base is magnified.

As used herein a "cycle" of sequencing refers to execution of the series of steps resulting in an end product which may be processed to obtain sequence information, e.g. by generating or reading a signal therefrom. Preferably in magnification and sequencing reactions described herein more than one cycle is performed, e.g. 2 or more cycles, especially preferably more than 4 cycles, e g. up to 10 cycles.

"Magnification" of a signal associated with a base refers to enhancement of a signal which is associated with, or may be attributed to, a single base. This may for example be an increase in size (where the signal is the size of the base) or development of a new signal, e.g. the addition or association of a label or other signalling means with that base.

Increasing the length of the sequence portions that are identified can compensate for low precision in size determination. Thereby, the potential of mass spectrometry, gel sorting and similar methods can be utilized, at the same time as enabling the use of methods of size determination that currently are not sufficiently precise, e.g. flow cytometry, DNA stretching, etc.

Magnification of the difference between molecules can be achieved in a number of ways. Firstly, several bases may be sequenced (e.g. 4 or more) per cycle such that the resultant molecules differ in length by 2 or more bases and can hence be discriminated e.g. in a sequencing ladder which simultaneously provides positional information (see for example Example 17). Alternatively the information embodied by each base may be magnified making discrimination easier. Examples of these different techniques are described below.

Sequencing of 2 (e.g. 4) or more bases per cycle can be performed by any convenient technique. In sequencing methods relying on positional information, any technique may be used providing the sequence information which is obtained can be related back to the position of those bases within the target molecule. In such cases, for example, hybridization to complementary probes (e.g. carried on a solid support) may be employed in which the identity of the probes to which the target molecules are bound are indicative of the terminal sequence of a target molecule. For example solid supports carrying probes complementary to all 2-base permutations, ie. carrying 16 different probes may be used. Similarly, probes to all 4-base permutations, ie. 256 different probes could be attached to a solid support for capture of target molecules with complementary sequences.

In an exemplary procedure, all target molecules that do not end with AAAA (SEQ ID NO:1) (when the probe ends in TTTT (SEQ ID NO:2)) would not bind and would be removed. Similarly at other addresses, target molecules having particular end sequences would bind selectively. The target molecules may be double stranded (with single stranded overhangs) or single stranded such that sequences could be bound to and identified at the terminal ends or also internally, respectively. If PNA was used as the complementary probe, since such molecules are able to bind to double stranded forms, internal sequences, of double stranded forms could also be bound. In general terms this technique is referred to herein as sorting based on one or cycles. This technique may be coupled to other techniques as described herein.

As a reverse of the above described technique, sequencing may be performed by fixing single stranded target DNA to a solid substrate. The target DNA may then be mixed and hybridized, for example with 16-fragment adapters. Adapters are described hereinafter, but generally refer to molecules which adapt the target sequence to a signal-enhanced or magnified target sequence. Adapters that have not been hybridized are then washed away from the solution. This leaves only adapters with overhangs that are complementary to the single strand DNA. With the aid of for example the analysis methods described herein one can establish which adapters remain in the solution and consequently what sequence pieces of 16 base pairs are contained in the DNA.

This sequencing technique represents a preferred feature of the invention when performed in conjunction with positional information or when used as a sequencing technique alone. In this method the information carried by a single base is magnified, e.g. by multiplication of that base or replacement or enhancement of that base with a magnifying tag which can be used to generate a signal. (Magnification as referred to herein is also in some instances referred to as "conversion".)

Magnification of a target nucleic acid molecule may be achieved by multiplying, e.g. doubling a target molecule, or portion thereof containing the portion to be sequenced, one or more times. It will be appreciated that detecting the differences between molecules of e.g. 10 and 11 bases is more-difficult that detecting the difference between magnified molecules of 320 and 352 bases (doubled 5 times). The principled doubling can therefore be used, e.g. to improve most DNA analysis methods. One appropriate technique for achieving this is described in Example 11. Other appropriate techniques may also be used.

This method can therefore be used to improve most methods based on detecting size differences between nucleic acid molecules, e.g. gel or non-gel based techniques. This strategy also makes it possible to analyse nucleic acid material using techniques that are not sensitive enough to distinguish the difference of a few base pairs. For example, an improved Maxam-Gilbert method is possible in which a single stranded nucleic acid molecule (e.g. with 5'-biotin) is attached to a streptavidin bearing plate. Sequencing is then conducted and the plates washed after which the resultant nucleic acid molecules are doubled, e.g. 10 times, resulting in steps of 1024 base pairs. These lengths may be determined by one of the analysis techniques described below.

Thus viewed from a further aspect the present invention provides a method of sequencing all or part of a target molecule as described herein wherein the signal associated with each base (or more than one base) is magnified by increasing the number of times that said base appears in said sequence.

As used herein the "signal" attributed to a particular base (or more than one base) refers to the possibility of detecting that base (or collection of bases) by virtue of its properties either directly or indirectly. Thus this could refer to its properties of for example size, charge or spatial configuration which might be detected directly or indirectly or by association of one or more further molecules, e.g. labelling moieties with said base from which a signal may be generated directly or indirectly. Thus a signal may be provided which may be detected directly or a signalling means may be provided through which a signal may be generated. The signal may be unique to more than one base, ie. the signal may be indicative or representative of a pair of bases, e.g. a signal for AA may be used which is different to the signal used for AT etc. Different mechanisms for associating such molecules and signals that may be generated are described in more detail below.

A further preferred magnification technique involves the association of one or more unique signals (or means for producing such signals) with one or more bases in a sequence. When said signals are associated with more than one base, this may be achieved by using a series of signals (or signalling means) each corresponding to one or more bases or a single signal (or signalling means) unique to two or more bases. Conveniently these signals are carried on magnifying tags which may become attached to the sequence through an adapter molecule. "Association" as used herein refers to both replacement of said base (or more than one base) with said signal (or signalling means) or addition of said signal (or signalling means) to said base (or more than one base) such that they coexist. The signal (or signalling means) need not necessarily be attached directly to (or specifically replace) the base (or more than one base) with which it is associated and association may be indirect, e.g. through the intermediacy of one or more further molecules. Association may be through any appropriate chemical interactions, e.g. hydrophobic, ionic, covalent etc., but preferably is by covalent interaction with the target nucleic acid molecule or associated molecule.

"Corresponding" as used herein refers to the relationship between a base and a signal, for example as provided by a magnifying tag, which may be read as indicative of the presence of that particular base. Alternatively in the context of the mapping procedure this refers to the relationship between a nuclease and a signal used as a marker indicative of cleavage with that nuclease.

As used herein a "magnifying tag" is a single molecule or complex of molecules which comprise a tag portion which provides a means for generating one or more signals, e.g. carrying a label or a site to which a label may be bound. Means for generating one or more signals may be incorporated in instances in which information other than sequence information is required, e.g. as an indicator of information relating to the target molecule or the cleavage protocol which is used. A magnifying tag may inherently carry a further portion for specifically associating with one or more nucleotide bases, e.g. when the magnifying tag is a polynucleotide. In this case the tag is considered to additionally comprise the adapter as described herein. Alternatively, the magnifying tag may be attached to, or contain means for attachment to, an adapter which allows binding to a target sequence.

In general terms an example of the process may be described as follows. Base pairs in the target nucleic acid material are associated with four different tags (hereafter called magnifying tags) that represent each of the four bases Adenine, Cytosine, Guanine, and Thymine. Thus, where there was an A-T base pair "magnifying tag A" is associated, C-G is associated with "magnifying tag C", etc. Thereby new DNA molecules are generated where the original base order of e.g. ACGTT (SEQ ID NO:3) is augmented by "magnifying tag A"—"magnifying tag C"—"magnifying tag G", etc. Each magnifying tag provides a means of producing a signal and may in a preferred feature be a polynucleotide molecule. In that case the length of the four tags may vary from two base pairs to several hundred kbp (or more if desired), according to requirements. Correspondingly, the DNA fragments can contain reporter genes and other biological information or consist only of sequences without a known biological function.

Any convenient magnifying tag may be used, but it is of course imperative for sequencing purposes that at least 4 unique tags exist, ie. for each base. Of course the tag to be used depends on the sequencing technique and, where this is performed, the method used to extract the positional information.

Tags may be provided in a number of alternative forms. The tag has means for direct or indirect detection through the generation of unique signals, ie. the tag comprises one or more signalling means. Fluorescence, radiation, magnetism, paramagnetism, electric charge, size, and volume are examples of properties with which the magnifying tag particles can be equipped in order to be able to detect them and separate them from each other. These properties may be present on one or more labels present on the magnifying tags, the signals from which may be detected directly or indirectly. Appropriate labels are those which directly or indirectly allow detection and/or determination of the magnifying tag by the generation of a signal. Such labels include for example radiolabels, chemical labels (e.g. EtBr, TOTO, YOYO and other dyes), chromophores or fluorophores (e.g. dyes such as fluorescein and rhodamine), or reagents of high electron density such as ferritin, haemocyanin or colloidal gold. Alternatively, the label may be an enzyme, for example peroxidase or alkaline phosphatase, wherein the presence of the enzyme is visualized by its interaction with a suitable entity, for example a substrate. The label may also form part of a signalling pair wherein the other member of the pair may be introduced into close proximity, for example, a fluorescent compound and a quench fluorescent substrate may be used.

A label may also be provided on a different entity, such as an antibody, which recognizes at least a region of the magnifying tag, e.g. a peptide moiety of the magnifying tag. If the magnifying tag is a polynucleotide, one way in which a label may be introduced for example is to bind a suitable binding partner carrying a label, e.g. fluorescent labelled probes or DNA-binding proteins. Thus, alternatively the tag may carry a molecule or itself be a molecule to which a label may be attached, e.g. by virtue of its sequence. Labels may be attached as single molecules or in the form of microparticles, nanoparticles, liposomes or other appropriate form of carrier.

In a preferred aspect, the magnifying tags are themselves nucleic acid sequences of at least 2 bases, e.g. from 30 to 1000 bases, preferably 6 to 100 bases, especially preferably 10 to 30 bases in length. These sequences may have one or more labels attached to them, e.g. by the use of fluorescing probes, proteins and the like complementary to that sequences, from which one or more signals may be generated. Alternatively, protein molecules may comprise the tag or be attached to the tag and may be recognized, e.g. by immunoreagents or by another appropriate binding partner, e.g. DNA: DNA-binding proteins. Other properties of such tag molecules may also be examined, e.g. cleavage patterns (by restriction enzymes, or proteinases), charge, size, shape etc.

The magnifying tags may also contain information by virtue of its sequence which can be used to generate a signal. Thus, another alternative strategy is to create chains that contain reporter genes, cis-regulatory elements, and the like. These can then be transfected/transformed into cells where the composition of e.g. reporter genes or cis-regulatory elements are converted into one or several signals. Whilst this technique requires a transformation/transfection step, the cells may be programmed to perform the complete sequencing reaction including the conversion step (ie. the addition of magnifying tags). A huge repertoire of signals may be generated, such as the use of genes expressing fluorescence proteins or membrane-proteins that can be labelled with fluorescence, genes expressing antibiotic resistance etc. Signal quality, quantity and position can be exploited in addition to changes with time and other properties to indicate the presence of particular bases in a sequence.

Conveniently solitary cells are used in these methods, although multicellular organisms or structures could also be used. Non-living cell equivalents could also be used for the generation of the labels or signals, e.g. using nanotechnology. Where appropriate, signals which are generated may be directed to different locations for identification, e.g. by the use of different promoters. Examples of how this technique might be performed is shown in Example 18.

Whilst conveniently 4 magnifying tags specific to each of the nucleotide bases may be used, as mentioned above, where appropriate magnifying tags which may be used to generate signals unique to more than one base may be used. Thus for example, for reading methods where e.g. 16 different fluorophores can be used, it may be appropriate to use 16 different tags which are used to generate 16 different signals that represent all permutations of two base pairs.

In other contexts, it may be appropriate to use fewer than four different tags. For example, only two magnifying tags where one is for A/T while the other is for C/G. Another alternative is to use less than 4 unique signal events to create 4 magnifying tags which give rise to 4 unique signals (in instances in which individual bases are tagged) by virtue of particular combinations of those signal events. For example, sequencing information may be converted into a binary system. In this system, adenine may-be converted to a series of signal events "0"+"0", cytosine to "0"+"1", guanine to "1"+"0", and thymine to "1"+"1". In principle, it is then enough to have one or perhaps two colours or unique signals to read the sequencing information. This may in turn mean that less costly fluorescence scanners can be used at the same time as reading is faster than if several signals had been used. The use of a single signalling means spatially arranged to provide at least 4 unique magnifying tags, e.g. to produce a binary type readout forms a preferred aspect of the invention, ie. said signal comprises a pattern made up of a single signal event which creates a unique signal on said magnifying tag. In this case a signal event refers to a measurable signal e.g. the fluorescence from a single molecule or other such label. When multiple magnifying tags, preferably 20 to 100 tags, are used these are preferably associated linearly, e.g. as a long DNA fragment, to allow positional information to be preserved when this is required.

Association of the tag (albeit not necessarily directly, e.g. this may occur through an adapter) with the base (or more than one base) which it represents relies on specific base recognition via for example base-base complementarity. However, complementarity as referred to herein includes pairing of nucleotides in Watson-Crick base-pairing in addition to pairing of nucleoside analogs, e.g. deoxyinosine which are capable of specific hybridization to the base in the target nucleic acid molecule and other analogs which result in such specific hybridization, e.g. PNA, RNA, DNA and their analogs.

Thus probes could be used which are for example made up of DNA, RNA or PNA sequences, or hybrids thereof, such as oligonucleotides of for example 4 to 20 bases, preferably 6 to 12 bases in length which bind to specific regions of a target molecule (where the complementary sequence is present) and have attached thereto a magnifying tag, or series of tags, in which each tag represents one or more of the nucleotide bases to which the probe binds. In this case the probe acts as an adapter molecule facilitating binding of the tag to the target sequence. Alternatively, mixes of degenerate probes may be used with only one or more specific invariant bases at a particular position, e.g. NNNNAA. Preferably the number of magnifying tags which are present correspond to the number of specific bases of the probe to which they are attached, which become bound. However, if unique tags are made for 2 or more base permutations correspondingly less tags are required.

This technique may be used to identify discrete portions or parts of a target molecule or to obtain the sequence of all or essentially all of the target molecule's sequence.

A more elegant sequencing alternative however is provided by the production of a contiguous magnifying tag chain the signals from which can be read to derive the sequence. Although there are other ways of achieving this effect the most convenient technique involves the insertion of the magnifying tags into the target molecule. Especially preferably this reaction is performed cyclically allowing the conversion and later sequence reading of a series of bases.

In order to insert the magnifying tags into the target molecule in association with the base (or more than one base) to be magnified it is necessary to use complementarity to, or recognition of, that base (or more than one base) and surrounding bases. This complementarity may be used to directly introduce a magnifying tag or may be used to initiate a procedure which ultimately introduces a tag corresponding to that base (see Example 4).

Conveniently this is achieved by creating an overhang (ie. a region that is single stranded) in the target nucleic acid molecule that could be ligated to a magnifying tag. (Such an overhang is however not necessary where a tag molecule or its intermediary, e.g. its adapter, can recognize and bind to double stranded forms, e.g. PNA). One method is to ligate the ends of the target molecule with short DNA molecules that contain a binding site for a restriction enzyme that cleaves outside its own recognition sequence, e.g. class IP or IIS restriction enzymes. These enzymes exhibit no specificity to the sequence that is cut and they can therefore generate overhangs with all types of base compositions. The binding site can be located so that an overhang is formed inside the actual target molecule, e.g. DNA when the DNA molecules are incubated with the restriction enzyme in question. In practice, it is probably preferable to choose enzymes that generate 3–4 base pair overhangs (see Example 19 which shows the general procedure for producing such overhangs on target molecules which have been amplified and attached to a solid support).

Over 70 classes of IIS restriction endonucleases have been identified and there are large variations both with respect to substrate specificity and cleaving pattern. In addition, these enzymes have proved to be well suited to "module swapping" experiments so that one can create new enzymes for particular requirements (Huang-B, et al.; J-Protein-Chem. 1996, 15(5):481–9, Bickle, T. A.; 1993 in Nucleases (2nd edn), Kim-YG et al.;PNAS 1994, 91:883–887). Very many combinations and variants of these enzymes can therefore be used according to the principles described herein.

Class IIS restriction endonucleases have been used for several different purposes. For example, as universal restriction endonucleases that can cleave a single strand substrate at almost any predetermined site (Podhajska, A. J., Szybalski, W.; Gene 1985, 40:175–182, Podhajska, A. J., Kim, S. C., Szybalski.,W.; Methods in Enzymology; 1992, 216:303–309, Szybalski, W.; Gene 1985, 40:169–173)

In sequencing contexts they have been used for the previously mentioned method described in U.S. Pat. No. 5,714,330. In these cases however the introduction of multiple magnifying tags which remained associated with the target molecule was not considered.

Cleavage with IIS enzymes result in overhangs of various lengths, e.g. from −5 to +6 bases in length. Once an overhang has been created, magnifying tags, which may be carried on adapters, corresponding to one or more of the bases in the overhang may be attached to the overhang.

A number of different ways in which the magnifying tags may be incorporated using the IIS system or similar systems are described below.

The first described technique involves the use of adapters which carry one or more magnifying tags and which have a complementary overhang to the target nucleic acid molecule which has been modified to generate a single stranded region, ie. an overhang. The adapter itself also carries the recognition site for a further IIS enzyme which may be the same or different to the enzyme used to generate the overhang. An example of this technique is illustrated in Example 1.

Briefly, the target sequence is ligated into a vector which itself carries a IIS site close to the point of insert or the target sequence is engineered to contain such a site. The appropriate IIS enzyme is then used to cleave the IIS site which when appropriately placed results in an overhang in the target sequence. In one embodiment, at least one end of the cut vector is made blunt, e.g. by the use of a further restriction enzyme site adjacent to the IIS.

Appropriate adapters may then be used to bind to, and thereby allow magnification of, one or more bases of the overhang. In the case of single base magnification, degenerate adapters having single stranded portions of the form, e.g. for a four base overhang, ANNN (SEQ ID NO:4), TNNN (SEQ ID NO:5), CNNN (SEQ ID NO:6) and GNNN (SEQ ID NO:7) and magnifying tags A, T, C and G, respectively may be used. Alternatively the adapters may carry more than one magnifying tags corresponding to more than one of the overhang bases, e.g. having an overhang of ATGC (SEQ ID NO:17), with corresponding magnifying tags to one or more of those bases attached in linear fashion where appropriate.

Once the overhang of the adapter and the cleaved vector have been hybridized, these molecules may be ligated. This will only be achieved where full complementary along the full extent of the overhang is achieved and aids the specificity of the reaction. Blunt end ligation may then be effected to join the other end of the adapter to the vector. By appropriate placement of a further IIS site (or other appropriate restriction enzyme site), which may be the same or different to the previously used enzyme, cleavage may be effected such that an overhang is created in the target sequence downstream of the sequence to which the first adapter was directed. In this way adjacent or overlapping sequences may be consecutively converted into sequences carrying magnifying tags, the signals from which can subsequently be read to determine the sequence by the methods described later herein. The sequencing of overlapping sequences effectively allows proof-reading of sequences which have been read in previous cycles allowing verification.

A slight modification of this technique is shown in Example 2 in which a blunt end is not produced, but instead once the vector has been produced and cleavage effected with the IIS or similar enzyme, a further restriction enzyme is used which creates an overhang which is universally complementary to the terminal of all adapters which are inserted into the vector. This similarly allows ligation of the adapter and therefore magnifying tags into the vector.

A similar but more elaborate example is illustrated in Example 3. In this case non-complementary overhangs are created corresponding to adjacent stretches of DNA. These are both hybridized to adapters which have attached appropriate magnifying tags. Only one of the adapters contains the restriction enzyme site for the next cycle so that sequencing occurs unidirectionally. Clearly to allow the binding of adapters with these different properties, the overhangs of adjacent stretches of DNA must be discriminatable, e.g. be of different length. This can be achieved by using different restriction enzymes which result in different overhang lengths. The ends of the two different types of adapters are intentionally complementary and thus would hybridize and may be ligated to form the vector. The restriction site in the adapter which contains it is appropriately placed such that the cleavage site is displaced further into the target sequence to allow sequencing of adjacent sites.

Thus for example if overhangs of 5+4 are created, and the cleavage site is displaced 4 bases into target sequence, when the next 9 bases are converted to overhang and thereafter associated with magnifying tags, 5 of these bases will have been associated with magnifying tags in the previous cycle. This allows verification of the identity of the previous 5 bases when reading the sequence and thus introduces a proof-reading mechanism.

Other techniques using the IIS system include the use of Klenow fragment of DNA polymerase and relies on the fact that most DNA ligases are unable to ligate overhang of different sizes. This is shown for example in Example 5. In this technique an overhang is created which is longer than the overhang of the adapter. The target overhang is reduced by Klenow in the presence of one type of nucleotide. Only the target which has been appropriately extended by one base will bind to the adapter allowing identification of the base that was introduced by virtue of the corresponding magnifying tag attached to that adapter.

Other techniques illustrated in Examples 4–7 involve the hybridization of adapters carrying magnifying tags to a single stranded target which are then ligated to that target. The adapter then is used as a primer for a polymerase extension reaction to form double stranded molecules. A further alternative uses sorting adapters (which in this case need not necessarily be associated with magnifying tags and may simply be used for sorting) in which the adapters are attached to a solid support which have an overhang in excess of the overhang created on target molecules. Thus for example the adapters may have an overhang of 8–10 bases. If for example the DNA pieces (in double stranded form) have a 4-base overhang these molecules will only ligate if the bases complement one another at the innermost bases of the overhang. Polymerase extension is then performed. The prerequisite for a successful polymerase extension reaction is that the rest of the adaptor's overhang is complementary to the DNA piece so that it can function as a primer. In this way polymerase extension will only occur if the target molecule's terminal sequence is complementary to the adapter's overhang.

Alternatively hybridization alone may be used and magnifying tags which are associated with stretches of the sequence which are adjacent may conveniently be ligated together.

A further alternative relies on the specificity of metabolic enzymes for their recognition sites. Such a technique is illustrated in Example using restriction enzymes. A number of alternative enzymes may however also be used such as transposases etc. In this method the target molecules that are to be sequenced are cleaved to produce blunt ends with four different standard restriction enzymes and ligated into 4 different DNA molecules each ending with a portion of the restriction site for one of 4 different restriction enzymes (which produce an overhang on cleavage). These are then ligated onto the target molecules. Where the target molecules end with bases which provide the remaining bases of the restriction site, a restriction recognition site will be produced. This can be determined by cleavage with that restriction enzyme. Only those molecules that have that recognition site in complete form will be cleaved. To recognize those molecules which have been cleaved, adapters may be used which are complementary to the overhang. These adapters may then carry one or more appropriate magnifying tags depending on the number of bases provided by the target molecule to complete the restriction site. The molecule may then be circularized to allow repeat cycling. Conveniently the adapters have within their sequence appropriately sited restriction sites for both blunt end and overhang producing restriction enzymes, such that reiterative cycles may be performed by allowing the introduction of magnifying tags corresponding to adjacent or overlapping target sequence regions.

The present invention thus relates in one aspect to a method of identifying a portion of a target nucleic acid molecule wherein an adapter molecule comprising a moiety which recognizes and binds to said portion and a moiety comprising one or more magnifying tags, preferably a chain of said tags representing the bases in said portion, is attached to, or substituted for, said portion.

Thus viewed from a preferred aspect the present invention provides a method of magnifying all or part of the sequence of a target nucleic acid molecule wherein one or more magnifying tags are associated with one or more bases in the target sequence, wherein said tags correspond to one or more bases in said target sequence. Preferably said magnifying tags together correspond to at least two, preferably at least 4 bases. Preferably said magnifying tags each correspond to at least two, preferably at least 4 bases. In an alternative embodiment each magnifying tag corresponds to one base and a chain of magnifying tags together corresponding to at least 4 bases, e.g. 8 to 20 bases is employed. This may for example be achieved by performing multiple cycles adding a single magnifying tag in each cycle or by using chains of tags which are associated in a single cycle.

Preferably said method comprises at least the steps of:

a) converting at least a portion of said target sequence to a form suitable for binding an adapter molecule, preferably to single stranded form;

b) binding to at least a portion of said region suitable for binding an adapter molecule, preferably said single stranded region, created in step a) an adapter molecule comprising one or more magnifying tags, or comprising a means for attaching one or more magnifying tags, which tags correspond to one or more bases of said target sequence, preferably corresponding to one or more bases of said region suitable for binding said adapter molecule, preferably said single stranded region, to which said adapter molecule binds or in proximity to said region;

c) optionally ligating said target molecule to said adapter molecule such that at least said magnifying tags remain associated with said target molecule;

d) optionally repeating step a), wherein said region suitable for binding said adapter, preferably said single stranded region, which is created includes one or more bases not associated with a magnifying tag according to step b);

e) optionally repeating steps b) to d) wherein said adapter molecule binds to an adjacent or overlapping region of said target molecule relative to the region to which the adapter molecule of the previous cycle bound.

Step e) may be omitted in some techniques, e.g where sequencing is achieved by coupling magnification and sorting, such that only one cycle of magnification is performed.

"Conversion" to a form suitable for binding an adapter molecule is necessary only if a target molecule is not already in an appropriate form. Thus to bind PNA molecules, conversion of double stranded target molecules is not necessary. Similarly, if a molecule is single stranded conversion is not necessary to bind adapters which are oligonucleotides. In some cases however conversion may be required, e.g. by melting DNA fragments, to allow specific and selective binding of the adapter. It is not necessary to convert the entire molecule to a different form and in appropriate cases only a portion will be converted. This portion should comprise at least the length of the binding portion of the adapter, thus preferably 4 to 500 bases, e.g 6 to 30 bases in length.

Reference in this context to conversion from one form to another should not be confused with use of the word conversion when used in relation to magnification.

As used herein an "adapter molecule" is a molecule which adapts the target sequence to a signal-enhanced or magnified target sequence. Adapter molecules as used herein are single molecules or complexes of molecules which may be the same or different in type. The adapter sequence comprises a binding moiety which binds to said target sequence, e.g. a protein recognizing a particular base sequence or more preferably a polynucleotide sequence complementary to one or more bases of the target sequence. Preferably the binding sequence is 3 to 30 bases, preferably 4 to 10 bases in length. Adapter molecules additionally comprise one or more magnifying tags or means for attaching such tags, e.g. sequences which are complementary binding partners. Preferably adapters contain one or nuclease recognition sites, especially preferably a restriction site (or at least recognition site) for a nuclease which cleaves outside its recognition site, especially preferably restriction sites of IIS enzyme or their analogs, particularly FokI and other enzymes described herein. Preferably sites for other restriction enzymes are excluded from the adapters.

Conveniently adapter molecules may be exclusively comprised of a nucleic acid molecule in which the various properties of the adapter are provided by the different regions of the adapter. However, as mentioned previously magnifying tags may take a variety of forms, which include labels such as proteins, etc. The adapter may thus provide the molecule to which magnifying tags may be bound, e.g. provide appropriate binding partners in addition to the region for binding to the target.

In step c) it is indicated that "at least" said magnifying tags remain associated. It is thus envisaged that the adapter or portions thereof may be removed.

As used herein a "chain" of magnifying tags refers to tags which have been linked either before a cycle of magnification and attached to one adapter or linked together at the end of each cycle or a combination of both. The linkage may be by any appropriate means however attachment by covalent means is preferred.

Preferably the above method is used in sequencing methods of the invention which comprise the above steps in addition to determining the sequence of said target molecule by identifying the signals generated from the magnifying tags attached to said target sequence. In order to identify the magnifying tags a readable signal must be generated from the magnifying tags. This may be present inherently, for example where the tags carry a label with certain properties (e.g. a radioactive label), or may require further steps for its generation, e.g. the addition of further molecules (e.g. binding, partners themselves carrying labels) or processing of the magnifying tags into a readable form (e.g. conversion to a readable signal such as by expression of a reporter gene in which the signal which is read is the expressed protein).

Thus in a preferred aspect the present invention provides a method of sequencing all or a part of a target nucleic acid molecule in which at least a portion of the sequence of said target nucleic acid molecule is magnified, preferably by the use of one or more magnifying tags associated with one or more bases in the target sequence, wherein said magnified sequence is optionally converted into a readable signal and said sequence is determined by assessment of the signals which are generated.

"Assessing" as used herein refers to both quantitative and qualitative assessment which may be determined in absolute or relative terms.

Ligation may be achieved chemically or by use of appropriate naturally occurring ligases or variants thereof. Whilst ligation represents only a preferred feature of the invention, this is conveniently used to increase specificity. Compared to hybridization, specificity is increased by a factor of ten if ligation is based on T4 DNA ligase. This is important since the sequencing methods that are based on hybridization in many cases are associated with an unacceptably high error rate. Furthermore, by using thermostable ligases, such as Pfu, Taq, and TTH DNA ligase specificity will be improved while efficiency increases dramatically so that the incubation time is reduced.

This method of sequencing using magnifying tags offers a number of advantages over known methods of sequencing. More than one base may be converted or magnified in each cycle thus reducing the number of cycles necessary for sequencing a particular length of target molecule. Depending of the choice of magnifying tags and the signals they produce, simplified read-out signals may be produced, e.g. the signals may be in the form of a binary read-out, ie. unique signals are generated for one or more bases by appropriate combination, e.g. linear or positional layout, of a single signalling event, e.g. fluorescence. This reduces the number of unique signalling events which are required. Thus instead of needing for example 16 different labels for each 2 base combination, or 64 different labels for each 3 base combination, in the present invention 16 or 64 or more unique signals may be generated by providing on each magnifying tag a pattern of a means for producing a single signalling event, e.g. a pattern of sites for binding a fluorescent probe.

The signal information may be tightly packed. The tags are not limited to only labelled nucleotides allowing greater flexibility in the types of magnifying tags which may be used and signals which may be generated. In some embodiments, even when cycling is not performed, large portions of a sequence may be sequenced by using chains of magnifying tags to those portions thus avoiding the complex reactions involved in repeat cycling and also the need to relate the information from each cycle to a particular target sequence, e.g. using target molecules fixed to a reading plate, which limits how the signal may be read (e.g. micro/nanopores or flow cytometers could not be used)

In preferred aspects of the invention, conversion of the target molecule to at least a partially single stranded form is achieved by using a single stranded molecule or by creating an overhang, e.g. by using an appropriate nuclease with a cleavage site separate from its recognition site, such as IIS enzymes.

Preferably when the reaction is performed cyclically, the magnifying tags of each cycle are joined, e.g. by association or ligation, together, e.g by the production of a single chain containing them. Furthermore, after ligation of said target molecule to said adapter molecule, said resultant molecule is preferably circularized. Conveniently this is achieved by introducing the target molecule into a vector (or by attaching a portion of the target molecule to a support allowing free interaction after cleavage within the molecule, see Example 22) and using appropriate steps of cleavage and ligation after said adapter molecule has been introduced. Alternatively the chains of magnifying tags which are generated may be transferred or copied to a distant site on the target molecule without the need for effective circularization. An appropriate protocol for performing this is illustrated in Example 9.

Another convenient technique which avoids the need for excessive cycling involves the hybridization of smaller converted fragments, ie. nucleic acid molecules with attached magnifying tags. These fragments may themselves have been subjected to one or more conversion cycles and then may be linked by complementarity to unconverted sequences or information carried in the magnifying tags, e.g. nucleotide sequences of the tags (see Example 10).

To effect cycling of the reaction the control of particular enzymes used in the reaction is necessary. This may be achieved in different ways depending on the enzymes which have been used. Thus, methylation may be used to prevent binding to and/or cleavage at restriction sites. Ligation may be prevented or allowed by controlling the phosphorylation state of the terminal bases e.g. by appropriate use of kinases or phosphatases. Appropriately large volumes may also be used to avoid intermolecular ligations. Small volumes are preferably used during the restriction reactions to increase efficiency.

Preferably in each cycle of magnification (or sequencing as described herein), at least two bases are converted, preferably between 3 and 100, especially preferably from 4 to 20 bases per cycle. Conveniently, more than one magnifying tag is associated with one or more bases in each cycle. For example, in a preferred embodiment, a collection (e.g. a linear series or chain) of tags, each corresponding to one or more bases, collectively corresponding to a portion of said sequence, are introduced, e.g. multiple tags, e.g. more than 4 tags, corresponding to for example 4 to 12 contiguous bases. Conveniently this may be coupled with such tags themselves being directed to more than one base, e.g. unique tags for each pair of bases.

As will be noted in Example 1 in a preferred embodiment, a nuclease having the properties described above is employed to generate the overhang. In addition said vector additionally comprises a restriction enzyme site to produce a blunt end cleavage at one of the ends resulting from nuclease cleavage to produce the overhang. Alternatively, a restriction enzyme distinct to the enzyme used to create the initial overhang may be used which produces an overhang which has precise complementary to one terminal of all adapters employed in the reaction.

To perform the method of Example 3, conveniently nuclease sites which produce adjacent or overlapping regions of overhang are used. These sites are preferably located in the adapters which are employed. In each cycle two adapters are used which are conveniently allowed to ligate together by the use of complementary overhangs at the ends terminal to the regions binding to the single stranded portions of the target sequence. Thus in preferred aspects of the invention particularly to allow proof-reading adapters which are used comprise recognition sites for 2 or more nucleases with cleavage sites separate from their recognition sites, in which cleavage with said nucleases produces single stranded regions which are adjacent or overlapping. As used herein "overlapping" refers to sequences which have bases in common or which are complementary to such sequences, ie. on a corresponding strand. Thus, in order to achieve overlapping regions, use may be made of each strand of a double stranded target and overlapping, but complementary regions may be sequenced. Conveniently to achieve this effect more than one adapter is bound to the target molecule in each cycle. This method allows proof-reading if overlapping regions are sequenced as more than one magnifying tag corresponding to a particular base or collection of bases will become attached allowing the generation of a repeat signal for that base. It will be appreciated that in accordance with the invention one tag per base is not required and thus a tag for a pair of bases etc. may be repeated.

In performing the embodiment involving the use of Klenow fragment, said single stranded region which is created in step a) is one or more bases longer than a single stranded region of nucleic acid present on the adapter. Furthermore, an additional step is required after step b) in which the length of the single stranded region of the target molecule is shortened by polymerization extension reaction.

For performing techniques involving single stranded target molecules, cycling conveniently involves the generation of double stranded molecules, preferably by the use of the adapter as a primer in polymerase extension reactions.

The method in which recognition sites are completed to identify molecules having the terminal bases necessary to complete that site provides a slightly different technique to that described in general terms above, since the adapter binds to an overhang but carries tags which may not necessarily correspond to one or more bases of the single stranded region to which the adapter molecule binds. The single stranded region is made up of overhang created by cleavage of the restriction site which comprises some of the bases of the target sequence. However, depending on the cleavage site, those bases may or may not be in single stranded form, for example, the overhang may be entirely composed of non-target molecule bases. Instead the addition of the appropriate tag relies on the fact that adapters will only bind where the restriction site has been completed. Thus step b) includes reference to tags which correspond to one or more bases of said single stranded region or in proximity to said region, e.g. adjacent to said region. Furthermore in this method prior to step a), a piece of linker DNA comprising a part of a metabolic enzyme recognition site is attached to said target molecule, followed by use of said enzyme, e.g. nuclease to produce the single stranded form of step a).

As mentioned previously, sequencing may be performed on the basis of sorting. This method may be used independently of, or in combination with the above described magnification technique. For example, the sequencing protocol may be effected by sorting target nucleic acid molecules on the basis of four base pairs, and subsequently the adjacent base pairs may be converted to determine their sequence. For example, a sorting strategy can consist of creating overhangs with four bases in the target nucleic acid molecules as described previously. It is then distributed among 256 wells that are all covered by short DNA molecules, sorting adapters (these adapters do not necessarily carry magnifying tags). The sorting adapters are fixed to the well walls and have overhangs with four bases that can complement the overhangs that have been created on the target DNA. In addition, the sorting adapters may contain a binding site for an IIS enzyme or other appropriate nuclease. The binding site is located in such a way that the respective IIS enzyme can create an overhang with the base pairs that are located beside the first overhang that was created in the target DNA. In order to increase the surface area with sorting adapters, an alternative is to fix them to a solid support such as paramagnetic beads or similar.

The DNA molecules in well 1 have AAAA (SEQ ID NO:1) overhangs, while the DNA molecules in well 2 have AAAC (SEQ ID NO:8) overhangs, etc. The 256 wells thereby cover all permutations of overhangs on four bases. When the target DNA are added to the wells together with ligase, the DNA molecules with TTTT (SEQ ID NO:2) overhangs will attach themselves to well 1, the target DNA with TTTG (SEQ ID NO:9) overhangs to well 2, etc. After having washed off target DNA molecules that were not ligated to the sorting adapters, us enzyme is added so that the target DNA molecules are freed at the same time as a new overhang is created that represents the next four base pairs in the target sequence. This overhang can then be used as the starting point for a new round of sorting, or one may proceed with conversion/magnification.

Sorting strategies where DNA molecules are washed away involve a relatively large loss of DNA molecules. However, most sequencing protocols proposed in this patent application are based on the analysis of individual molecules, and this means that very few DNA molecules are required. Thus, even a loss of 99.9% or more seldom presents a problem.

Instead of using different wells, an alternative would be to use different positions on a "microarray". At address 1 it is only DNA molecules that end with TTTT (SEQ ID NO:2) that are fixed, at address 2 it is DNA molecules with TTTG (SEQ ID NO:9) ends that are fixed, etc. Other alternatives are to let DNA molecules with different ends attach/convert at different times, the use of gel sorting, etc.

For example, one may use a strategy where there are 256 different sorting adapters distributed among 256 squares on a "microarray". In square 1, there are sorting adapters with AAAA (SEQ ID NO:1) overhangs, in square 2, they have AAAC (SEQ ID NO:8) overhangs, etc. Thus, the target DNA molecules will be sorted so that those with TTTT (SEQ ID NO:2) overhangs are attached to square 1, GTTT (SEQ ID NO:10) overhangs to square 2, etc. By also fixing the other end of the DNA piece to the substrate, e.g. with biotin/streptavidin, one can then continue to the next conversion/magnification step without the DNA molecules leaving their position on the reading plate. Another strategy for preventing the DNA molecules from leaving their positions is to use a reading plate that is divided into 256 wells/spaces.

It must also be pointed out that sorting can, of course, be done with fewer or more permutations than 256. Sorting can also be performed in several rounds. For example, if one uses a "microarray" with 65,536 different squares, it would be possible to identify eight bp by sorting through hybridization alone. This would be sufficient for many applications in order to perform a successful reconstruction. Sorting can therefore function as a sequencing method by itself, without having to use conversion or magnification.

Sorting can also be performed with non-ligase based strategies. In principle, one can use any method that is suitable for recognizing base pairs, including all the methods mentioned in connection with magnification.

It should also be pointed out that the specificity of a sorting method can be adjusted to most purposes by repeating the same sorting procedure one or several times. It may also be appropriate to use competing probes/overhangs in order to increase specificity.

Thus in a preferred aspect the present invention provides a method of sequencing a target molecule as described herein wherein said sequence is determined by assessing the complementarity of a portion of said molecule by a process comprising at least the steps of:

a) converting at least a portion of said target sequence to a form suitable for binding a complementary probe attached to a solid support or carrying a means for attaching to a solid support, preferably to single stranded form;

b) binding said complementary probe to at least a portion, preferably 4 to 12 bases in length, of said region suitable for binding a complementary probe, preferably said single stranded region created in step a);

c) optionally repeating steps a and b) wherein said complementary probe binds to an adjacent or overlapping region of said target molecule relative to the region to which the complementary probe of the previous cycle bound; and d) determining the sequence of said target sequence by identifying the complementary probe(s) to which said target sequence bound.

As used herein "probe" refers to an appropriate nucleic acid molecule, e.g. an oligonucleotide or PNA molecule.

Additional steps may also be included, e.g. the complementary probe may act as a primer and in which case polymerase reactions may also be performed as necessary.

As mentioned above, this sorting technique is preferably preformed by the use of multiple complementary probes and preferably between 2 and 8, especially preferably 4 bases are identifiable per cycle although this information may only be collected at the completion of the sequencing reaction. Particularly preferably complementary probes with between 2 and 8, preferably 4 unique invariant bases are attached to different discrete sites on said solid support. In the second and subsequent cycles, target molecules which are bound to said probes are transferred to one or more further solid supports bearing complementary probes to sequence adjacent or overlapping regions of said target molecules. In order to achieve this step a) may be performed in an analogous manner to that described for the magnification process, ie. the probes may themselves contain a restriction site for a nuclease, e.g. a IIS enzyme, which cleaves outside its recognition site, such that an appropriate overhang is generated.

The above procedure may be coupled with the magnifying procedure such that sequencing may be performed by a combination of sorting and magnification, e.g. after step b), overhang may be generated as described about and adapters carrying appropriate magnifying tags may be used to bind to said overhangs. The sequence may then be determined by a combination of reading the magnifying tags and by identification of the probe to which the target molecules have bound. Thus in a preferred feature the present invention provides a method of sequencing as described herein wherein a portion of said sequence is determined by the magnification method described herein and an adjacent or overlapping portion is determined by the use of complementary probes as described herein.

In most cases the technique adopted for positioning of sequence portions will depend on how the target DNA is generated for sequencing, e.g. if it starts from a common point, or if it is generated by fragmentation which results in target molecules starting from different points.

Nucleic acid molecules for sequencing may be generated in different ways. By treating a small amount of DNA with DNAse, sonication, vortexing or similar techniques nucleic acid molecules may be fragmented into pieces. Such techniques are well known in the art, see for example http://dna1.chem.ou.edu/protocol_book/ protocol_partII.html which describes protocols for random subclone generation. By adjusting the parameters of these techniques, it is possible to adjust the average size of the target DNA fragments (as a rule, the optimum is to have average sizes of a few hundred base pairs). The methods should also be relatively non-specific with respect to where they cut/break the DNA molecules so that statistically DNA pieces are obtained that are cut/broken in most places in the original sequence.

Studies show that the ends of the fragmented DNA molecules consist both of blunt ends and short overhangs of 1–2 bases. If desirable, the overhangs can be treated in such a way that they become blunt ends (Klenow filling-in, etc.).

Conveniently for performing preferred methods of the present invention, which relies on the production single stranded overhangs, nucleic acid molecules may be fragmented by procedures which produce such overhangs. As mentioned before, sonication, vortexing, and DNaseI create short overhangs. One can also use restriction enzymes that cleave non-specifically. Several studies have shown that IIS enzymes are particularly well suited to domain swapping tests where the DNA binding domain can be replaced. Therefore, new IIS enzymes can be created where the cutting domain is tied to a DNA binding domain that binds DNA non-specifically.

The overhangs generated by known IIS enzymes vary from −5 to +6 bases. If overhangs of more than six bases are desired, it may be appropriate to use other systems/strategies. One possibility is to use nicking enzymes that produce nicks in dsDNA outside of their own binding site. Two binding sites for such a nicking enzyme, that have an internal distance of more than six base pairs and that are placed on either side of the double helix should produce an overhang of more than six base pairs. In addition to existing nicking enzymes, it may also be possible to create new nicking enzymes, for example by mutating IP and IIS restriction enzymes.

As an alternative to fragmentation, it is also possible to choose a strategy where fragment of the target sequence are produced with the aid of PCR or similar methods. For example, one can start with a known sequence on the target DNA and then use this area as a template for a primer in a polymerase extension. If a method is used that terminates the polymerase extension reaction at arbitrary sites, a DNA ladder is created, in which there are DNA molecules of many different lengths, but all having one end in common. Alternatively, short randomized primers can be used so that all possible combinations of fragments are produced from the target sequence. However, a limiting factor when using polymerase extension is the extension lengths of the various polymerases.

Magnification techniques may be coupled to sorting and conversion techniques described herein. For example adapters may be used as primers when binding to single stranded targets. Polymerase reactions may furthermore provide means of establishing the existence of complementarity between adapters and target sequences.

In one preferred embodiment of the invention, target molecules are fixed to solid supports. This may be achieved in a number of different ways. The target molecule may be designed to have attached to one or more moieties which allow binding of that molecule to a solid support, for example the ends (or several internal sites) may be provided with one partner of a binding pair, e.g. with biotin which can then be attached to a streptavidin-carrying solid support.

Target molecules may be engineered to carry such a binding moiety in a number of known ways. For example, a PCR reaction may be conducted to introduce the binding moiety, e.g. by using an appropriately labelled primer (see for example Example 17). Alternatively, the target nucleic acid may be ligated to a binding moiety, e.g. by cleaving the target nucleic acid molecule with a restriction enzyme and then ligating it to an adapter/linker whose end has been labeled with a binding moiety. Such as would particularly suitable if an IIS restriction enzyme is used that forms a non-palindromic overhang. Another alternative is to clone the target molecule into a vector which already carries a binding moiety, or that contains sequences that facilitate the introduction of such a moiety. Such methods could similarly be used to introduce position markers as described in more detail below.

Alternatively nucleic acid molecules may be attached to solid supports without the need to attach a binding moiety insofar as the nucleic acid molecule itself is one partner of the binding pair. Thus, for example short PNA molecules that are attached to a solid support may be used. PNA molecules have the ability to hybridize and bind to double strand DNA and the undissolved nucleic acid material can therefore be attached to a solid support with this strategy. Similarly, oligonucleotide probes may be-used to bind complementary sequences to a solid support. Such a technique may also be used to begin sequencing by binding particular nucleic acid molecules to particular locations on a solid support as described below.

Appropriate solid supports suitable as immobilizing moieties for attaching the target molecules are well known in the art and widely described in the literature and generally speaking, the solid support may be any of the well-known supports or matrices which are currently widely used or proposed for immobilization, separation etc. in chemical or biochemical procedures. Thus for example, the immobilizing moieties may take the form of beads, particles, sheets, gels, filters, membranes, microfibre strips, tubes or plates, fibres or capillaries, made for example of a polymeric material e.g. agarose, cellulose, alginate, teflon, latex or polystyrene. Particulate materials, e.g. beads, are generally preferred. Conveniently, the immobilizing moiety may comprise magnetic particles, such as superparamagnetic particles. In a further preferred embodiment, plates or sheets are used to allow fixation of molecules in linear arrangement. The plates may also comprise walls perpendicular to the plate on which molecules may be attached.

Attachment to the solid support may be performed directly or indirectly and the technique which is used will depend on whether the molecule to be attached is a probe for identifying the target molecules or the target molecules themselves. For attaching the target molecules, conveniently attachment may be performed indirectly by the use of an attachment moiety carried on the nucleic acid molecules and/or solid support. Thus for example, a pair of affinity binding partners may be used, such as avidin, streptavidin or biotin, DNA or DNA binding protein (e.g. either the lac I repressor protein or the lac operator sequence to which it binds), antibodies (which may be mono- or polyclonal), antibody fragments or the epitopes or haptens of antibodies. In these cases, one partner of the binding pair is attached to (or is inherently part of) the solid support and the other partner is attached to (or is inherently part of) the nucleic acid molecules. Other techniques of direct attachment may be used such as for example if a filter is used, attachment may be performed by UV-induced crosslinking. When attaching DNA fragments, the natural propensity of DNA to adhere to glass may also be used.

Attachment of appropriate functional groups to the solid support may be performed by methods well known in the art, which include for example, attachment through hydroxyl, carboxyl, aldehyde or amino groups which may be provided by treating the solid support to provide suitable surface coatings. Attachment of appropriate functional groups to the nucleic acid molecules of the invention may be performed by ligation or introduced during synthesis or amplification, for example using primers carrying an appropriate moiety, such as biotin or a particular sequence for capture.

As described herein target molecules are conveniently attached to complementary probes which are attached to the solid support.

In techniques using multiple but discrete complementary probes the solid supports to which these different probes are attached are conveniently physically associated although the signals generated by attachment of a target molecule to each probe must be separately determinable. Thus for example, plates with multiple wells may be used as the solid support with different probes in the different wells, or regions of a solid support may comprise the different addresses, for example the different probes may be bound to a filter at discrete sites.

Attachment to a solid support may be performed before or after nucleic acid molecule fragments have been produced. For example target nucleic acid molecules carrying binding moieties may be attached to a solid support and thereafter treated with DNaseI or similar. Alternatively cleavage may be effected and then the fragments may be attached to the support.

In many contexts, the object is to sequence one or several sequences that are present inside or together with other sequences. For example, only 5–10% of human genome sequences are assumed to be of direct biological importance. For mass screenings of human genomes, it would therefore be useful to be able to avoid sequencing areas that are of minor biological importance.

Thus one strategy which may be used is to fix polynucleotides that complement the target sequences that are to be isolated to a solid support (the inside of a well, monodispersed spheres, microarrays, etc.). By hybridizing the polynucleotides in the sequence pool with polymers on the solid support, undesirable polynucleotides can be washed away before proceeding to the sequencing stage. If desired, specificity can be increased by performing several cycles of hybridization and washing. Even if it may be advantageous for individual applications, there is no dependence on whether the complementary polynucleotides are fixed in a regular pattern. Similar strategies based on ligation, PNA hybridization, etc. are also possible.

For example, to isolate specific mRNA/cDNA molecules, complementary cDNA/mRNA molecules can be fixed to paramagnetic spheres or the like. The spheres can then be mixed in a tube together with the solution that contains the target sequences. When the mRNA/cDNA molecules have been hybridized with the mRNA/cDNA that are fixed to the spheres, undesirable molecules can be washed away at the same time as the spheres are kept in the tube with a magnet or similar. The desired target molecules can then be released by increasing the temperature, changing the pH, or by using another method that dissolves the hybridized molecules.

A similar strategy that can be used for sequencing protocols done on a reading plate is to fix specific target sequences to determined addresses. For example, single strand target DNA can be hybridized to primers that are fixed to different addresses. If desired, the primers can then be used as templates for a polymer extension. By adjusting the primers to the target sequence, it can be addressed as desired.

A corresponding strategy can be to fix PNA molecules to the different addresses. PNA molecules are known to have the ability to recognize specific sequences in dsDNA and such a strategy can therefore be used to address dsDNA by using PNA molecules that recognize the sequences that one wants to fix.

As mentioned above, molecules which are sequenced which may be divided into two categories. Those which have one common end and one arbitrary end and those which have two arbitrary ends. Positional information may be obtained from these different types of molecules in different ways.

If all the target molecules have a common end, the length of each target molecule will be proportional to the distance between the common end and the other arbitrary end. Similarly, sequence information that is attributed to a particular portion of that target molecule may be positioned by calculating the distance from the common end to the site of the sequence information. Conveniently where that sequence information relates to the end of the target molecule, its position may be determined from the length/size of the entire molecule.

If nucleic acid fragments do not start from a common end, positional information may be obtained in different ways. One alternative is to create or identify characteristic fingerprints that vary from sequence to sequence. Thus, the position of a sequence piece can be derived by registering what fingerprint it is tied to, and possibly where in the fingerprint it is located. Very many techniques can be considered for use for creating characteristic patterns. The cleavage pattern of restriction enzymes in a DNA sequence can be registered, e.g. with the aid of "optical mapping" or similar methods.

One disadvantage of known "optical mapping" methods is that the cutting sites for the restriction enzymes that are used are not always cut. Likewise, incorrect cleavage can occur and there may be some uncertainty associated with the length measurements of the DNA fragments. Therefore, it is necessary to produce an average picture of each map piece based on an analysis of many identical DNA molecules. The problem is that it can be difficult to know what DNA molecules are identical.

Another problem with current methods of optical mapping is that treatment with restriction enzymes and the like must take place after the DNA molecules have been straightened out in order to be able to observe the internal placement of the DNA fragments. This reduces the availability of the DNA molecules for such things as enzymatic preparation. The present invention which provides end terminal sequencing in addition to positional placement allows such problems to be overcome. See for example the technique described in Example 23.

One can also use fluorescing probes/tags that create characteristic patterns. This is the principle behind the so-called "DIRVISH" technique. A similar strategy is to use atomic force microscopy (AFM), micro-/nanopores, or other methods for registering the size and location of proteins that are bound in characteristic patterns, etc.

One can also use cellular adapters as discussed previously. For example, if one transforms/transfects magnified target DNA into cells, one can take advantage of the fact that the transcription frequency of a reporter gene varies with the distance to cis-regulatory elements. If there is an enhancer at one end and one or more magnifying tags at the other consisting of reporter genes, the relative quantity of reporter proteins can be used to calculate the position value.

It is also possible to label or incorporate the target sequences with elements that are used to derive the position value. Such strategies can be advantageous, e.g. if it is difficult to distinguish between the fingerprints of two very similar sequences. For example, if one wishes to sequence sister chromosomes, one can integrate a large number of insertion elements (transposons or the like) that are arbitrarily integrated. If one then amplifies the chromosomes and use the insertion elements as position markers, there will be one or several characteristic patterns for each sister chromosome.

An alternative strategy that may be used which can introduce both a positional marker and allows identification of a sequence at that site involves the use of adapters as primers for a PCR reaction. The result of each PCR reaction will be two adapters that are connected, where the distance between the two adapters corresponds to the distance of the adapter sequences on the target DNA and simultaneously provides positional information.

The target molecule's sequence may provide the necessary means for producing a position marker without modification. For example, if some sequence information is known, a probe may be used to hybridize to that sequence which then provides a position marker. Alternatively, appropriate position markers may be placed into a target molecule, e.g. different position markers may be placed at regular intervals in a genome. To allow discrimination between the different position markers different signals are provided by those markers, e.g. they have different sequences or lengths which may be probed. Example 21 describes one method in which position markers are used.

Thus viewed in a preferred aspect the present invention provides a method of sequencing (completely or partially) a nucleic acid molecule comprising at least the steps of:

a) determining the sequence of a portion of said nucleic acid molecule;

b) determining the position of said portion within said nucleic acid molecule by reference to a positional indicator, preferably a position marker; and c) combining the information obtained in steps a) and b) to obtain the sequence of said molecule.

As mentioned previously, multiple sequences and their positions are preferably determined.

As used herein the positional indicator may as mentioned previously be the size of the molecule, the intensity of a generated signal or the distance to a positional marker, anchor or fingerprint.

A number of different techniques for performing these methods will now be described to illustrate the invention.

Every method for determining the size of polymers can be used, in principle. The length of the sequence pieces that are identified must, however, be adjusted to the precision of the size determination: the lower the precision, the longer the sequence pieces must be.

A number of methods for size sorting exist in the field; gel sorting, micro-capillary sorting, measuring of the lengths of polymers that are stretched out on a reading plate, measuring of the fluorescence intensity (or other) of polymers that are non-specifically tagged with the aid of a flow cytometer, fluorescence microscope, etc.), mass spectrometry, the time a polymer uses to block a micro or nanopore, etc. Such procedures may be conducted before or after the signal is read to determine the sequence, e.g. when gel electrophoresis is used, reading may be performed on samples separated on a gel or eluted from the gel.

The length of a nucleic acid molecule may also be determined based on the principle that the chance that a DNA molecule will be cleaved (e.g. by DNaseI, sonication etc) is proportional to the length of the DNA molecule. For example, a DNA molecule with 200 base pairs will be cut twice as often as one with 100 base pairs in a solution with a limiting amount of DNaseI. This could be achieved for example by end labelling different molecules, subjecting them to cleavage and then monitoring the amount of single and double labelled molecules relative to standards of known length similarly labelled.

In order to determine the length of a DNA molecule or the distance to a fixed point, the DNA molecule may conveniently be extended or stretched out. One method of stretching the DNA molecules is to mix them with a large surplus of small glass beads (they bind DNA molecules naturally) so that they bind the DNA molecules in a 1:1 ratio. The DNA molecules will have less resistance than the glass beads in the liquid flow so that they tend to move away from each other until the DNA molecule is stretched out. If the liquid flow is strong or the glass beads are large so that the difference in resistance between the DNA molecules and the glass beads is great, the DNA molecule may tear. However, this problem can be avoided by lowering the flow speed or by using smaller glass beads. The method becomes particularly efficient if the DNA molecules are arranged in a regular manner so that the amount of sequence information is increased per unit area. One way of doing this is to label the DNA molecules with biotin and then fix them to a plate with a regular streptavidin pattern. Alternatively fixing may be achieved using a laser beam, so-called laser trapping.

Instead of using a liquid flow to straighten out the DNA molecules, one can use a positive charge that pulls the negatively charged DNA molecules in one direction. Reading efficiency is likely to increase by using this strategy. The easiest method, in principle, is to place a positive or negative spot charge in front of the reading plate. According to Coulomb's law, the force of the charge on the DNA molecules is inversely proportional to the distance. The DNA molecules closest to the charge will then be stretched with a greater force than those that are further below. In order for all DNA molecules to be equally affected at the moment of reading, it will therefore be necessary to move the spot charge in step with the reading unit. The spot charge can also be placed far below the reading plate so that the force difference on the plate is reduced. As an alternative, it is possible to arrange the charge in an arc so that the force vectors are equally large in a straight line at the centre of the arc. Then the charge needs only to be moved when the reading unit is moved sideways.

Alternatively, to reduce the force on the molecule's anchor a different technique may be used. Two electrically charged plates may be placed under the reading plate on which the target molecules are to be stretched out. The top plate has a weak negative charge while the bottom plate has a relatively strong positive charge. If a negatively charged particle (e.g. DNA) is placed right above the negative plate, the repulsion forces from it will be greater than the attraction forces from the positive plate. The particle will then be forced upwards. However, moving away from the plate conditions will be reversed. The attraction force of the positive plate is greater than the repulsion force of the negative plate. By adjusting the charges of the plates, equilibrium will occur between repulsion and attraction forces at a given height above the reading plate. The target molecules will be pushed into this plane of equilibrium. In this method the net force on the DNA molecules is equal to zero as long as they remain in the plane of equilibrium. This reduces the chance of rupture.

In addition to the two charged plates a positive charge to the left of the reading plate may also be used. This will produce a net force in this direction. The same can be achieved by tilting the two charged plates in relation to each other and in relation to the reading plate.

If target molecules are to be moved while stretched through a flow cytometer or similar device, a negatively charged tube may be used. By using such a technique, target molecules will be pushed in towards the middle of the tube where the repulsion forces are the weakest.

A further alternative stretching technique is provided by mechanical stretching. In this method for example, two adjacent plates may be used in which oligonucleotides complementary to either end of the target molecules are attached. Once target molecules have been hybridized to these probes, the plates may be separated until the molecules are stretched between them.

The signal generated in the above described methods may be read in a number of different ways, depending on the signal which is generated and how positional information is to be obtained. For example to locate fluorescent DNA probes attached to a target DNA, the DNA may be stretched as described above. For example a method developed by Weier et al. (Hum. Mol. Gen., 1995, Vol. 4(10), p1903–1910) known as molecular combing may be used. In this method a solution with target DNA was placed on a flat glass surface prepared so that the DNA molecules attached themselves with one end to the glass plate. The DNA molecules were then straightened out by using a liquid flow. With the aid of a fluorescence microscope they could then observe the relative positions of the probes which were attached to the stretched DNA molecules.

In the present invention, by for example using four probes labelled with different fluorophores and magnifying tags which are unique stretches of DNA, the probes may be directed to those tags such that they hybridize to the four magnifying tags that represent A, C, G, and T, ie. using the DIRVISH techniques described previously. The sequence order may then be read directly with a fluorescence microscope. As mentioned previously, more or fewer probes may be used depending on how the magnifying tags are constructed, e.g. a single probe may be used in which the manner in which it binds to each magnifying tag produces a unique signal, e.g. the development of a binary code. Alternatively, more than 4 probes may be used where the magnifying tag corresponds to 2 or more bases. By developing software that causes the microscope to scan the glass plate while at the same time automatically analyzing the sequence order, it will be possible to read base pairs very rapidly.

As a further alternative, for fast reading a flow cytometer may be used to read the fluorescent probes. A prerequisite for this is that the DNA molecules pass the reading unit of a flow cytometer in a stretched form so that the magnifying tags that represent A, C, G, and T will pass in order. This may be performed by using the techniques described above. Alternatively for this particular embodiment, an electric or magnetic field may be used instead of liquid flow to pull the particles past the fluorescence detector. This can be achieved by utilizing the fact that the glass beads have a positive charge while the DNA molecules are negatively charged, or to use superparamagnetic beads instead of glass. The beads would then pull the DNA molecules behind them like long threads.

A critical parameter in this strategy is the lower fluorescence detection limits of the flow cytometer. Several groups have managed to detect individual fluorophore molecules by reducing flow speed. However, to use conventional flow cytometers with analysis speeds of 20–30,000 particles per second, longer probes must be used so that many fluorophores can be fixed to each probe.

The fastest flow cytometers currently have the capacity to analyze about 200,000 fluorescent particles per second, but these flow cytometers are not commercially available. In addition, it is not certain what the high-speed tolerance of DNA molecules is in stretched form before they break. However, it is realistic to assume that the DNA molecules will tolerate speeds that will allow extremely rapid reading.

A further alternative is to fix the DNA molecules in a regular fashion on a solid support, e.g. a streptavidin-covered plate. The sequence (e.g. the signals generated by a series of magnifying tags) is read by having small detectors inserted in the reading plate. These detectors are deactivated or activated by reporter molecules, e.g. on the magnifying tags, fixed to the fragments, e.g. by breaking or establishing electrical circuits by binding to sensors on a solid support. For example, strong bonds may be formed between the reporter molecules and modules on the reading plate. In the latter case the modules may be shaped in such a way that they can be torn loose from the reading plate if the DNA molecules are torn away. When the modules come loose, they break the current circuit in a way that registers what modules have been removed from the reading plate. In order to increase the chance of a successful binding, several reporter molecules may be fixed in the same position on the fragment. One could either use four different reporter molecules for each of the bases A, C, G, and T, or use the same reporter molecule positioned on four different places on the fragments. With multiplex, parallel computer inputs and other modern electronics, it is believed to be possible to register several million signals per second allowing rapid sequencing.

In a preferred embodiment these methods are appropriately used in conjunction with the magnifying techniques described herein, ie. a portion of said target nucleic acid molecule is determined by the presence of one or more, preferably a chain of magnifying tags. These methods may however also be used when no magnification is performed. Instead of magnifying the DNA molecules, one could incorporate different attachments to the bases that the sensors can register.

Once the signal information has been accumulated, a computer program is used to assemble the sequence pieces into the final sequence. The probability that errors will occur in this step depends primarily on five parameters: the length of the DNA molecule that is to be sequenced, how randomized the base pair composition of the DNA sequence is, the length of the DNA pieces that are to be read, the number of DNA pieces that are being read, and the error rate in the sequencing reactions.

The inventor has already created a computer program to analyze the importance of the above-mentioned parameters. Based on human genome DNA that has already been sequenced, the analyses show that with a DNA piece length of 30 fragments, reading of $6 \times 10^8$ DNA pieces, and an error rate in the sequencing reaction of 10% (considering spot mutations), a human genome could be read in a single sequence reaction and with very few spot mutations/deletions. However, one exception is very non-randomized areas (satellite DNA and other repetitive areas) where the DNA piece lengths must be increased. The biological information in these areas, however, is of subordinate importance compared to coding sequences and cis-regulatory elements.

Data analyses also show that even a very high error rate in the sequencing reaction is compensated for when the DNA pieces are read many times. For example, by reading ten times as many base pairs as the length of the sequence, most deletions and spot mutations will be eliminated even with a high error rate in the sequencing reaction.

Depending on the technique which is used for sequencing it is in certain circumstances possible to perform sequencing on a heterogeneous sample, e.g. to perform parallel sequencing. Procedures which allow this form preferred aspects of the invention. Such techniques requires that signals from different target molecules may be discriminated. This may be achieved in a number of ways, e.g. by restriction to particular locations, inclusion, or identification, of markers which identify particular target molecules etc. For example, solid supports which complement a region of a target nucleic acid molecule may be used to isolate and retain a particular molecule. This may be performed with knowledge of at least a part of a sequence, ie. to bind particular molecules to a particular site, or without such knowledge using essentially random binding probes on which different molecules will bind and which may then be sequenced in parallel, by making use of one or more techniques to relate the sequence to that molecule, e.g. by address or positional marker. The techniques described herein are particularly advantageous since they allow individual molecules to be sequenced thus further aiding the facilitation of parallel sequencing reactions.

A number of the techniques described herein may be used for sequencing only a part of a target molecule or for fingerprinting, profile analyses or mapping, ie. identifying discrete and distinctive portions of a molecule, e.g. for analysis of RNA expression (which may first be converted to cDNA for analysis). For example, as described in Example 23, a target sample may be digested with a restriction enzyme which produces a particular overhang to which a magnifying tag (preferably a chain of magnifying tags) may be attached. In addition to carrying sequence related information, such tags may additionally carry information relating to the enzyme which resulted in cleavage, ie. as a marker of fragments resulting from that cleavage. More than one restriction enzymes may be used simultaneously if these produce different length overhangs to which different adapters may be bound. Alternatively different restriction enzymes may be used in consecutive cycles.

The resultant fragments may then be aligned for example by virtue of the amplifying tags attached to complementary overhangs, e.g. by the use of tags which reflect this complementarity, e.g. wherein the tags themselves are made up of nucleotide bases. From this a restriction map may be built up as described in Example 23. Thus in a further aspect the present invention provides a method of producing a map of a target sequence comprising obtaining sequence information on discrete portions of said sequence as described herein in addition to positional information on said portions as described herein.

In a preferred feature said map is produced by obtaining sequence information on discrete portions of said sequence wherein said portions comprise all or part of the cleavage sites of one or more nucleases and/or all or part of the restriction sites of said nucleases and the positions of said sequences are determined by comparison of the sequences at the terminal ends of fragments of said target nucleic acid molecule after digestion with said nucleases.

Preferably sequence information is obtained by cleavage of said target molecule by one or more nucleases as described herein, preferably to produce complementary single stranded regions, and binding of an adapter molecule to a region of said target molecule (preferably at, or adjacent to the cleavage site) wherein said adapter molecule carries one or more magnifying tags as described herein wherein said tag comprises a signalling moiety which corresponds to one or more bases of said region to which said adapter molecule binds and additionally comprises a further signalling moiety which corresponds to the nuclease used for cleavage. In instances in which sufficient nucleases are employed, this method may be used as a method of sequencing.

For example, a bacterium may be identified in the following manner. Bacteria may be lysed and the DNA isolated. The molecules may then be cut with a class II restriction endonucleases or other such nucleases as described herein. The DNA molecules may then be bound to adapters to identify the overhangs. The DNA molecules may then be fixed to a reading plate and stretched. By scanning the reading plate with a fluorescence scanner information or characteristic pattern may be obtained on restriction lengths and sequence information derived from the ends of those molecules. Techniques in which such magnification is involved allows the discrimination of molecules of the same size by virtue of their end sequences. Thus in a further feature of the invention, the present invention provides a method of obtaining a fingerprint of a target DNA molecule comprising the use of one or more of the sequencing techniques described herein in addition to obtaining positional information as described herein.

In preferred features of the invention, positional information is obtained by reference to a characteristic restriction map of said target molecule. Further preferred features include the use of restriction mapping to identify one or more magnifying tags and the use of tags which may effectively be read using flow cytometers or nano/micro pore analysis.

Using the principles and protocols that are introduced in this patent application error rates can be reduced by using proofreading techniques both in the sequencing/sorting reactions and when reading the signals.

If sorting is used, it is possible to sort the same piece of sequence several times. For example, all target DNA that begin with AAAA (SEQ ID NO:1) are sorted into well 1. Then the same procedure is repeated where incorrectly sorted DNA molecules that do not end with AAAA (SEQ ID NO:1) are washed away. The procedure can in principle be repeated until the desired error percentage is obtained.

If magnification/conversion is used, it is possible to convert the same piece of sequence on a target molecule several times so that a repetitive chain of magnifying tags (signal chain) is obtained. Most error conversions can then be discovered when the repeated conversion products are not alike. The portion of a target molecule that is to be used to derive position information can also be copied in the same manner.

In addition, each sequence piece may be read many times because the number of target molecules that are analyzed can be very great.

Kits for performing the sequencing or magnification methods described herein form a preferred aspect of the invention. Thus viewed from a further aspect the present invention provides a kit for magnifying one or more bases of a target nucleic acid molecule comprising at least one or more adapters as described hereinbefore, optionally attached to one or more solid supports, preferably comprising one or magnifying tags themselves comprising a signalling means.

Optionally the kit may contain other appropriate components selected from the list including restriction enzymes for use in the reaction, vectors into which the target molecules may be ligated, ligases, enzymes necessary for inactivation and activation of restriction or ligation sites, primers for amplification and/or appropriate enzymes, buffers and solutions. Kits for carrying out other aspects of the sequencing reactions described herein are also included within the scope of the invention. Thus for example kits for performing the sorting reaction may comprise at least a solid support carrying one or more complementary probes, preferably a series of discrete probes mismatched to each other probe at a different address on the solid support, or on a separate solid support, by one or more bases. Appropriate labelling means may also be included in such kits.

The use of such kits for magnifying target nucleic acid molecules or for sequencing form further aspects of the invention.

The following examples are given by way of illustration only in which the Figures referred to are as follows:

FIG. 2 shows a method of introducing magnifying tags into a target sequence using a vector carrying 2 restriction sites both of which result in overhangs and adapters which also contain such restriction sites.

FIG. 3 shows a method of sequencing nine bases per cycle with a proofreading mechanism, FIG. 3A shows the adapters which are used and FIG. 3B shows the enzymatic steps used to magnify each base;

FIG. 6 shows a method of sequencing using adapters which function as primers when binding to single stranded target molecules in which A) shows the adapters which are used as primers to bind to the target molecules and B) shows an adapter bound to a target molecule;

Figure 13A:
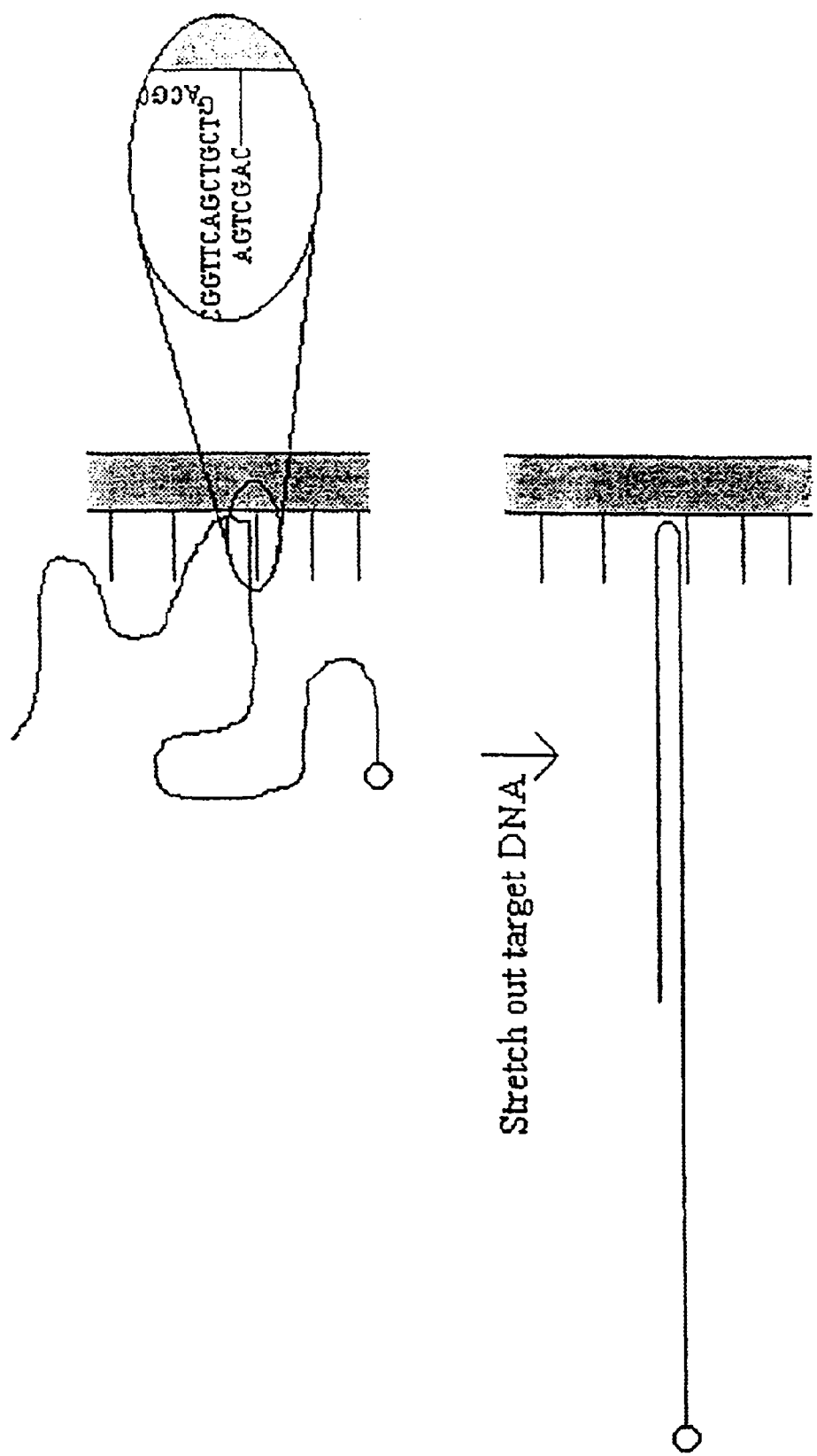
Figure 13B:
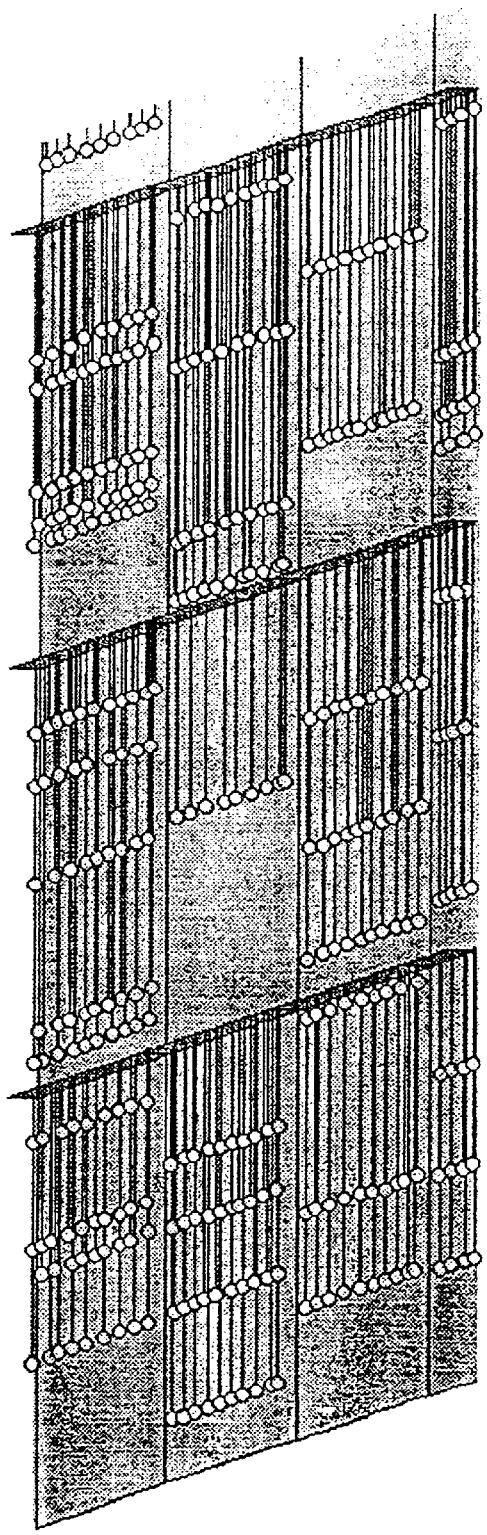
Figure 14A:
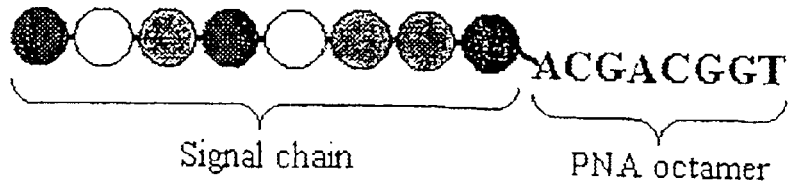
Figure 14B:
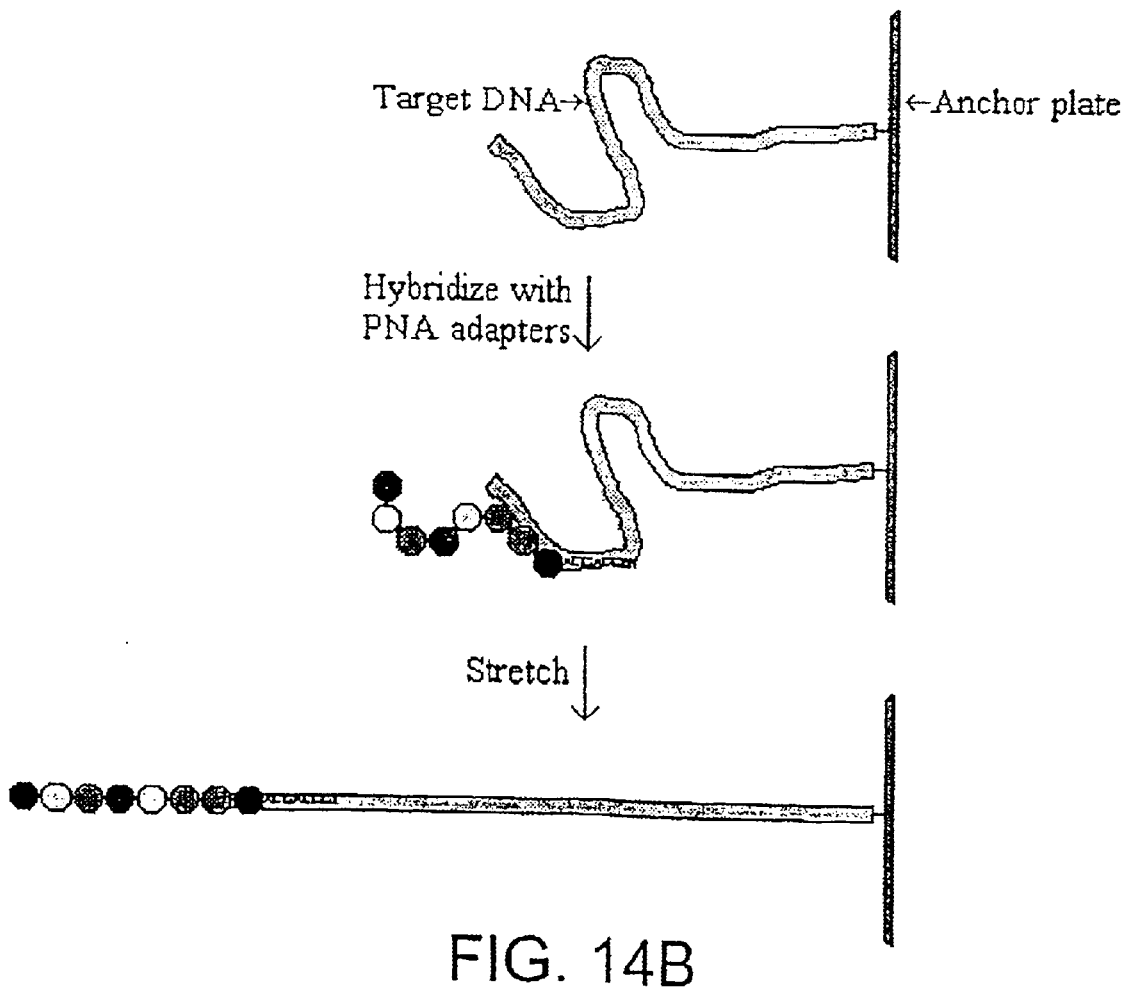
Figure 14C:
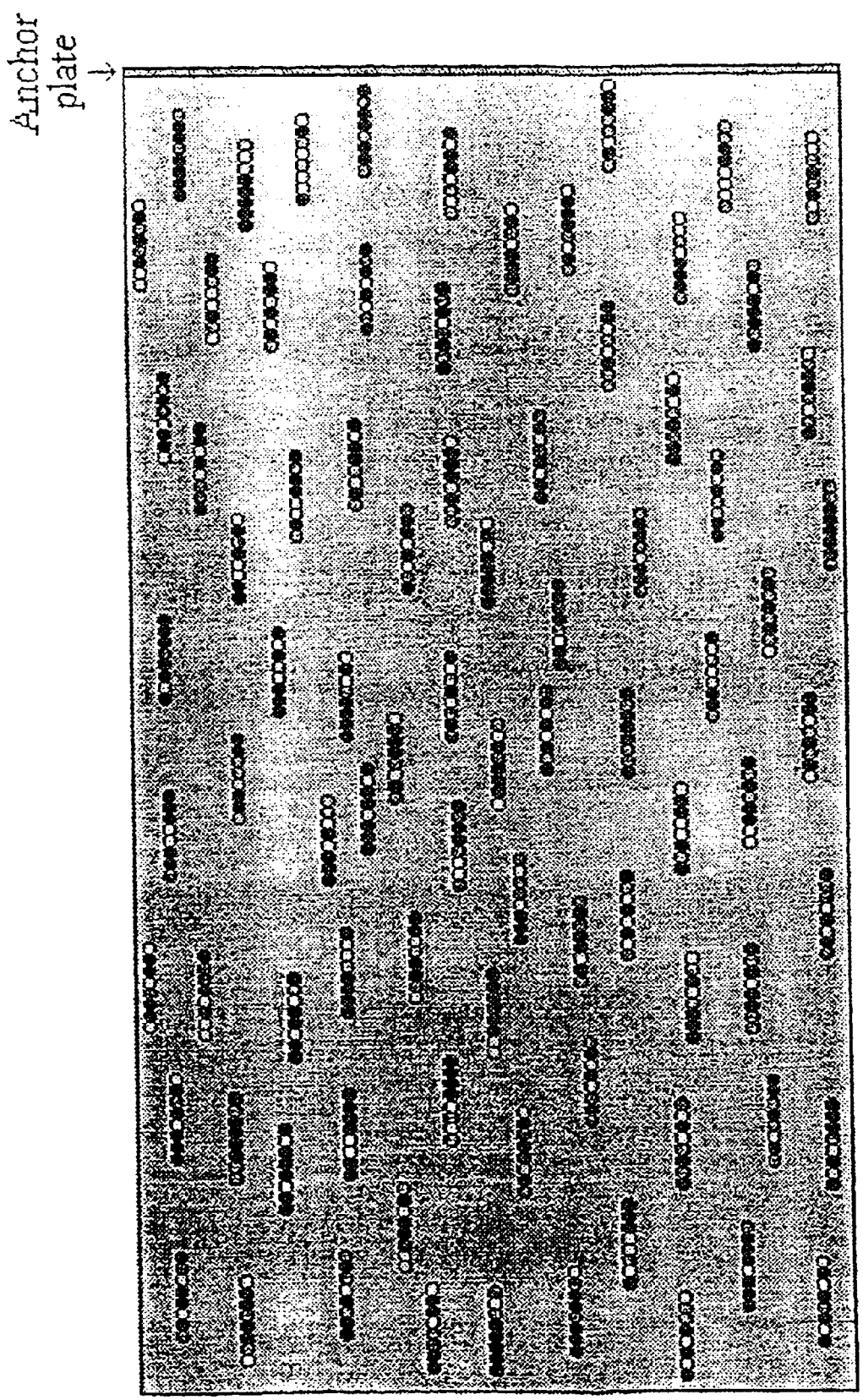
Figure 15:
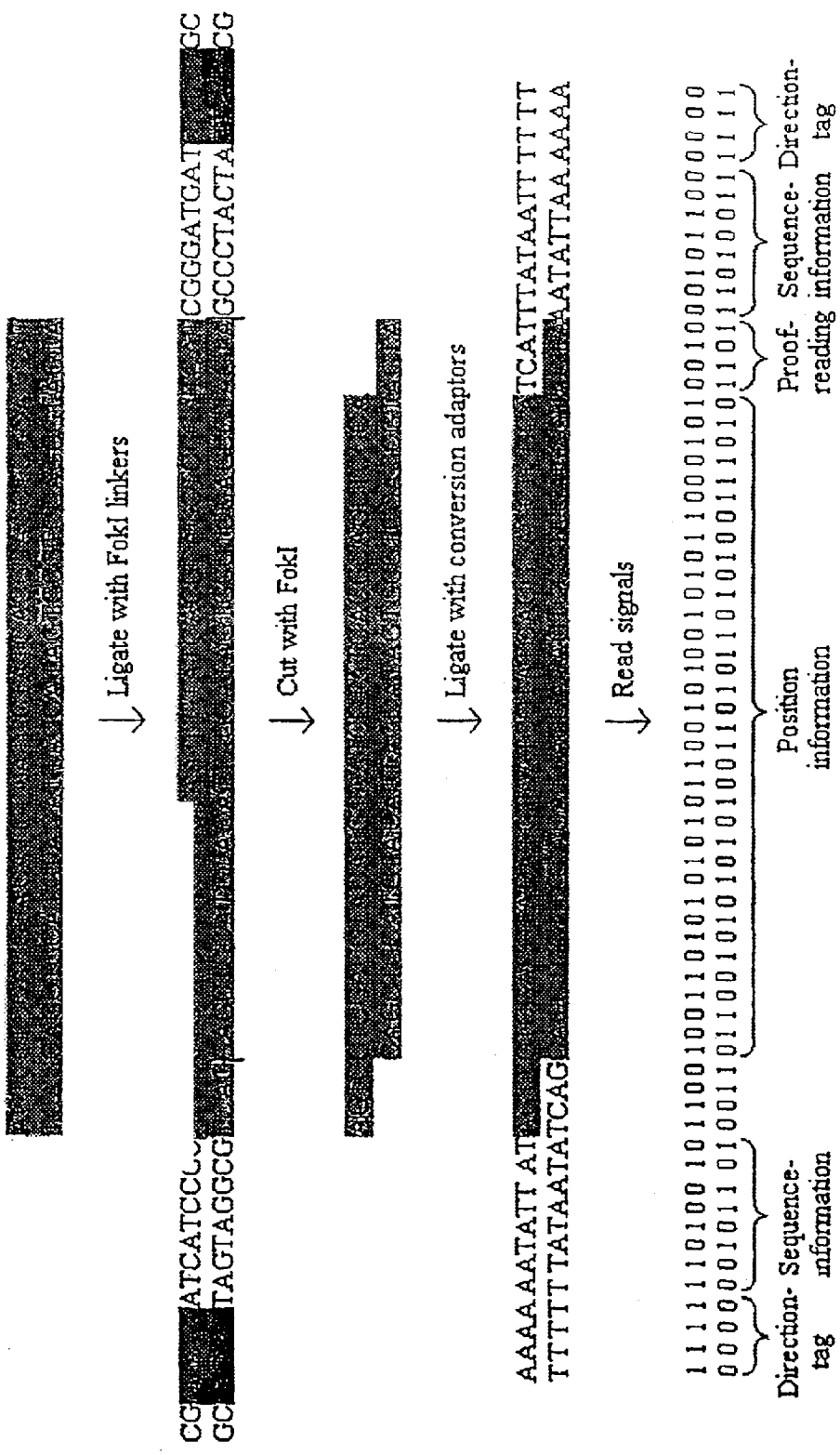
Figure 16A:
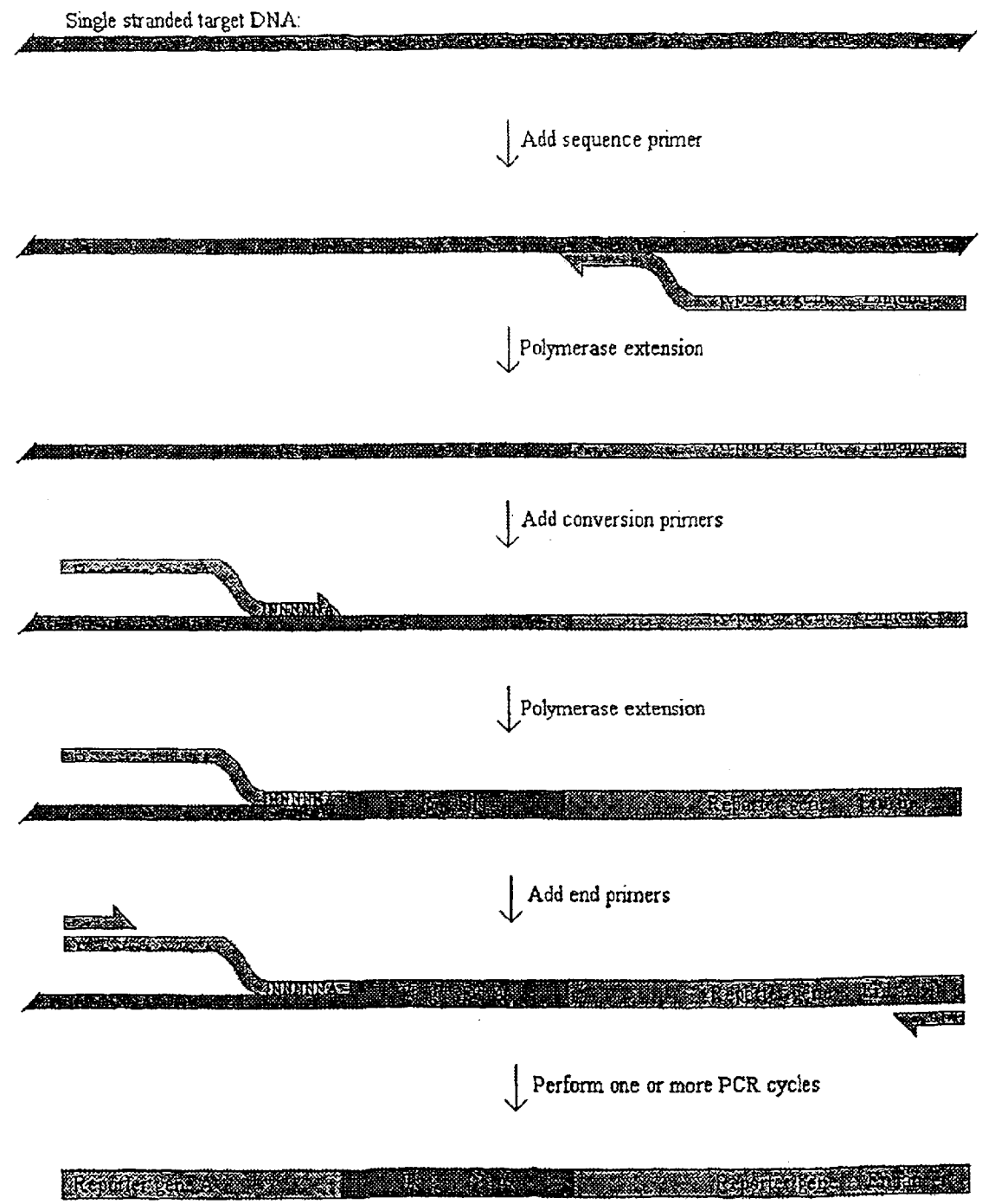
Figure 17:
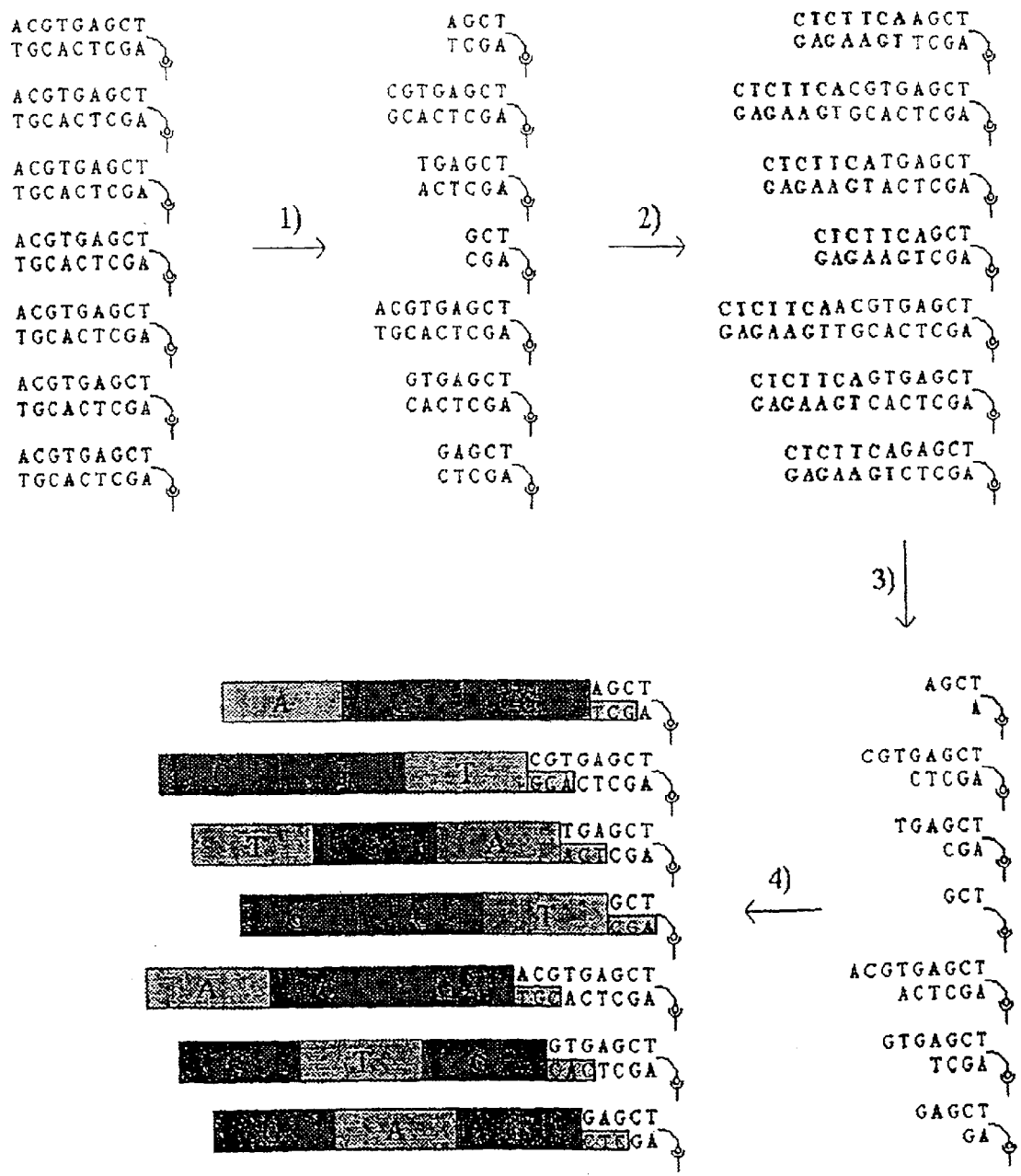
Figure 19:
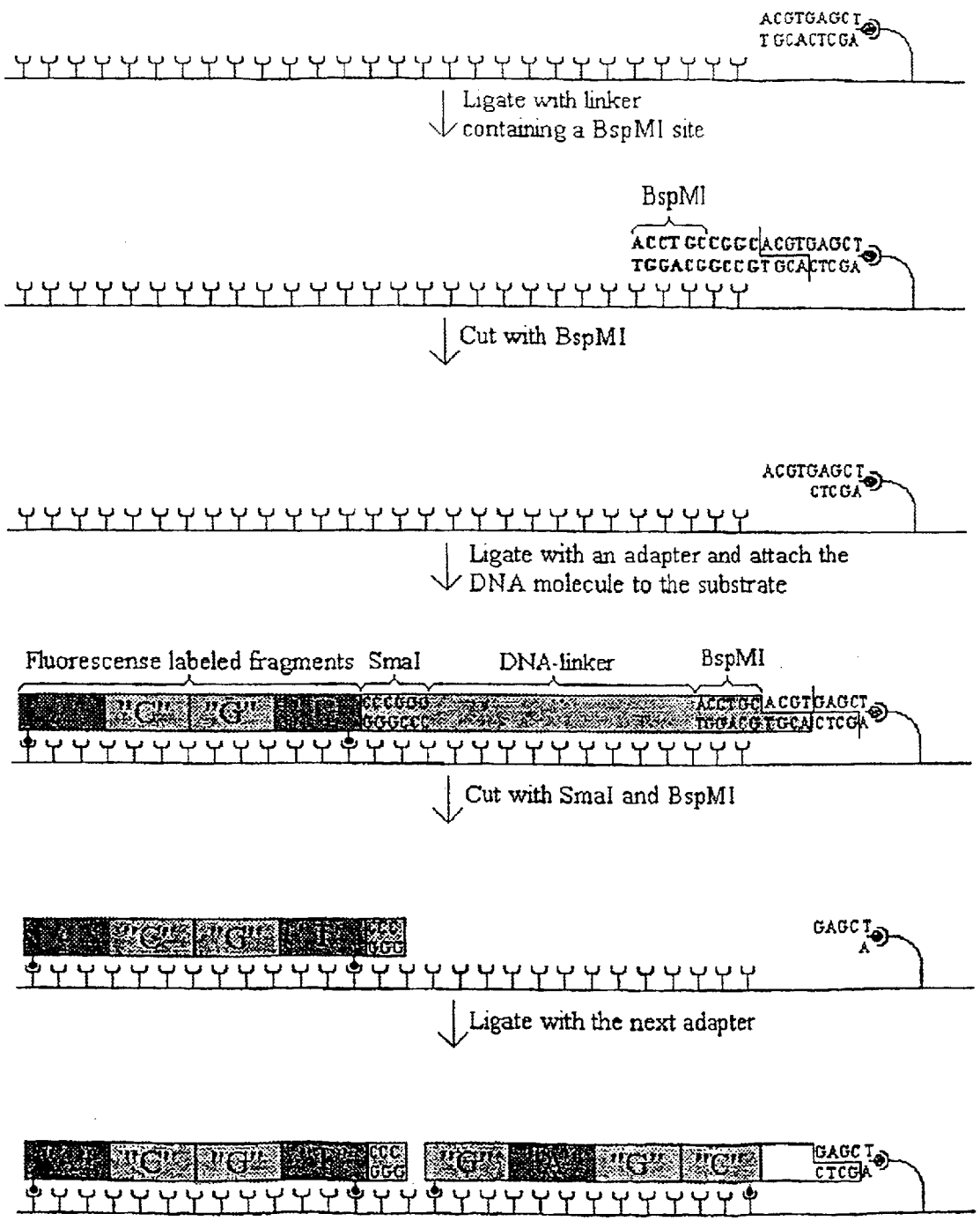
Figure 20:
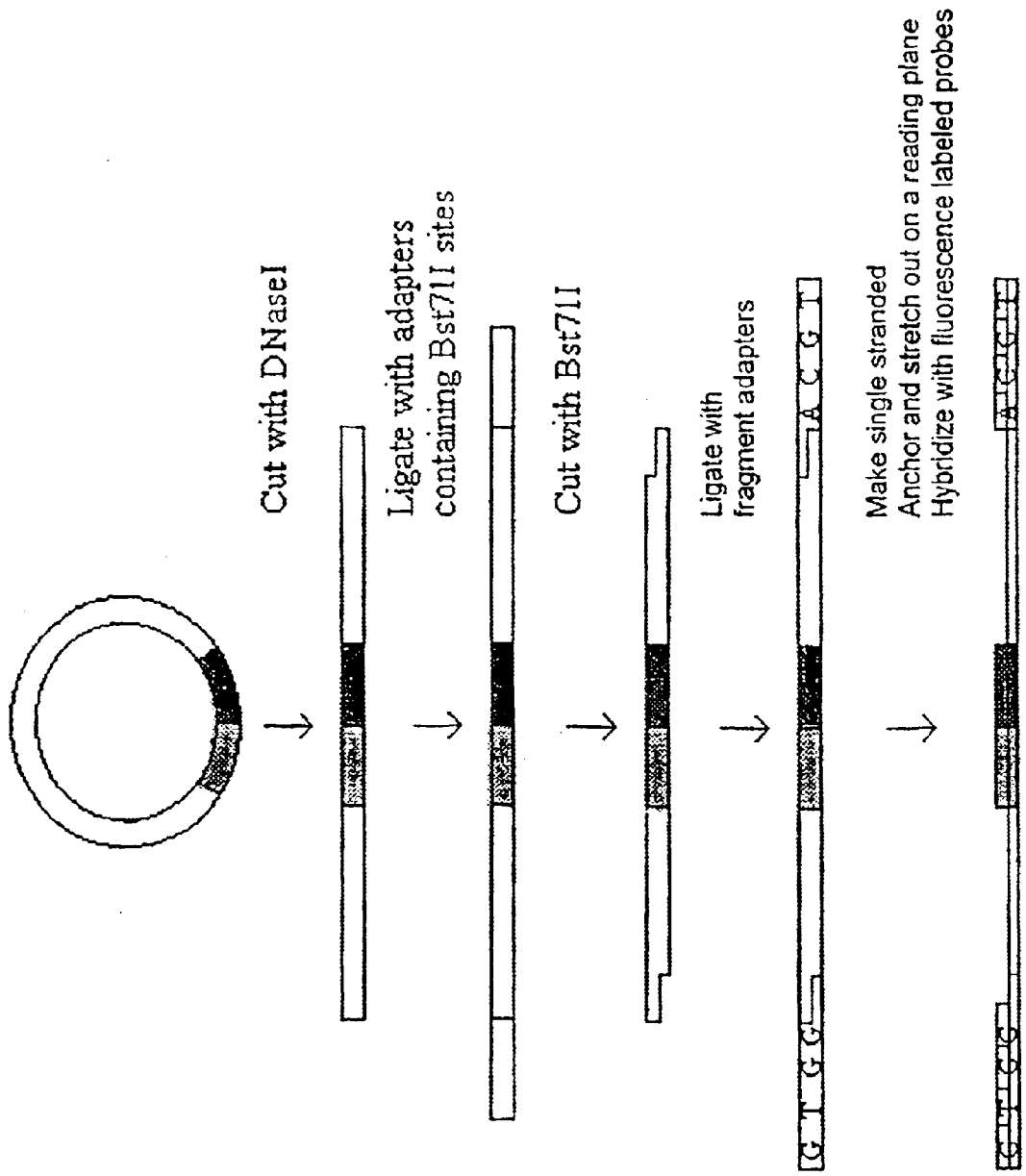
Figure 21:
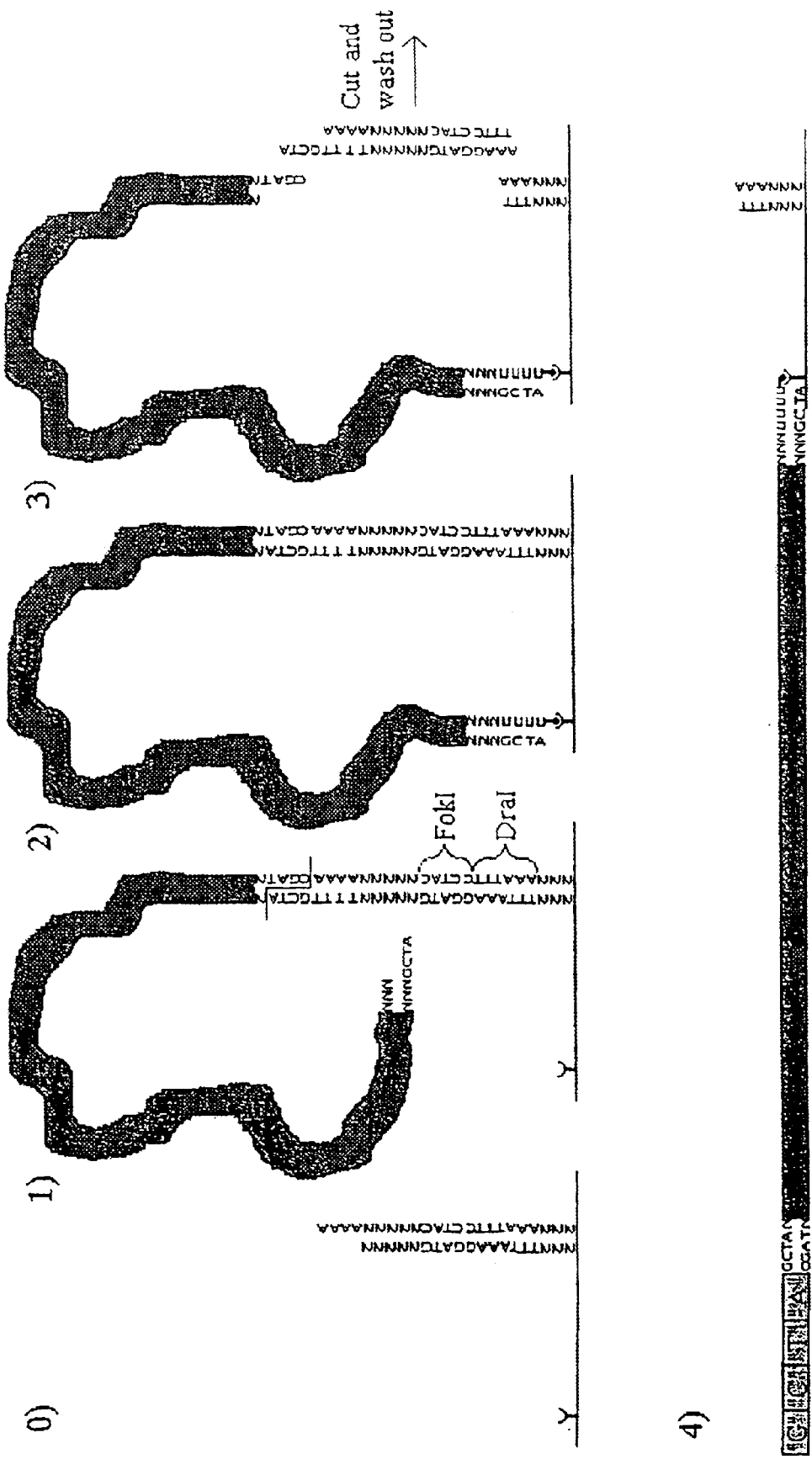
Figure 22:
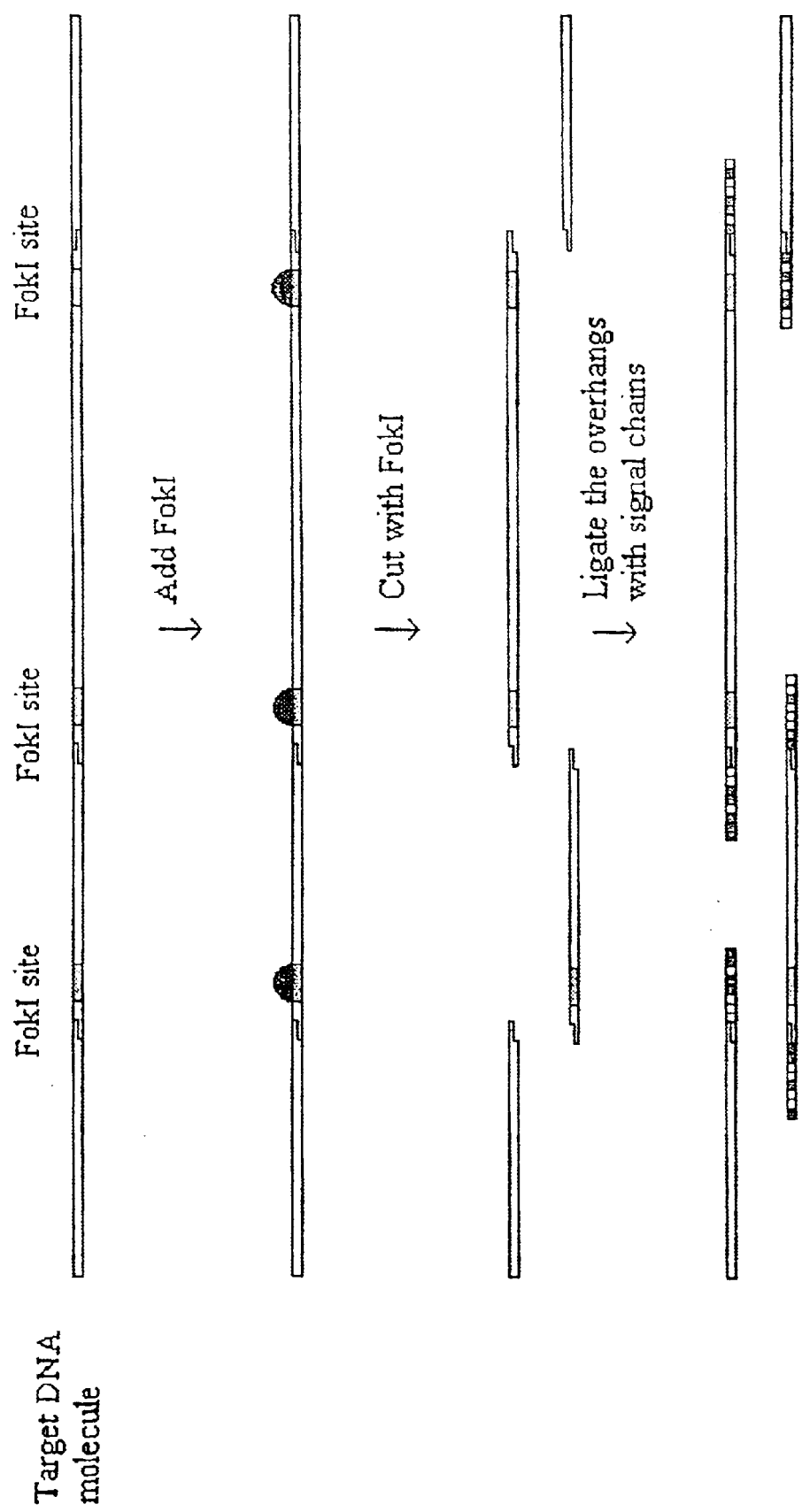
Figure 23:
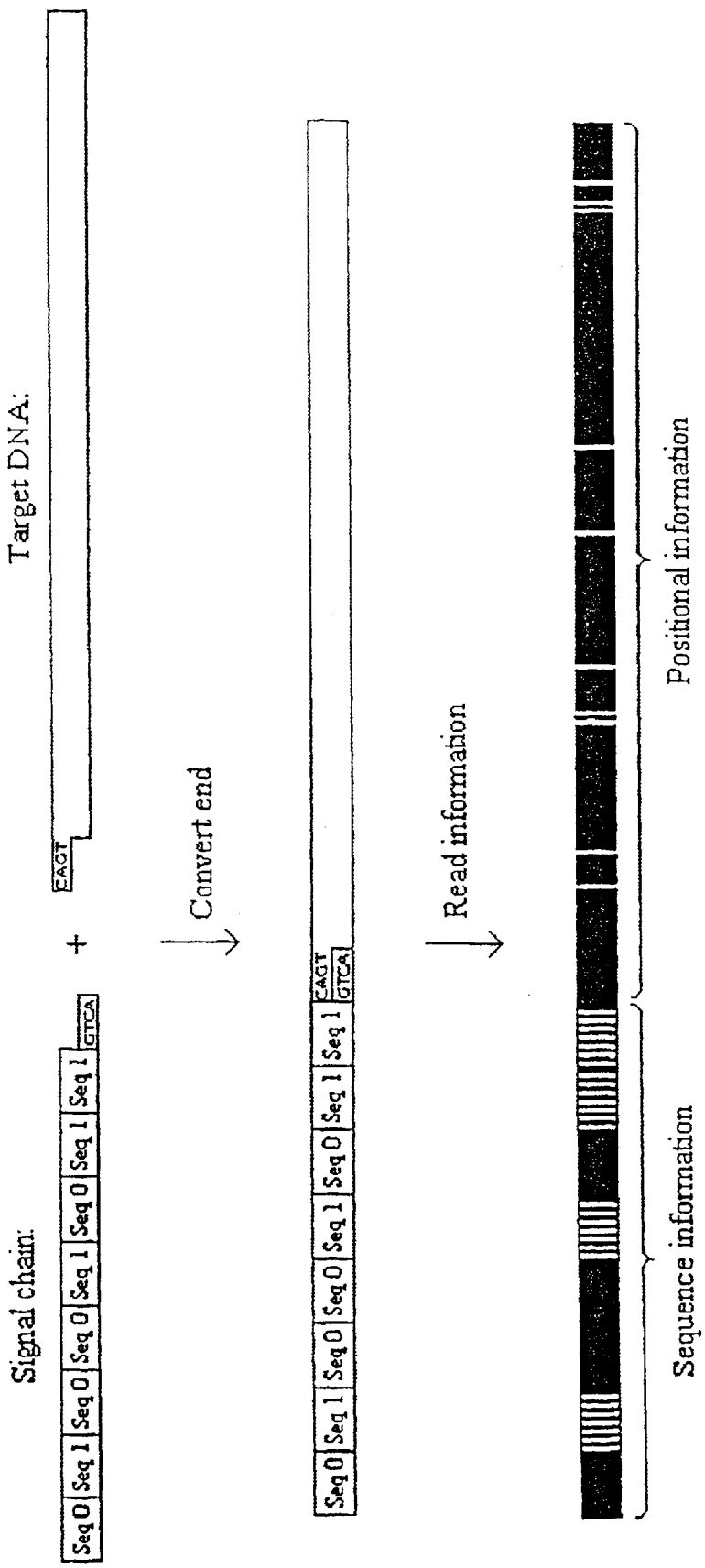
Figure 24:
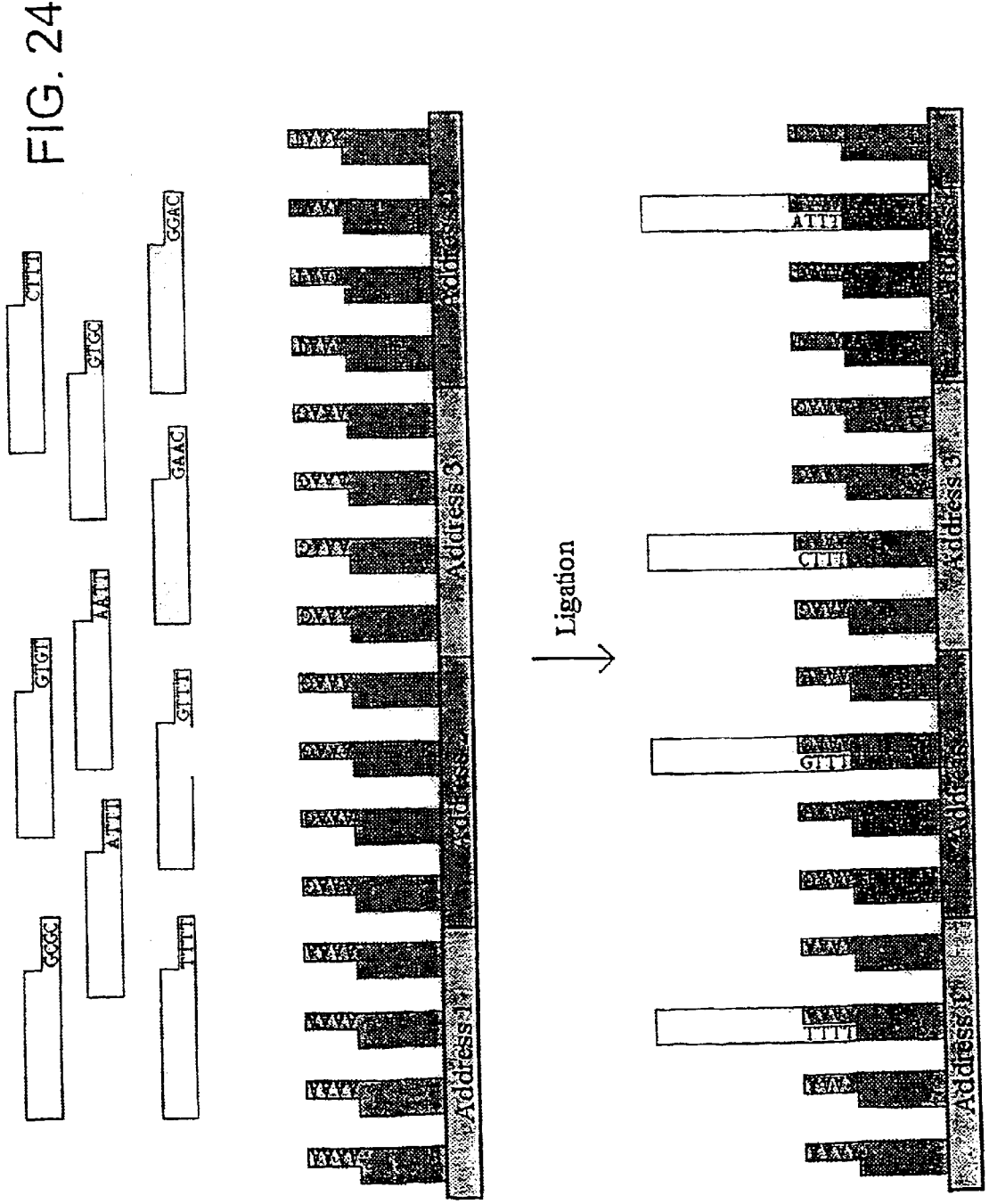
Figure 25:
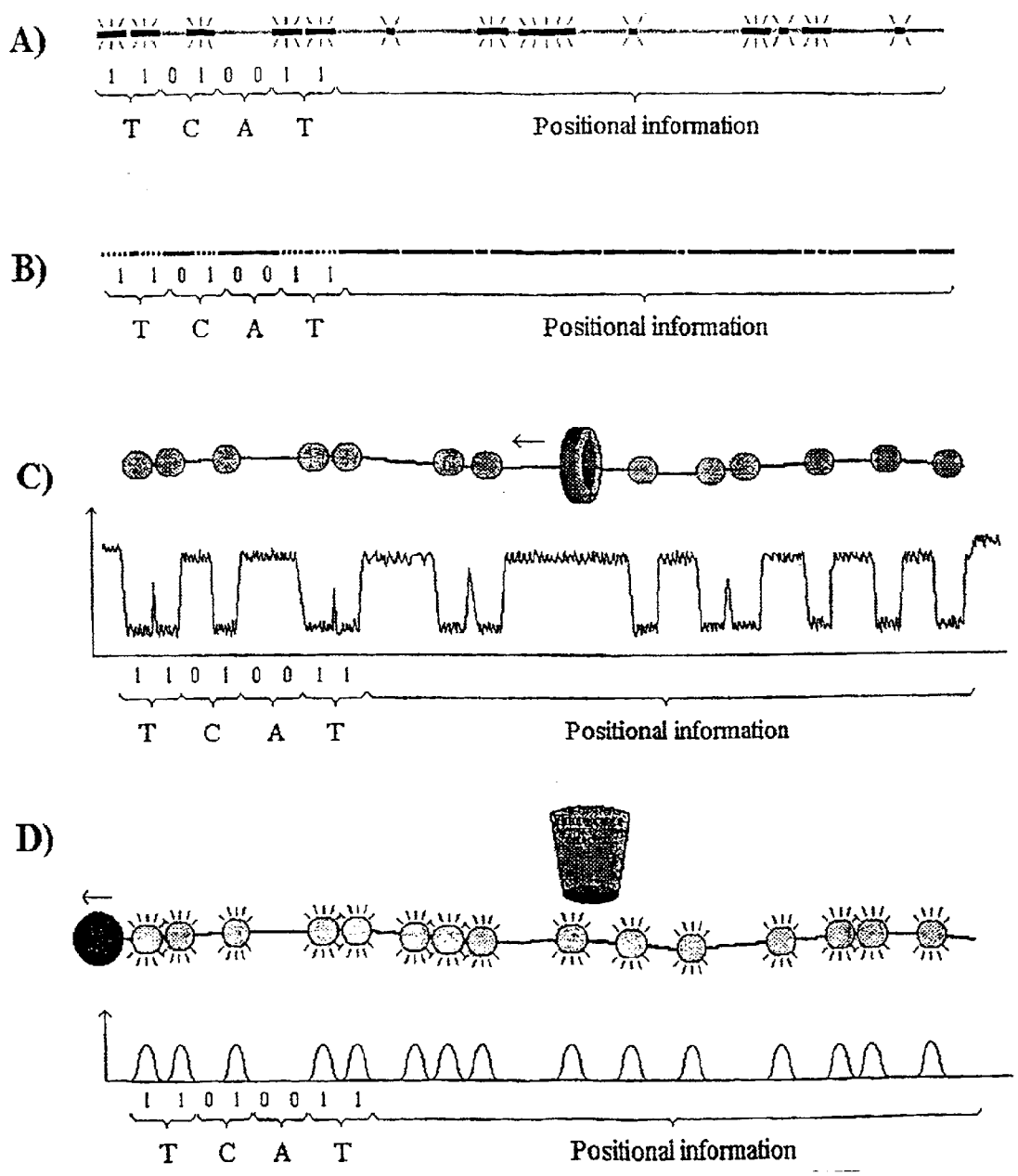

FIG. 12 shows a method for DNA sequencing using a primer-based sorting strategy, in which A) illustrates the general procedure in which a sequencing primer is bound to a solid support (step 1), to which the target molecules are bound (step 2) and extended by polymerase extension (step 3), primers carrying different signals are then bound (step 4) and the chains extended (step 5), the resultant extension products are then released for sorting (step 6); B) shows representative primers for use in well 1 which have different signals attached; and C) shows the fluorescence information which is obtained for each of the 16 wells;

FIG. 13 shows the procedure for DNA sequencing using a sorting strategy based on hybridisation and the results which are obtained, in which A) shows the binding of single stranded fluorescent labelled target molecules to octamer probes on a solid surface with multiple addresses which are then stretched; B) shows a section from a scanning surface which illustrates how the fluorescence signals are distributed in straight lines corresponding to the different lengths at each address; and C) shows the intensity of the fluorescence at one address;

FIG. 14 shows a method of DNA sequencing in which the target DNA molecules are attached to a fixed reference point, in which A) shows the conversion adapters consisting of PNA and a chain of magnifying tags (identified herein as the signal chain) with a corresponding composition; B) illustrates the binding of target DNA to the solid support, attachment with the PNA adapters and stretching; C) shows the appearance of the scanning surface after the molecules have been stretched;

FIG. 15 shows the method of binary end conversion before nanopore sequencing in which the procedure to produce target molecule containing conversion adapters is shown as well as the resultant signal consisting of position and sequence information as well as direction tags;

FIG. 16 shows how cells are used to generate a signal reflecting a base sequence, in which A) shows how an enhancer is added to the target molecules and thereafter primers are attached which carry magnifying tags in the form of reporter genes; and B) shows a histogram illustrating the signal distribution;

FIG. 17 shows a method of sequencing by creating sequencing ladders differing by three magnified bases each in which bound target molecules are cleaved non-specifically, bound to adapters which are cleaved to generate overhangs to which magnifying tags are attached;

FIG. 18 shows a method of sequencing by creating fixing points along the length of a DNA molecule which are attached to a solid support and the ends of the fragmented DNA are magnified;

FIG. 19 shows a method of sequencing in which strings of magnified tags are sequentially adhered to a solid support in which adapters are used which contain a DNA linker which spaces the signal from the DNA being sequenced, which may be removed to allow access to the molecule being sequenced in the next cycle;

FIG. 20 shows a method of introducing position markers into a molecule containing a fragment to be sequenced which is sequenced with the aid of adapters;

FIG. 21 shows a method of sorting in which a target molecule is bound to adapters present on a solid support. The terminal end of the molecule is then bound to the solid support and the other end released to allow conversion of an adjacent strand of DNA. (4) shows the resultant DNA after stretching;

FIG. 22 shows a method of preparing target molecules for mapping procedures in which several restriction enzymes are used that produce overhangs differing in both length and orientation (3' or 5' overhangs) which are then ligated to chains of magnifying tags;

FIG. 23 shows the general principle of magnification in which the four outermost bases of a target DNA molecule are magnified by a ligation reaction with a chain of magnifying tags. The part of the target DNA molecule that is not magnified may be used to obtain position information as shown, in this case by reading with an optical mapping based strategy;

FIG. 24 shows the sorting method described herein which is performed on a microarray in which overhangs of 4 bases in the target DNA are mixed with a microarray with 256 addresses and ligated. Address 1 contain AAAA (SEQ ID NO:1) overhangs and thus binds to target molecules with TTTT (SEQ ID NO:2) overhangs;

FIG. 25 shows examples of how signal chains may be used to obtain both sequence information (left) and positional information (right) in which A) shows a DIRVISH based method using fluorescence labelled probes that bind the target molecules in a characteristic pattern, B) shows an optical mapping based method in which the restriction pattern is used to give the position of the sequence, C) shows a method in which a characteristic pattern of DNA binding proteins are registered as they pass through a micro/nanopore and D) shows a method using fluorescence labelled probes, proteins or the like which are registered as they pass a fluorescence detector.

EXAMPLE 1

Sequencing by the Introduction of Magnifying Tags by Using Two Restriction Enzymes, One Creating an Overhang and the Other Creating Blunt Ends Methods 1. A pure DNA population consisting of the DNA sequence that is to be sequenced is cut/broken in a non-specific manner so that a population of DNA molecules is formed that consists of pieces (hereafter called DNA pieces) of the original sequence.
2. Base pairs in the DNA pieces are replaced with four different DNA sequences (hereafter called DNA fragments corresponding to the magnifying tags) that represent each of the four bases Adenine, Cytosine, Guanine, and Thymine. Thus, where there was an A-T base pair "fragment A" is inserted, C-G is replaced by "fragment C", etc. Thereby new DNA molecules are generated where the original base order of e.g. ACGTT (SEQ ID NO:3) is replaced by fragment A—fragment C—fragment G, etc. The length of these four DNA fragments can, in principle, vary from two base pairs to several hundred kbp (or more if desired), according to requirements. Correspondingly, the DNA fragments can contain reporter genes and other biological information or consist only of sequences without a known biological function.
3. The order of the four types of DNA fragments for each individual DNA molecule is read. Thereby, the base order of the original DNA pieces is determined.
4. A computer program utilizes the overlaps between the DNA pieces to put together information from Step 3 for the sequence of the DNA sequences that were used at the starting point.

Figure 1:
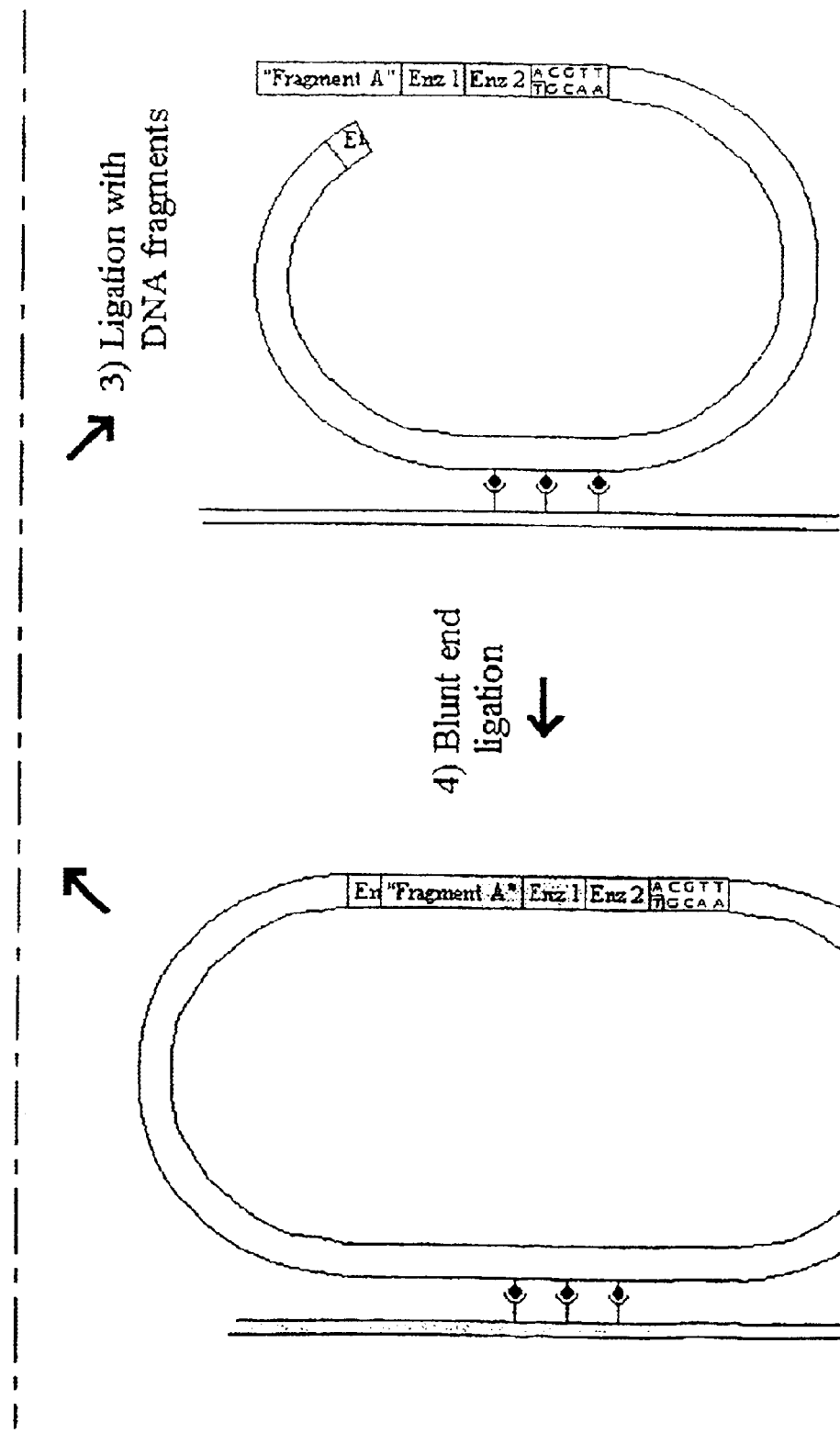
FIG. 1 shows a method of introducing magnifying tags into a target sequence using two restriction enzymes, hybridization and ligation.

FIG. 1 illustrates one method of performing step 2 that is based on restriction enzymes that cut outside their own DNA binding site. The method is performed as follows:

1) DNA pieces from Step 1 are ligated into a plasmid that has binding sites for a restriction enzyme (Enz1) that generates blunt end cuts and that cuts outside of its own DNA binding site and generates one base pair overhangs (Enz2). In addition, biotin bases are incorporated into the plasmid so that it sticks to the streptavidin treated reagent tube where the reaction takes place.
2) The reagent tube is washed and a new reaction mix containing Enz1 and Enz2 is added and incubated so that one blunt end and one end where the first base of the DNA piece constitutes an overhang are formed.
3) The reagent tube is washed again and a reaction mix containing four different DNA fragments together with a thermostable DNA ligase (e.g. Pfu or Taq DNA ligase) is added and incubated. The advantage of thermostable DNA ligases is that they ligate very specifically, while at the same time they do not ligate blunt ends. Thereby "fragment A" will be ligated where there is an adenosine overhang, "fragment C" where there is a cytosine, etc.
4) The reagent tube is washed yet another time and a reaction mix with T4 ligase is added and incubated so that the blunt ends are ligated. Since the inserted fragments have sites for Enz1 and Enz2 as the plasmid did originally, we are back at the starting point so that the next base can be replaced by a DNA fragment in a new cycle.

EXAMPLE 2

Figure 2A:
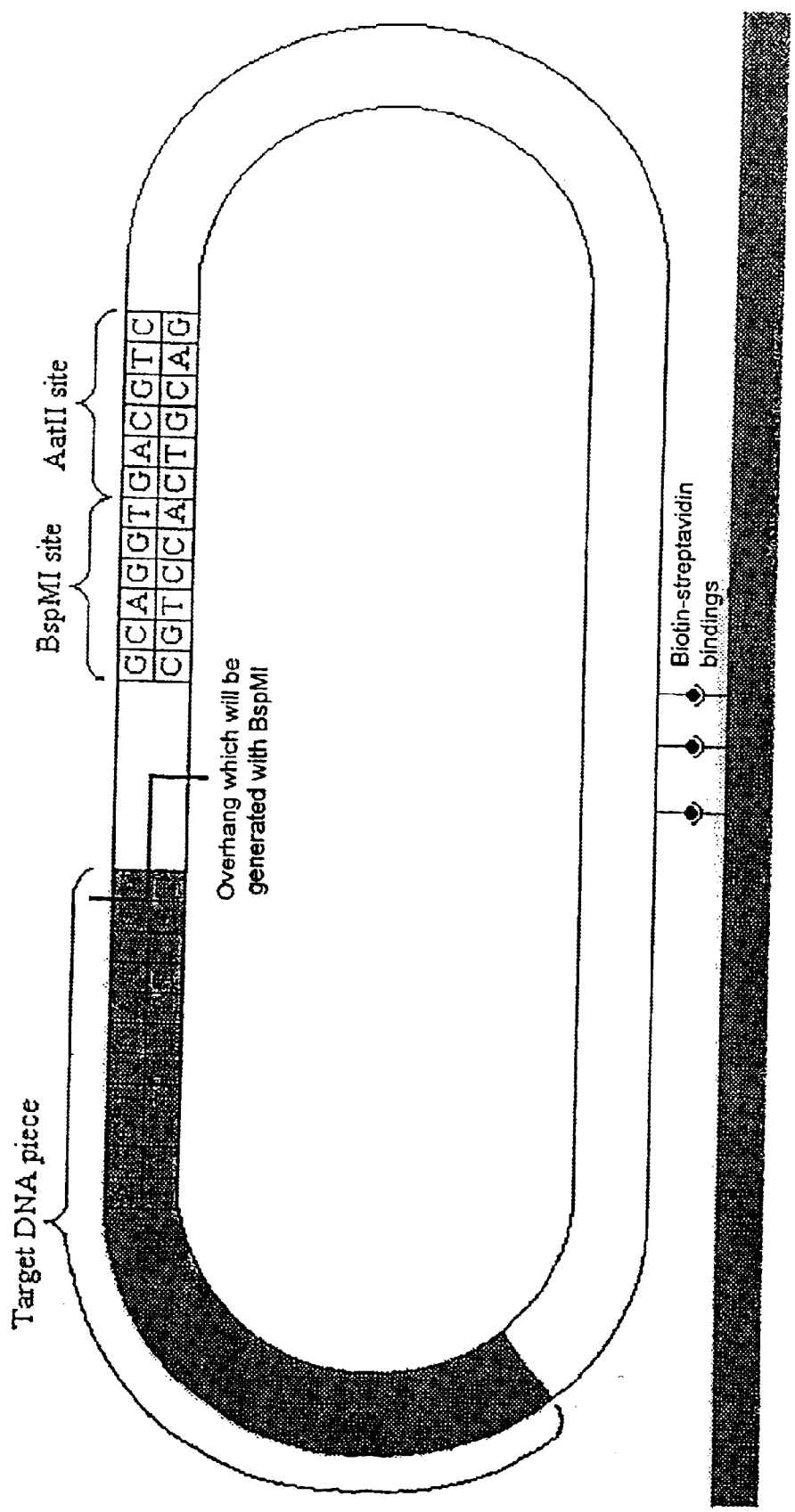
FIG. 2A shows the base vector including the target DNA.

Sequencing by the Introduction of Magnifying Tags by Using Two Restriction Enzymes, Both Creating Overhangs The starting point for the method is that all target DNA fragments that are to be converted are treated with BspMI-methylase so that all BspMI sites become inactive. They are then ligated into the base-vector as illustrated in FIG. 2a which shows the base vector with a DNA piece ligated into it and fixed to a streptavidin substrate. The base vector contains a BspMI site that is used to cleave the DNA fragment as shown with the solid line. The overhang that is created in this example will have a <T> on the inside so that it is only the A adapters that can be ligated to the overhang. The AatII site is used to circularize the base vector after adapter A has been ligated to the overhang that was created with BspMI. The base vector also contains bases tagged with biotin so that it can be fixed to a streptavidin-covered substrate.

Figure 2B:
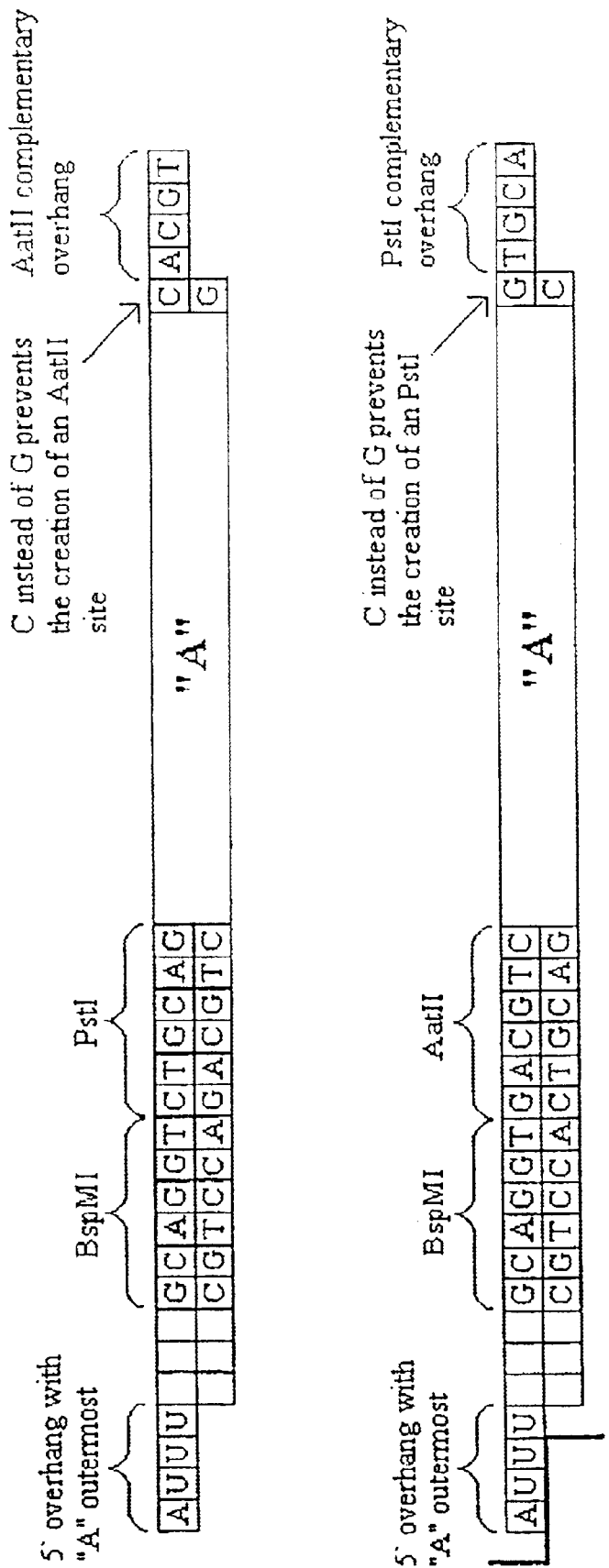
FIG. 2B shows the adapters which may be used and FIG. 2C shows the four enzymatic steps used to magnify each base.

The adapters which are used are shown in FIG. 2b. The only difference between Adapter A1 (top) and A2 (bottom) is that the AatII site/overhang has changed places with the PstI site/overhang. The A1 and A2 adapters will be used in every second cycle so that A1 is used in cycles 1, 3, 5, etc. while A2 is used in cycles 2, 4, 6, etc. The 5' overhang consists of three universal nucleotides plus adenine along 5'. These overhangs will thereby ligate to other 5' overhangs with a thymine on the inside of the overhang (along 3'). The thick line outside the 5' overhang on the bottom adapter shows the overhang that will be created by cleaving with BspMI after the adapter has been ligated to a DNA fragment. In addition to the A adapters, adapters must be made for C, G, and T.

Figure 2C:
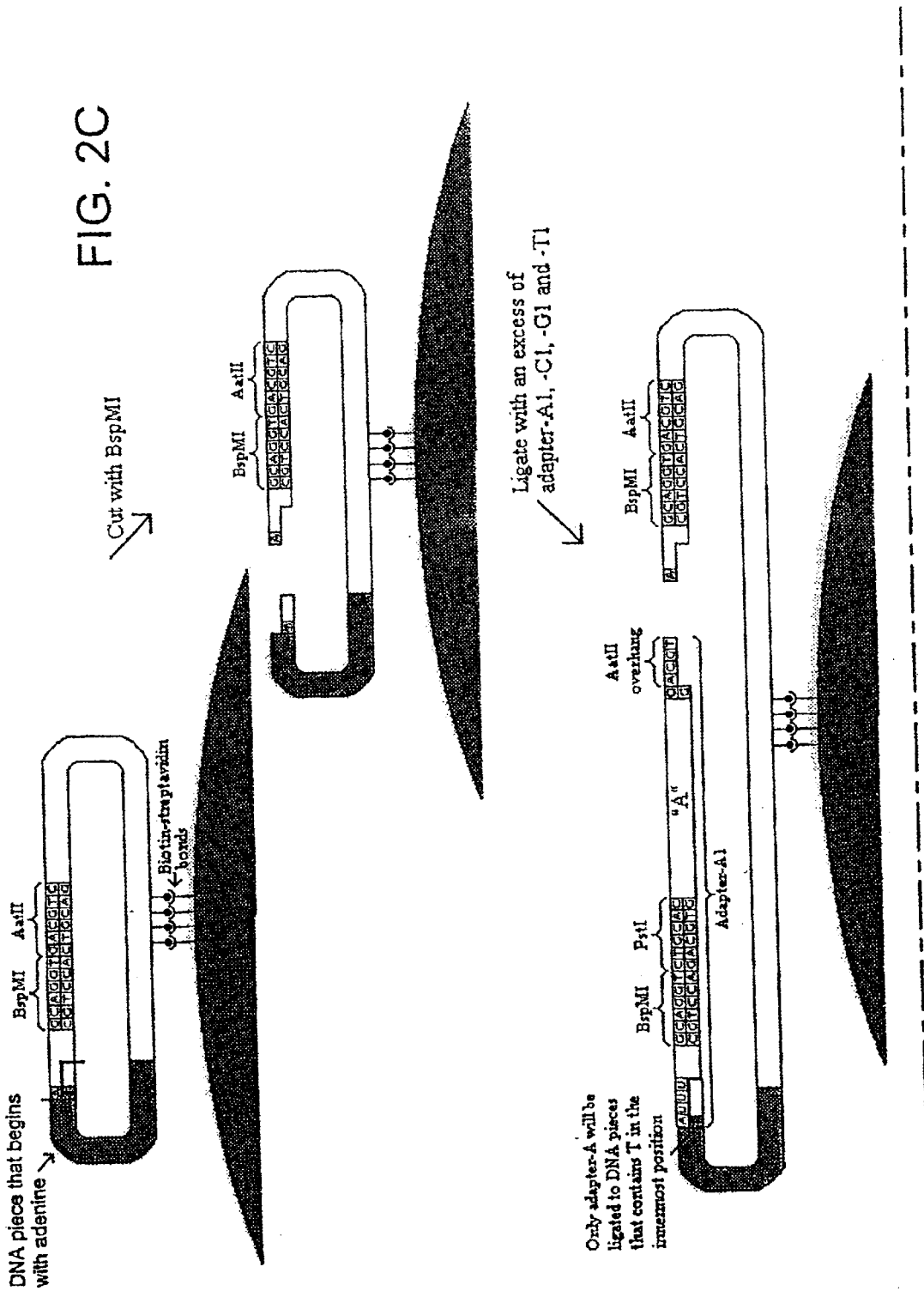
Figure 2C:
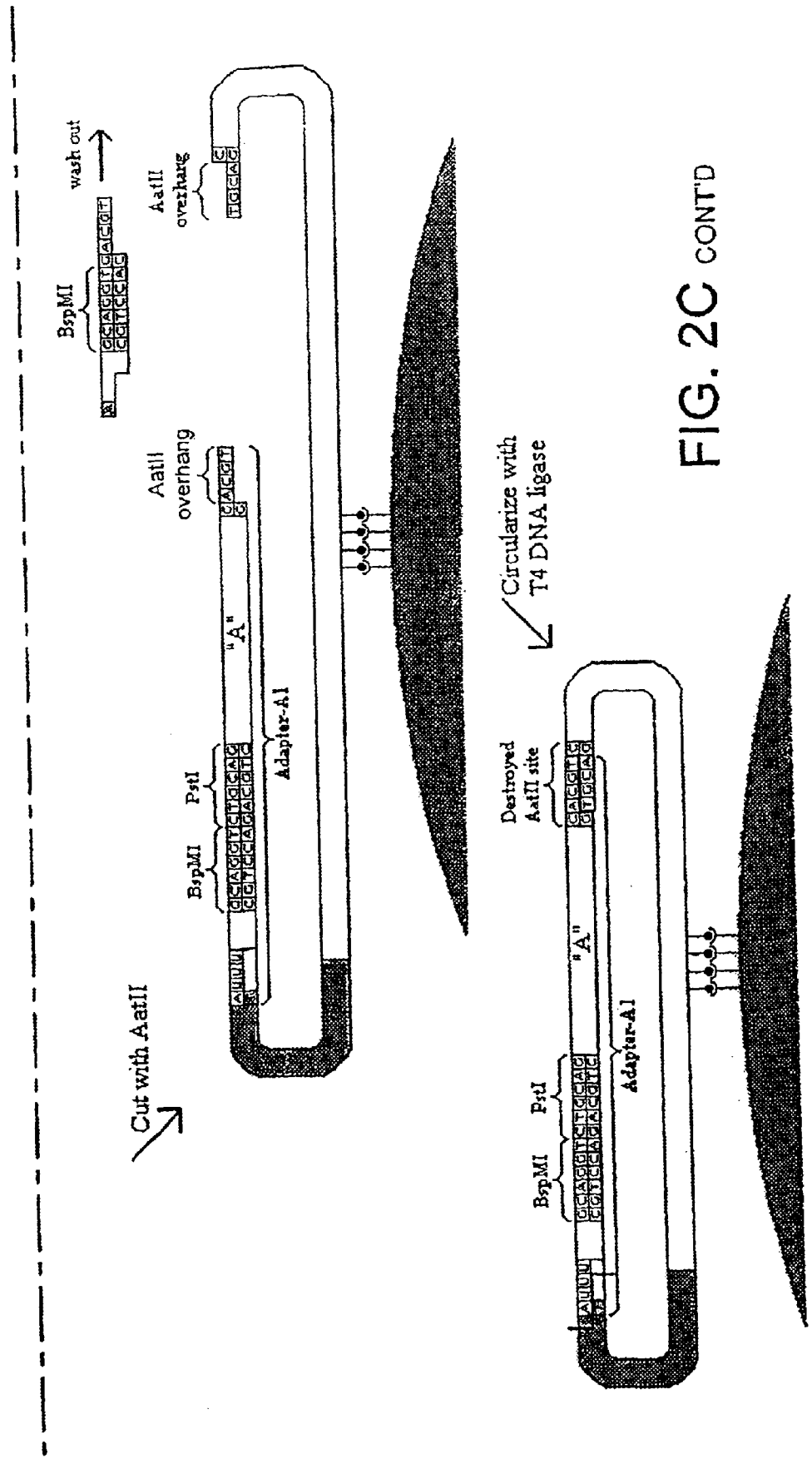

When the DNA fragments have been ligated into the base vector, they are fixed to a streptavidin substrate, e.g. parametric spheres. By using Dynabead's kilobase BINDER kit, a very strong biotin-streptavidin binding is obtained, so that the reaction solutions can be changed quickly and efficiently with a minimum loss of DNA even with very many cycles. (Btiomagnetic Techniques in Molecular Biology, 3rd Edition, pp. 158–60, distributed by Dynal AS). The rest of the procedue consists of a cycle of four enzymatic reactions where one base per cycle is converted (FIG. 2C).

In this procedure the cycle is initiated by cutting with BspMI so that the first base of the DNA fragment is on the inside of a 5' overhang. In this case, it is thymine. Thereafter, a large surplus of Adapters A1, C1, G1, and T1 are added. These are designed so that adapter A1 is ligated to overhangs with thymine on the inside, C1 with guanine on the inside, etc. The adapters are also treated with phosphatase (e.g. alkaline phosphatase such as calf intestinal AP, Promega), so that ligations between the adapters are avoided. By using a thermostable ligase, high specificity is obtained in this step. In the third step, cleavage is performed with AatII so that an overhang is created that is used to circularize the vector in the last step. This completes the procedure and we return to the starting point. The only difference is that the BspMI sits is placed one base pair further ahead so that an overhang is created with the second base of the DNA fragment on the inside. The AatII site is also replaced with a PstI site so that in the next cycle adapters with PstI overhangs must be used. (The reason why AatIi/PstI adapters are used every second time is to prevent the adapters from being cut out again before the vector is circularized.)

EXAMPLE 3

Sequencing by the Introduction of Magnifying Tags by Using Two Restriction Enzymes, Creating Overhangs on Adjacent Regions of the Target DNA Allowing Proofreading The starting point for this variant is 256 adapters with all combinations of overhangs on four bases and 1,024 adapters with all combinations of overhangs on five bases (FIG. 3A). Of the top adapter type, 1024 variants must be created, while 256 variants are created of the bottom one. The relative size of the fragments is greater than the figure indicates. Note that both adapters have PstI overhangs, which makes it possible for them to ligate to each other. However, the overhangs will have been treated with phosphatase so that ligation between the adapters cannot occur until they have been treated with a kinase.

In the base vector, the BspMI and PstI sites are replaced by HgaI and SfaI sites compared to the base vector used in the first variant (FIG. 2).

Figure 3B:
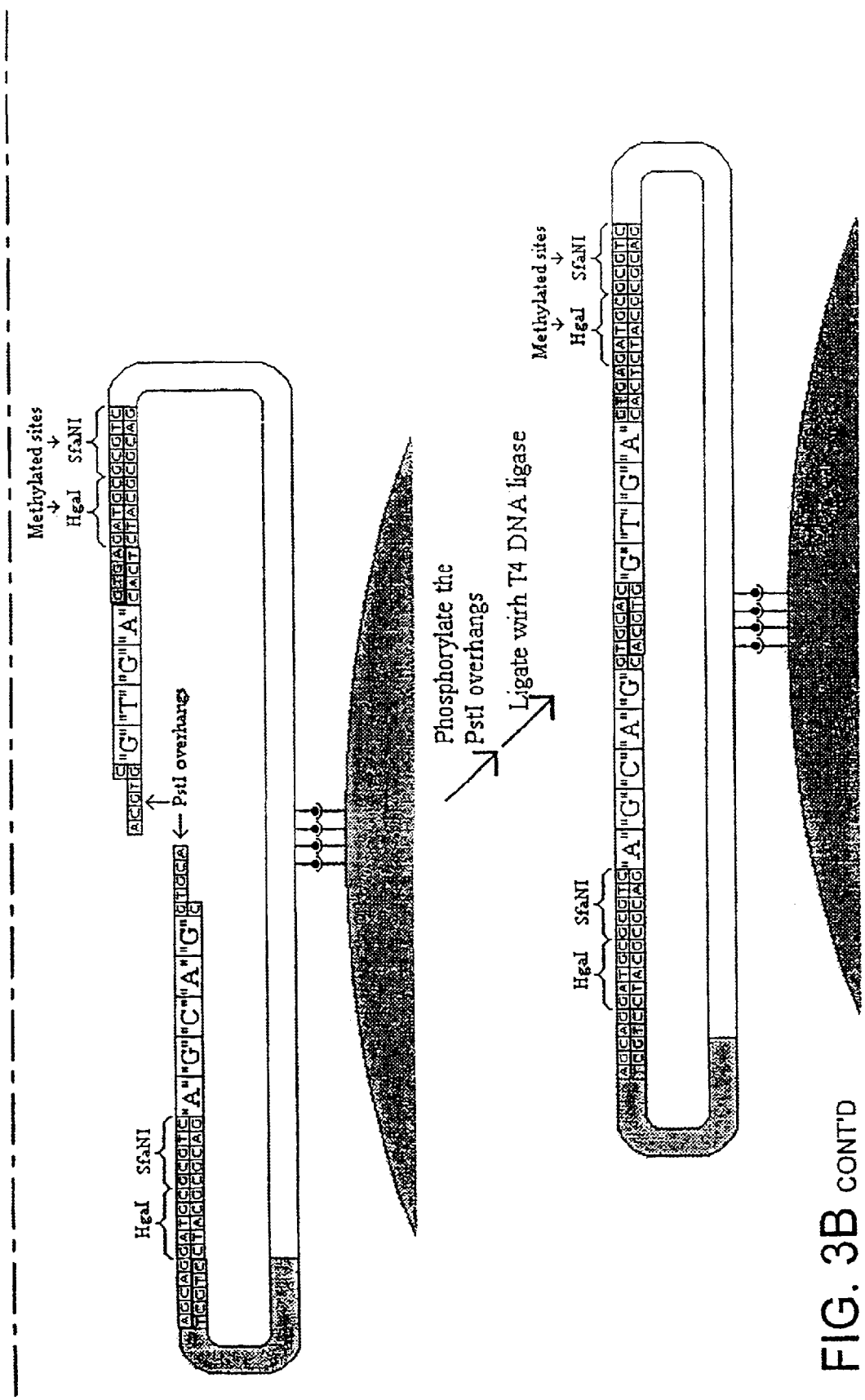

The rest of the procedure consists of a cycle of four enzymatic reactions where nine bases per cycle are converted (FIG. 3B). At the end of conversion, the vector is circularized bringing the reaction back to the starting point. The only difference is that the HgaI and SfaNI sites are displaced four base pairs further into the DNA fragment. In the next cycle four new base pairs are thereby created, plus five of the base pairs that were also converted in this cycle. By verifying that the four last-mentioned base pairs were converted in the same way in both cycles, one can check whether one or several incorrect conversions occurred.

Method
1) The target DNA molecules are fragmented with DNaseI or similar so that fragments of a few hundred base pairs are formed. These are treated to methylate the HgaI and SfaNI sites. The fragments are then ligated into a base vector that is attached to paramagnetic beads.
2) HgaI cleavage is performed.
3) SfaNI is performed.
4) Methylation is performed with HgaI and SfaNI methylase or other methylases that inactivate HgaI and SfaNI sites.
5) A large excess of adaptors are added and ligated, e.g. using Pfu or Taq, with the overhangs that were formed by HgaI and SfaNI in steps 2) and 3). In this step the Pst I overhangs do not become ligated since they have been treated with phosphatase.
6) The adaptors' PstI overhangs are phosphorylated and then ligated with e.g. T4 DNA ligase to circularize the vector.
7) The cycle is repeated for the desired number of times by restarting at step 2).
8) The converted target molecules are released from the base vector by cleavage using the restriction cleavage site in the base vector that flanks the ligated target molecules. Any cutting sites that may be in the magnifying tags must be inactivated in advance.
9) The converted DNA molecules are made single stranded and hybridised with fluorescent probes.
10) The converted DNA molecules are anchored to a scanning surface, stretched and the fluorescent probes scanned with a fluorescent scanner or similar (as with DIRVISH).
11) Appropriate software is used for image recognition and reconstruction of the target sequence.

One way in which this may be performed is as follows in which all volumes are calculated without the volume of the beads):
1) Random fragments are cloned into a base vector attached to paramagnetic beads as described previously.
2) A magnet is used to sediment the beads and wash the tube with approximately 100 µl 1×NE Buffer 1.
3) 10 µl 10×NE Buffer 1, 4 units of Hga I per µg of DNA and water is added to a final volume of 100 µl. This is incubated at 37° C. for 1 hour.
4) The HgaI enzyme is inactivated, at 65° C. for 20 minutes.
5) A magnet is used to sediment the beads and the tube washed with 1×NE Buffer 3.

6) 10 μl 10×NE Buffer 3, 2 units of SfaNI per μg of DNA and water is added to a final volume of 100 μl. This is incubated at 37° C. for 1 hour.
7) The SfaNI and HgaI sites are methylated.
8) A magnet is used to sediment the beads and the tubes are washed with 1×ligase buffer.
9) The solution containing the conversion adapters is added. The ratio between target DNA molecules and conversion adaptors may be 1:50. 100 μl 10×ligase buffer, 10 μl T4 DNA ligase (400 U/μl, NEB #202) and water is added to a final volume of 1 ml. This is incubated at 16° C. for 12–16 hours.
10) A magnet is used to sediment the beads and the tube is washed with 1×kinase buffer.
11) 2 μl 10 mM rATP, 10 μl 10×kinase buffer, 2 μl T4 polynucleotide kinase (30 U/μl) and water is added to a final volume of 100 μl. This is incubated at 37° C. for 10–30 minutes. (T4 polynucleotide kinase (70031) from United States Biochemicals.)
12) A magnet is used to sediment the beads and the tube is washed with 1×ligase buffer.
13) 100 μl 10×ligase buffer, 10 μl T4 DNA ligase (400 U/μl, NEB #202) and water is added to a final volume of 1 ml. This is incubated at 16° C. for 12–16 hours.
14) Steps 2)-13) are repeated one or several times.

If for example Bensimon's method (Michalet et al., 1997, Science, 277, p1518–1523) for stretching DNA molecules is used, approximately 1 million DNA molecules of 500 kb can be stretched per scanning surface. If each signal is approximately 5 kb, this means that each DNA molecule of 500 kb provides information about sequences of 100 base pairs. This means that one scanning surface will provide information about 100 million base pairs. A successful reconstruction of the target sequence, however, will depend on the sequence pieces overlapping so that many base pairs will have to be scanned at least twice.

EXAMPLE 4

Method of Sequencing Involving Completion of a Restriction Site to Identify the Terminal Base of a Target Molecule This method is based on the high specificity that many of the enzymes active in DNA metabolism have in recognizing substrates. The method is illustrated below with restriction enzymes, but a number of other DNA metabolizing enzymes, such as site specific restriction enzymes, transposases etc. can also be used. For most restriction enzymes mutation of one of the base pairs at the cleavage site is as a rule sufficient to prevent further cleavage by the enzyme In this method a target molecule is ligated to a linker which contains only a part of a restriction site. Where this site is completed by the target DNA, cleavage can be effected, after which a complementary adapter may be bound indicating those molecules which completed the site and hence exhibited a particular end base. The method is illustrated for adenine in FIG. 4.

Figure 4C:
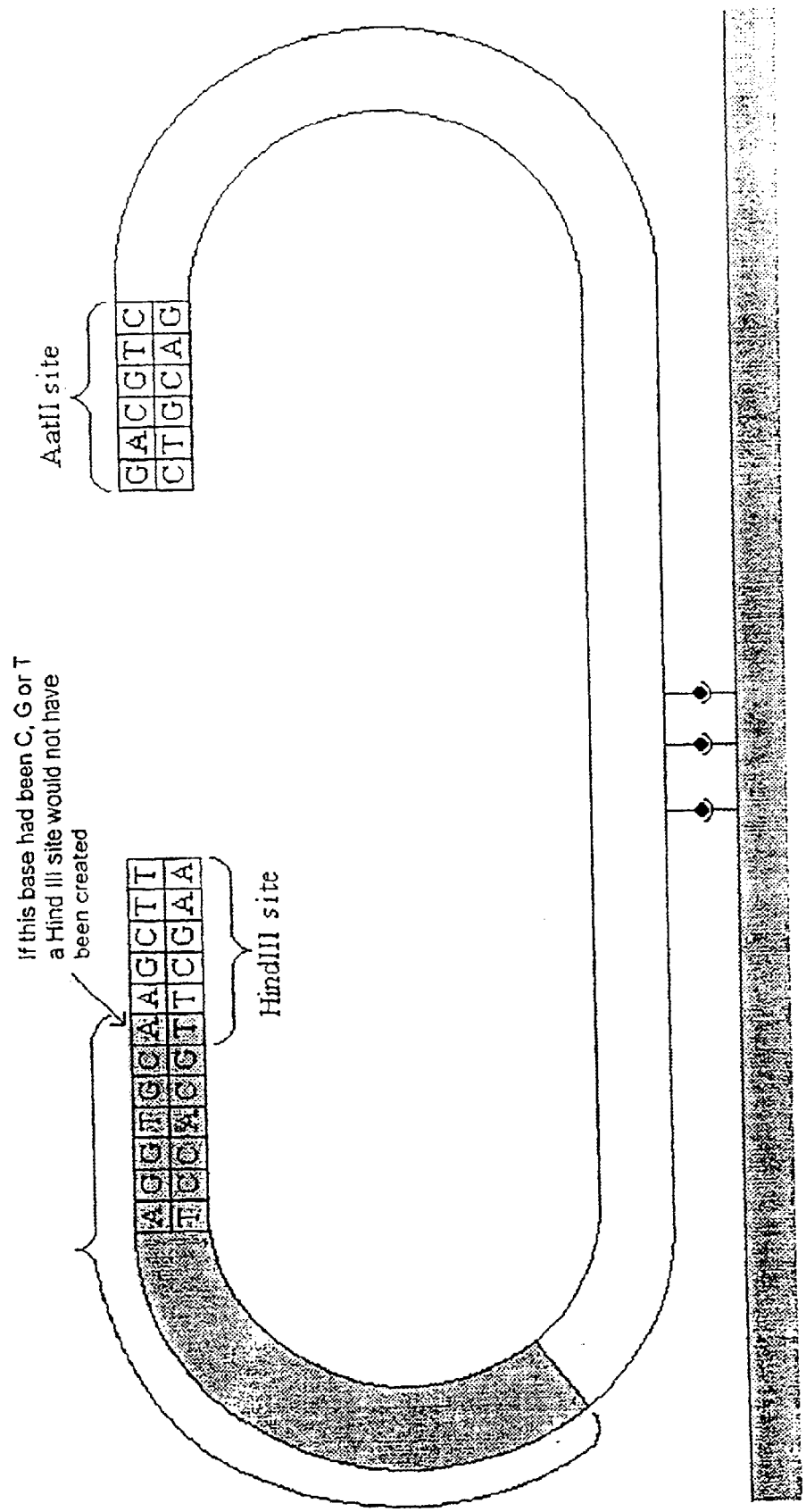
FIG. 4 shows a method of sequencing involving completion of a restriction site to identify the terminal base of a target molecule in which A) shows adapters which may be used in the process, B) shows the linker molecule containing part of the restriction site and C) shows the linker molecule bound to the target DNA to complete the restriction site.

Method
1) The DNA molecules that are to be sequenced are cut with four different, standard restriction enzymes (EnzA, EnzC, EnzG, and EnzT).
2) These molecules are then ligated to four different DNA linker molecules (Molecule A, C, G, and T). Each of these molecules has an almost complete site for EnzA, C, G, and T, respectively, at the end where they only lack one base pair (A, C, G, and T, respectively) in order to get a complete base pair. An example of such a linker molecule is: shown in FIG. 4B. In this molecule there is a HindIII site that lacks the A/T base pair. If this linker ligates to DNA pieces that do not have the A/T base pair, the MnlI can be used to remove the molecule from the DNA piece. FIG. 4C shows linker molecule A ligated to a DNA piece with the A/T base pair at the end, so that a complete HindIII site has been created. In the next step where HindIII is used for cutting, a HindIII overhang will be created that can be ligated to adapter A.
3) The four restriction enzymes are added to the solution to allow cleavage. There will only be complete cutting sites where each linker molecule A, C, G, and T has ligated to DNA molecules that have the missing base pair at the end (A, C, G, or T for molecule A, C, G, or T, respectively).
4) Adapters are added with overhangs that complement those that have been generated with restriction enzymes and ligated such that the adapters get fixed to the correct DNA pieces. Appropriate adapters are shown in FIG. 4A. The top adapter is used for cycles 1, 3, 5, etc, while the bottom adapter is used for cycles 2, 4, 6, etc. The adapters have overhangs that are complementary to overhangs produced by HindIII. The AatII overhang on the top adapter will be used to ligate the other end of the adapter to the base vector so that it will be circularized. The MnlI site will generate a blunt end on the DNA piece so that a new cycle can be initiated. The PstI site will be used to ligate a new adapter in the next cycle where adapters with PstI overhangs are used.
5) The base vector is circularized with the DNA piece/adapter by cutting with, for example, AatII so that the other end of the adapter can be ligated to the base vector. In cases where no HindIII site has been created, a small fragment with a PstI site is ligated into the AatII overhang of the base vector.
6) Cleavage is performed with a restriction enzyme that generates a new blunt end on the DNA piece so that a new cycle may be started.

EXAMPLE 5

Figure 5C:
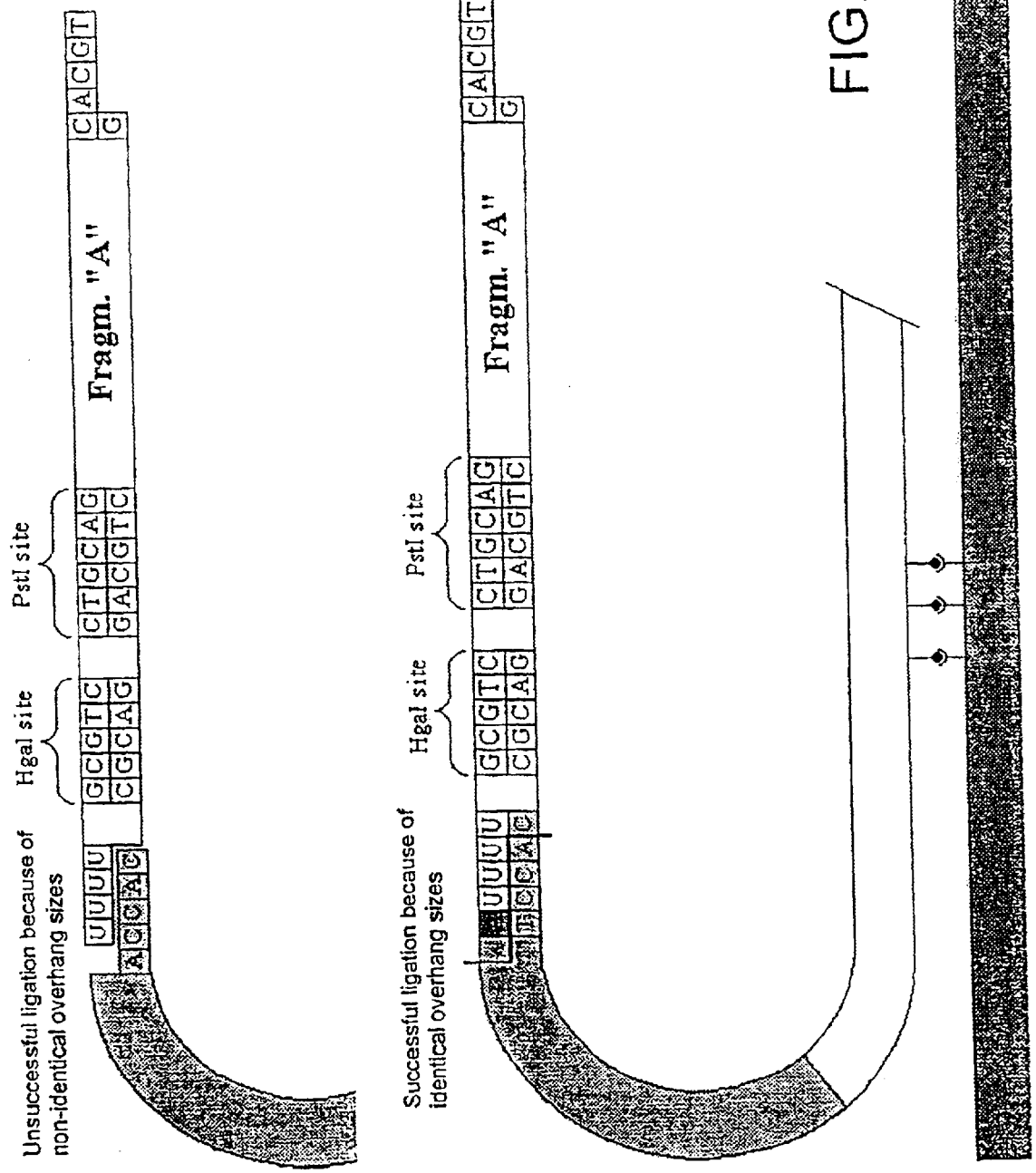
FIG. 5 shows a method of sequencing using a Klenow fill-in reaction coupled with hybridization and ligation in which A) shows the base vector into which the target molecule has been ligated; B) shows the structure of the adapter A used for cycle 1, 3, 5 etc; and C) shows unsuccessful and successful ligation depending on whether size comparable overhangs have been created.

Method of Sequencing Using a Klenow Fill-in Reaction Coupled with Hybridization and Ligation This method is based on the very high specificity that the Klenow portion of DNA polymerase has for incorporation of nucleotides, and the fact that most DNA ligases lack the ability to ligate overhangs of different sizes. The method is shown in FIG. 5 in which an overhang is made in the target molecule which is longer than the overhang in the adapter molecules. Only those target molecules which are appropriately extended to include the correct further base to reduce the overhang will be ligated to the adapter. FIG. 5 illustrates the method for adenine.

Method
1) DNA pieces are ligated into the base vector as shown in FIG. 5A. Apart from biotin which makes it possible to fix the molecule to a streptavidin substrate (e.g. Dynal's M280 streptavidin-covered magnetic spheres), the base vector contains a site for a restriction enzyme that cuts inside the polynucleotide (e.g. HgaI), as well as a site for a standard restriction enzyme (e.g. EcoRI).
2) The vector is cut with HgaI so that an overhang with five base pairs is formed from the polynucleotide.
3) After that e.g. base A together with Klenow are added so that the overhangs that start with "T" will be shortened to a four base pair overhang.
4) The reaction solution is then replaced with a solution of ligase and gene fragments (adapters) with four base pair overhangs. The overhangs can consist either of universal nucleotides or a combination of all possible compositions of an overhang with four base pairs. The overhang with universal nucleotides has the ability to ligate to 5' overhang on four bases in all combinations. The gene fragments also contain a site for a restriction enzyme that cuts inside the polynucleotide (e.g. HgaI), a site for a standard restriction enzyme (e.g. EcoRI), and a sequence that contains the signal "T" (a sequence that can be used as a probe, etc.) (FIG. 5B). The AatII overhang and the PstI site have the same function as in EX4, 1. Since polynucleotides with five base pair overhangs cannot be ligated to gene fragments with four base pair overhangs, it is only those polynucleotides that originally had a "T" innermost that are ligated to the gene fragments. Successful and unsuccessful ligation is shown in Example 5C. The top DNA piece does not manage to ligate to adapter A since no base was incorporated on the inside of the overhang. Since only overhangs with an "A" on the inside have incorporated a base, it is only these overhangs that are ligated to adapter A as shown at the bottom. The full line in the DNA piece indicates the overhang that will be formed through HgaI cutting. The same process is then repeated with bases C, G, and T.

5) Finally, the base vector is circularized with a DNA piece/adapter by cutting, e.g. with EcoRI and ligating.
6) Cleavage with HgaI is then performed, which generates a new overhang in the DNA piece, so that the reaction cycle may be started again.

In instances in which consecutive bases are identical adapters with overhangs of differing size may be used, e.g. overhangs of three bases allowing Klenow fill-in of 2 bases.

EXAMPLE 6

Method of Sequencing Using Adapters Which Function as Primers When Binding to Single Stranded Target Molecules Method
1) Adapters used in this method which have overhangs that correspond to the fragment composition are illustrated in Example 6A. Note the fragment composition that corresponds to the base composition in the overhang. DNA adapters that correspond to all combinations of fragments must be constructed.
2) Target DNA pieces are made into single strand pieces and ligated to the adapters at the 3' end and a primer template at the 5' end with the aid of RNA ligase (FIG. 6B). The prerequisite for successful ligation between the adapter and DNA piece is that the overhang of the adapter complements the 5' end of the DNA piece. This ensures that the correct fragments are connected to the DNA piece.
3) The target DNA pieces are hybridized with the adapters before the molecules are ligated to each other. Then one or several PCR cycles are run. The prerequisite for successful PCR cycles is that the ssDNA pieces have been hybridized and ligated to an adapter.
4) The EcoRI site is used to circularize the DNA molecule that is created after ligation between the adapter and DNA piece. The HgaI site is then used to create a new cut in the DNA piece so that the next cycle can begin. In order to reduce inter-molecular ligations after cutting with EcoRI, it may be advantageous to fix the molecules to a substrate, e.g. streptavidin-covered spheres.

EXAMPLE 7

Method of Sequencing Using Adapters Which Self-Hybridize

Figure 7:
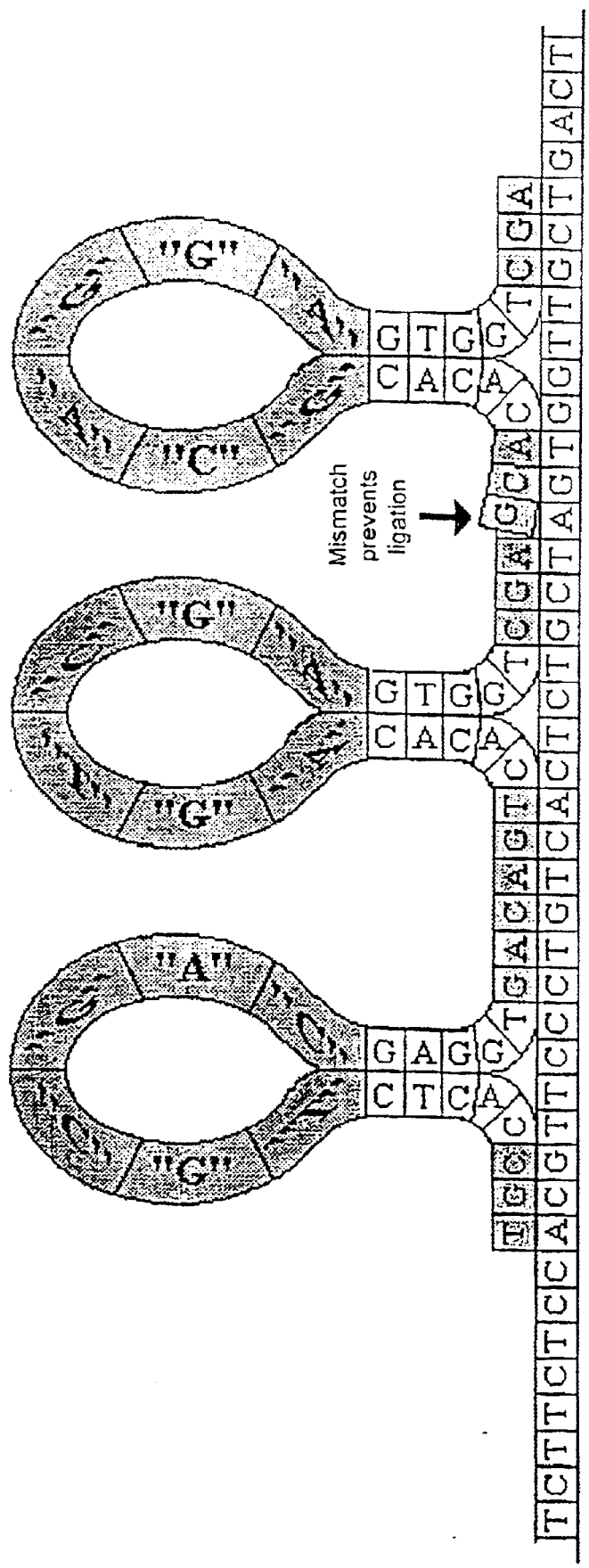
FIG. 7 shows adjacently aligned adapters which carry magnifying tags and which hybridize to the target and self-hybridize.

The starting point for this method is single strand DNA or RNA adapters that have the ability to hybridize with the DNA molecule that is to be sequenced, while at the same time carrying fragments (magnifying tags) that correspond to the bases to which they hybridize in addition to regions which self-hybridize (FIG. 7). By making such adapters with all possible combinations of fragments and by hybridizing them with the DNA molecules that are to be sequenced, multiple adapter may be aligned side by side (see FIG. 7). If the adapters are correctly aligned, ie. without a mismatch for the first two adapters, it will be possible to ligate them to each other so that they form longer chains.

EXAMPLE 8

Method of Constructing Adapters Corresponding to More Than One Base

One strategy for constructing adapters uses a principle similar to the one used to construct DNA chips. In that method, different oligonucleotides are made at various addresses in the same manner as for the construction of DNA chips. The same principle is then used to fix DNA fragments to the oligonucleotides in the same manner as base pairs are fixed to growing oligonucleotides. Finally, the DNA molecules are loosened so that a solution of adapters is obtained.

Figure 8:
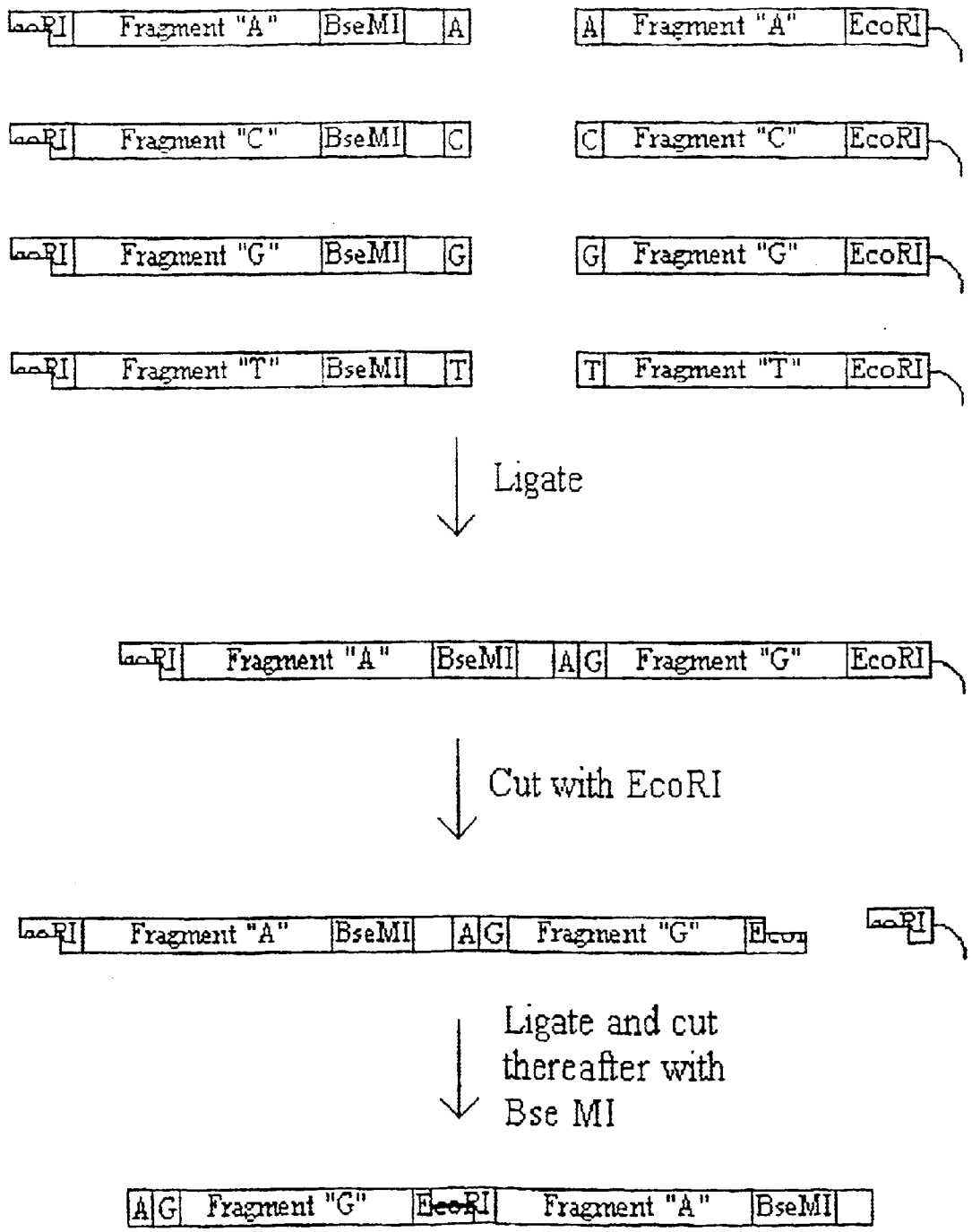
FIG. 8 shows a method of making adapters which contain magnifying tags corresponding to more than one base.

This Example also provides an alternative method for preparing adapters. This is illustrated in FIG. 8. Eight different adapters with one tag each are used to make 16 different adapters with two tags each as illustrated in FIG. 8. Starting with eight other one-tag adapters, one can make 16 new two-tag adapters that in turn can be combined with the first 16 to produce 256 different four-tag adapters. In this manner it is possible to produce adapter mixes where only the number of different molecules that can fit into the solution limits the number of permutations. The number of different one-tag adapters that is initially required is equal to four times the number of tags in each adapter. For example, if we want to make 16-tag adapters ($4.29 \times 10^9$ permutations), $16 \times 4$ different one-tag adapters are needed initially.

Method
1) Eight different one-tag adapters are used as illustrated in FIG. 8. The adapters on the left consist of an EcoRI overhang, a tag that is specific to the base that is at the very right on the molecule and a cutting site for BseMI. BseMI cuts outside of its own site and will create a blunt cut right beside the base on the right of the molecule. The adapters are also treated with phosphatase so that ligations between these adapters are reduced. The adapters on the right consist of a tag that corresponds to the base at the very left on the molecule and a cutting site for EcoRI. The adapters are also fixed to a substrate to prevent ligations between these adapters.
2) The process is initiated by mixing and ligating the two adapter populations. This produces 16 different DNA molecules that correspond to all permutations with two tags.
3) EcoRI is used to cleave. Ligation is then performed to circularize the molecules.
4) Finally, cleavage is conducted with EseMI and this produces a population with 16 different two-tag adapters.

EXAMPLE 9

Conversion Method Based on Hairpin Adapters

A central point in several of the previously described conversion alternatives is that after conversion of base pairs, the DNA fragments are transferred to the other end of the DNA molecule that is being converted. This frees the end that is being converted so that one can proceed to the next cycle while at the same time saving the DNA fragments. Below is another strategy for transferring DNA fragments to the other end of the DNA piece.

Figure 9:
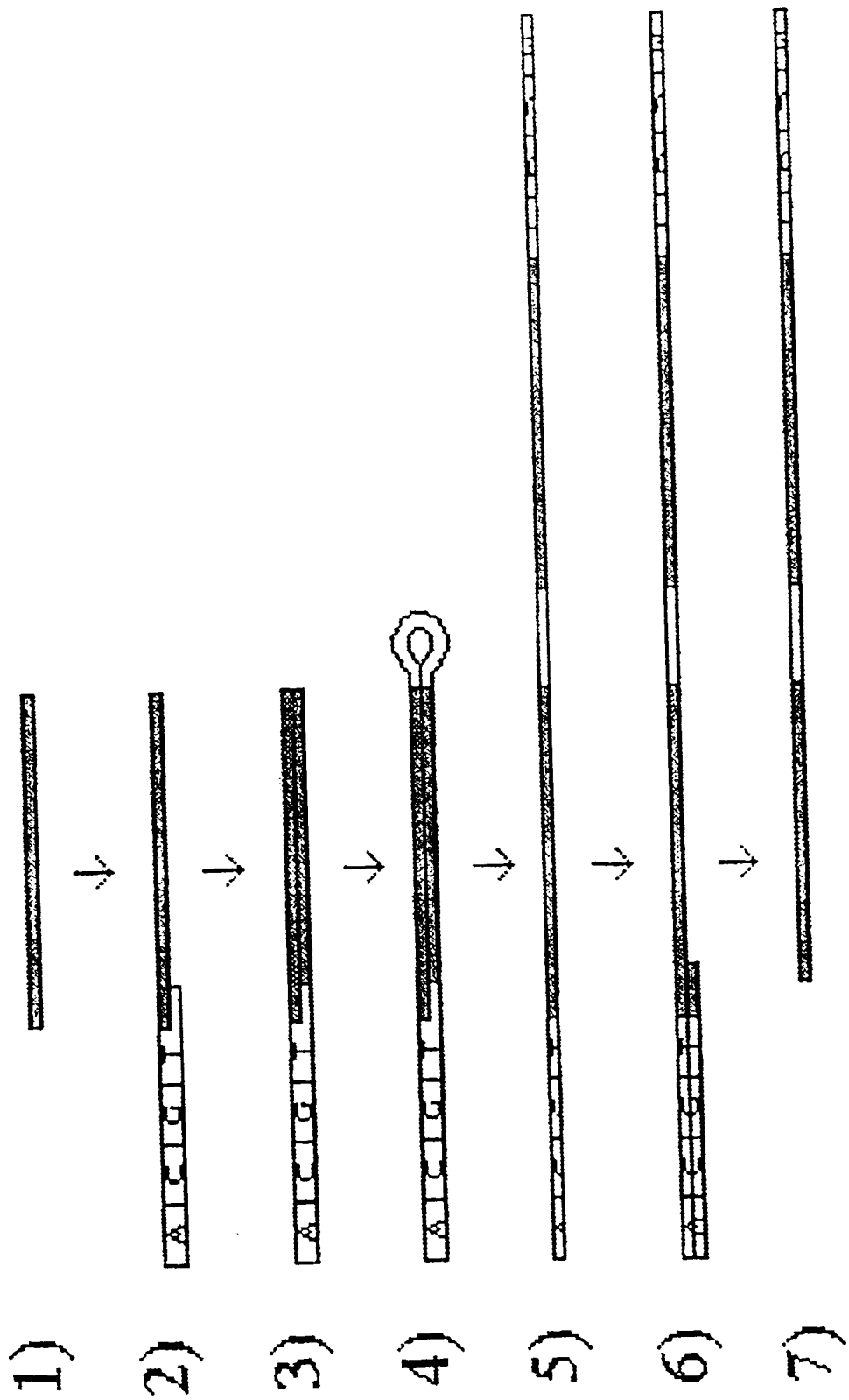
FIG. 9 shows a conversion method based on the use of hairpin adapters in which magnifying tags are copied to both ends of a target molecule.

The starting point is that many ligases, including T4 DNA ligase, can ligate overhangs on dsDNA to the ends of ssDNA. This can be utilized in the manner illustrated in FIG. 9.

Method
1) The target DNA is converted into single stranded form.
2) Conversion adapters are added and ligated to the 3' ends of the DNA pieces.
3) Polymerase extension is performed.
4) Hairpin adapters are added and ligated. The end of the conversion adapter is treated in advance so that it does not ligate to the hairpin adapter (e.g. treated with phosphatase).
5) The DNA molecules are melted.
6) The single strand DNA molecules are hybridized with DNA molecules that complement the fragments. The complementary DNA molecules also have an overhang with universal bases that are hybridized with the first bases in the target DNA.
7) With the aid of a cutting site for an enzyme that forms overhangs outside of its own recognition sequence, the DNA is made ready for the next conversion cycle.

In each of the above cycles the magnifying tags are duplicated in each cycle. This allows proof-reading to be performed.

EXAMPLE 10

Conversion Method Based on Linking Converted DNA Molecules

Figure 10:
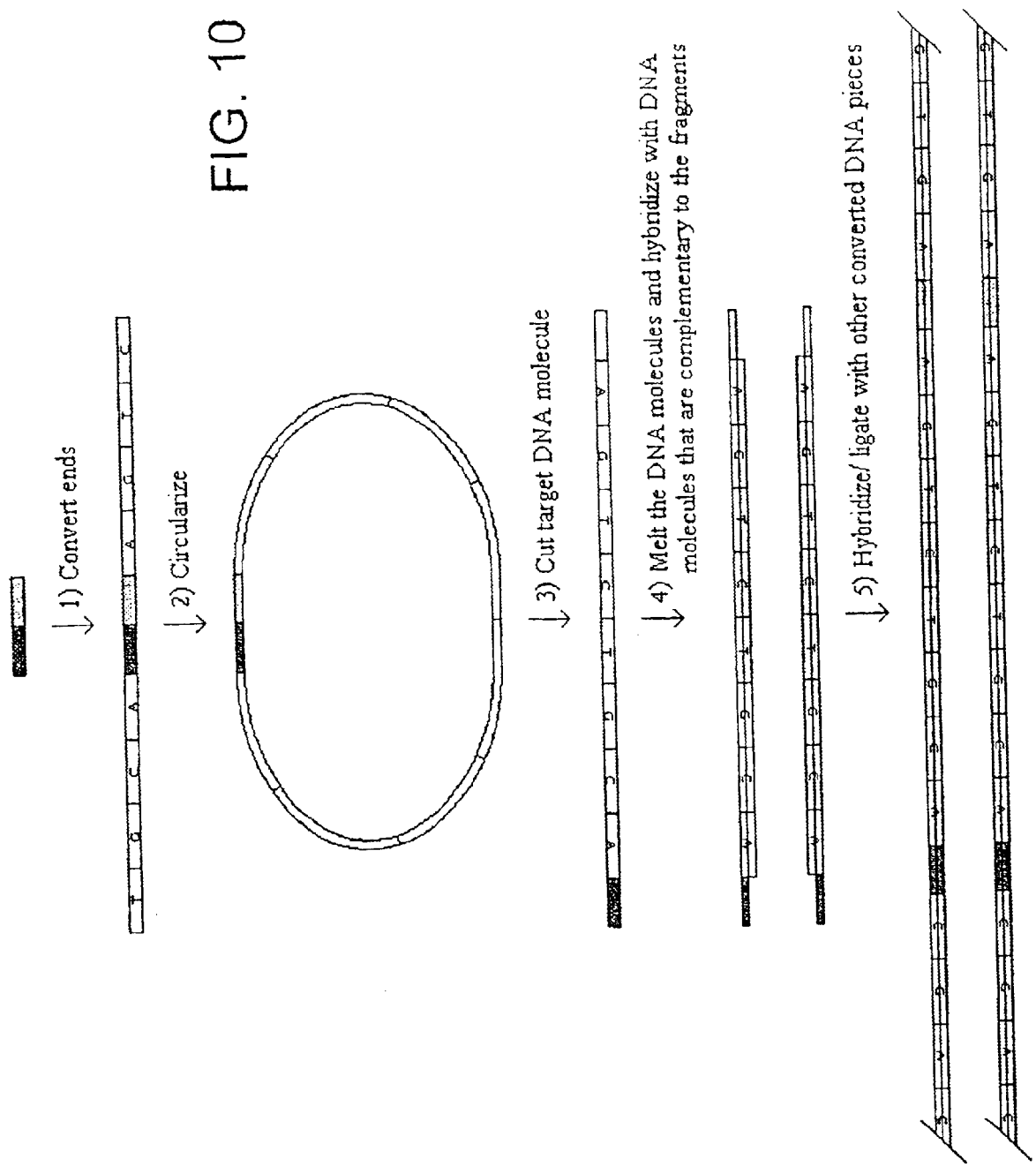
FIG. 10 shows a method of conversion based on linking converted DNA fragments to one another.

Many of the previously described conversion methods are based on conversion taking place in a cyclical process. The number of converted base pairs per chain of magnifying tags (or signal chain) thereby increases linearly with the number of cycles. An alternative strategy is to link converted DNA pieces into long chains. There are very many possible methods based on this principle and one proposal is found below, and is illustrated in FIG. 10.

Method

The method starts by cutting and sorting the target DNA according to size. DNA pieces of a specific length, e.g. 30 base pairs, are then removed from the procedure.
1) The ends of the DNA pieces are converted using previously described methods.
2) The converted DNA molecule is circularized.
3) A IIS enzyme that uses a cleavage site located on the end of the conversion adapter is added. This cuts the DNA piece as illustrated in FIG. 10.
4) The DNA molecules are melted and hybridized with DNA molecules that complement the fragments, e.g. probes labelled with fluorescence.
5) Finally, the converted DNA pieces are hybridized and ligated, if required, in the solution.

Since the overhangs with target DNA in the above-mentioned example seek complementary overhang, each converted DNA piece will be hybridized/ligated to encountered DNA pieces. This creates a chain of magnifying tags (signal chain) that provides information about sequence pieces of 8 base pairs interrupted by 22 unknown bases (e.g. AGCTGTGA N22 AGTCTGCA N22 TGAC (SEQ ID NO:11)). The number of unknown base pairs is determined by the initial length of the DNA piece minus the number of base pairs converted per DNA piece. Based on overlaps between signal chains, it is then possible to reconstruct the target sequence even in areas with repetitive sequences.

EXAMPLE 11

Method of Doubling DNA

Figure 11:
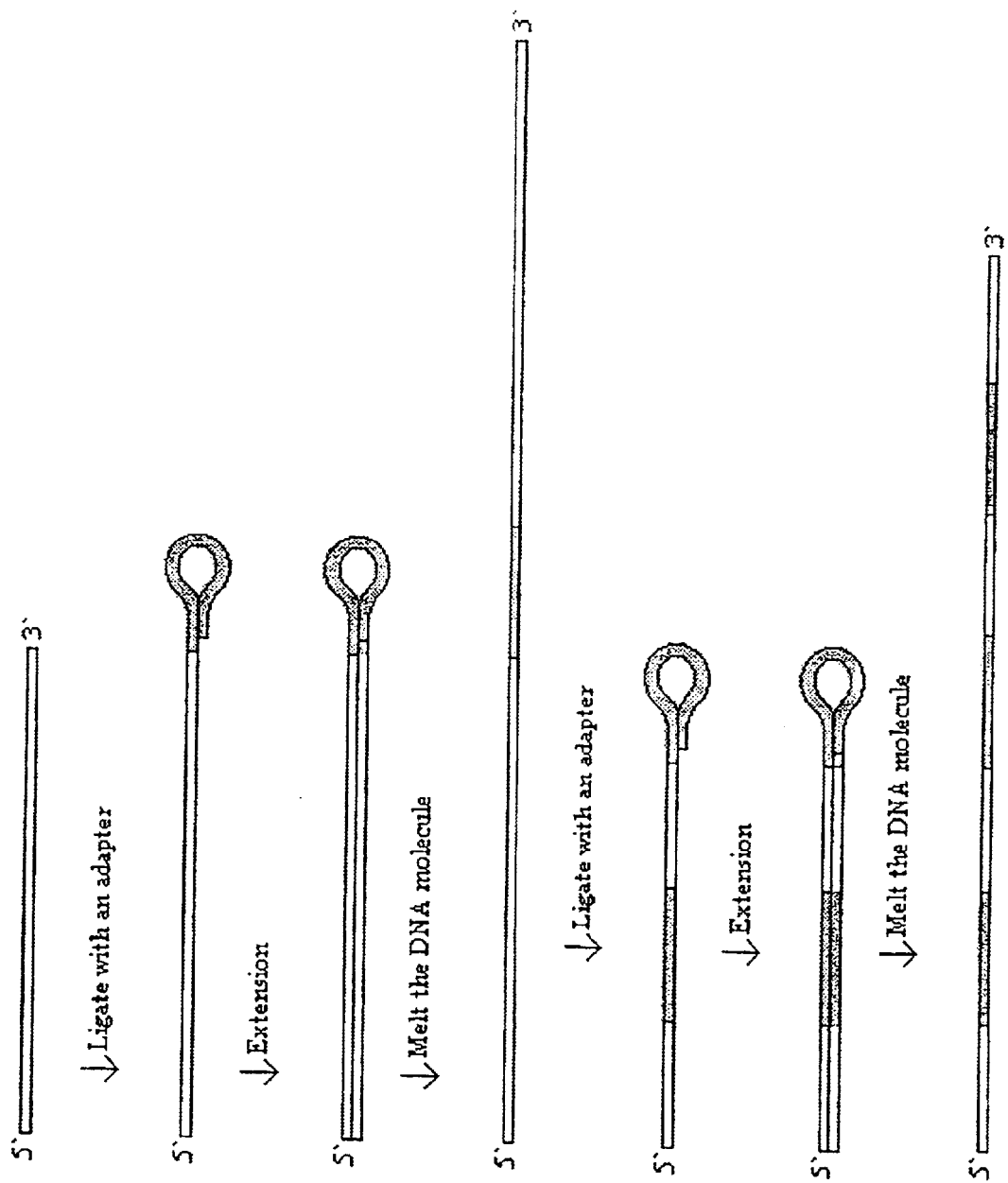
FIG. 11 shows a method of doubling nucleic acid molecules.

A single strand DNA molecule is subjected to two doubling cycles as shown in FIG. 11. Doubling is begun by ligating a hairpin adapter to the 3' end of the molecule. In the same manner as, for example, a reverse transcriptase uses a 3' hairpin loop as a primer, the adapter can be used as a primer for a polymerase that extends the molecule. Finally, the DNA molecule is dissolved so that we return to the starting point. Using this method to double a DNA molecule of x bp n times with the aid of an adapter that is y bp long, the length of the DNA will be:

1) $x \cdot 2^n + (2n-1)y$

The difference between two DNA molecules that were x and x+1 bp each before doubling will then be:

2) $(x+1) \cdot 2n + (2n-1)y - x \cdot 2n + (2n-1)y = 2n$

The difference in length between two doubled DNA molecules is therefore determined only by their absolute and not their relative length differences prior to multiplication.

EXAMPLE 12

Method of DNA Sequencing Utilizing a Primer-Based Sorting Strategy

This example demonstrates how to make 256 sequencing ladders that can be divided from each other using 16 separate gel separations and 16 different labels, e.g. fluorophores. The length of the sequence reactions can be substantially increased compared with methods which use only 4 sequencing ladders. It is thus possible inter alia to reduce the amount of sorting work, the number of primers required etc. when sequencing long sequences. 16 sequencing ladders and 16 fluorophores are used in this example, but clearly the number of sequencing ladders and fluorophores can be adapted to suit most requirements and available equipment. The more sequencing ladders and fluorophores used, the longer the sequence reactions may be.

Methods

Figure 12A:
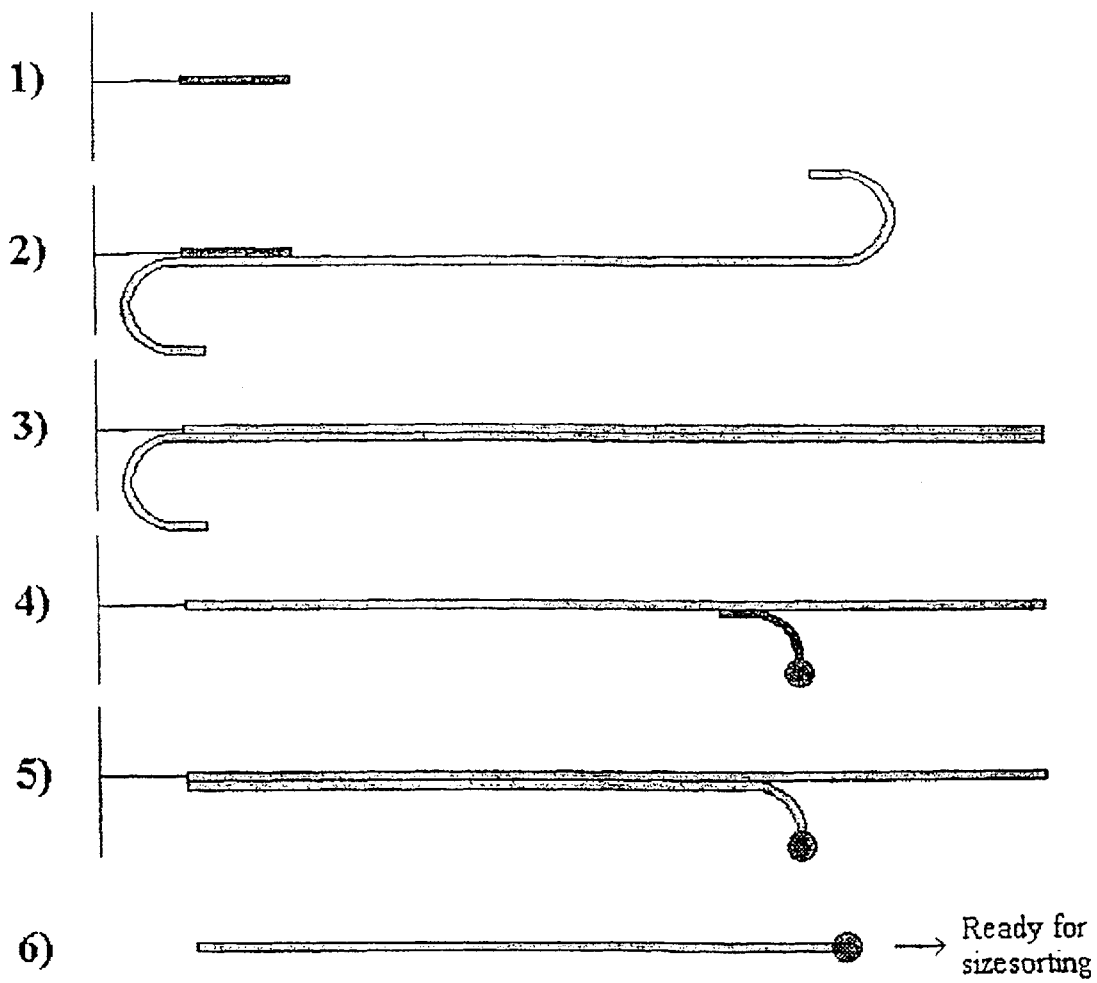
Figure 12B:

An overview of the method used is illustrated in FIG. 12A.
1) A solution of target DNA is divided into 16 wells containing sequencing primers anchored to the wells' substrates. These primers determine the fixed start point for the polymerase reaction and hence the common origin allowing the size of the ultimate products which are produced to be indicative of the distance of the end sequence from that origin.
2) A polymerase extension reaction is carried out, the DNA molecules are heated to cause melting and the wells are then washed.
3) 16 different primers are then added to each of the 16 wells (total of 256 different primers) as illustrated in FIG. 12B. All the primers added to each well are identical except for bases 3 and 4 at the 3'-end. Primers with AA in this position are connected to signal 1, primers with AC in this position are connected to signal 2, etc. The primers in well 2 are identical except that they start with for example AC instead of AA at the 3' end, while the primers in well 3 start with AG, etc. Thus in total there are 256 different primers covering all the 256 4-base permutations at the 3'-end. A unique fluorescence signal is attached to each of the 16 different primers. A further polymerase extension reaction is then conducted.
4) The wells are then washed before melting the DNA molecules. The single-strand DNA molecules thereby freed are then sorted according to size with 16 separate gel separations (one for each well).
5) The fluorescence signals are recorded and the target sequence reconstructed with appropriate software.

Results

Figure 12C:
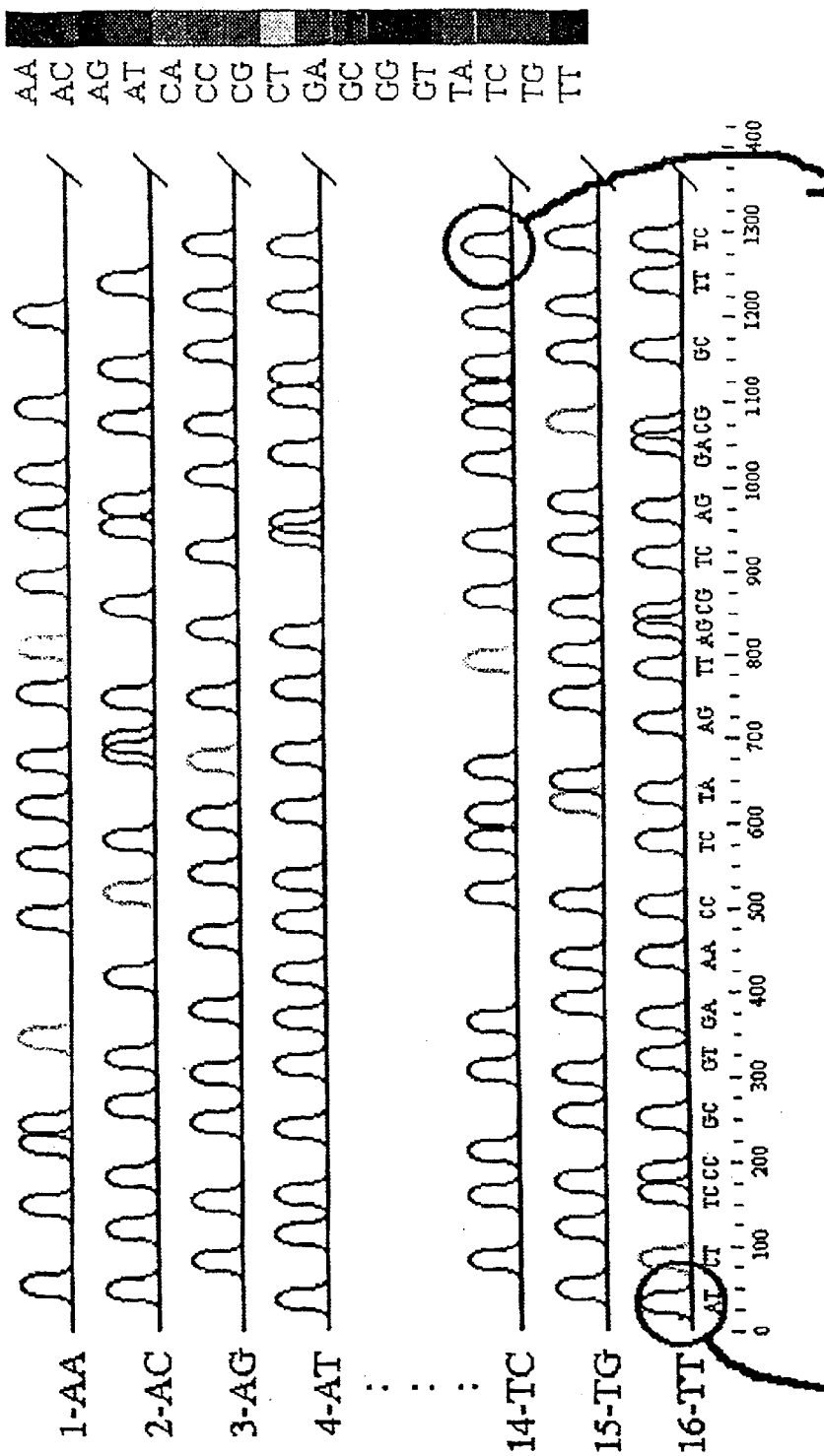

The results are shown in FIG. 12C. Each fluorescence signal provides information about a 4-base sequence piece. Information about the first two bases can be derived by reference to the well from which the fluorescence signal is read, while the last two bases can be determined on the basis of the particular signal which is present.

EXAMPLE 13

Method for DNA Sequencing Utilising a Sorting Strategy Based on Hybridisation

In this method target DNA molecules are addressed to different sites on a scanning surface by means of hybridisation to octamers on that surface. The molecules are then stretched and the distance from a fluorescent signal to the perpendicular anchoring line is assessed to provide information about the location of the octamer in the target sequence. The general procedure is shown in FIG. 13.

Methods

1) The starting point is a scanning surface consisting of 65,536 addresses. A perpendicular anchoring line with single-stranded octamers is attached to each address. AAAAAAAA (SEQ ID NO:12) octamers are anchored to the plate at address 1, AAAAAAAC (SEQ ID NO:13) octamers to the plate at address 2, etc, so that all the 65,536 octamer permutations each have their own address.
2) Single strand target DNA molecules with fluorescent labelling at one or both ends are then mixed over the scanning surface so they can be hybridised to the octamers. (FIG. 13A)
3) If so desired, octamer/target DNA bonds may be reinforced by exposing the molecules to UV radiation, carrying out a polymerase extension with the octamer as primer, or by other means.
4) The scanning surfaces are then washed and the DNA molecules stretched. (FIG. 13B)
5) The surface is scanned using a fluorescent scanner to record the intensity of the fluorescence at each address as a function of the distance to the anchor line and the target sequence reconstructed using appropriate software.

Results

Figure 13C:
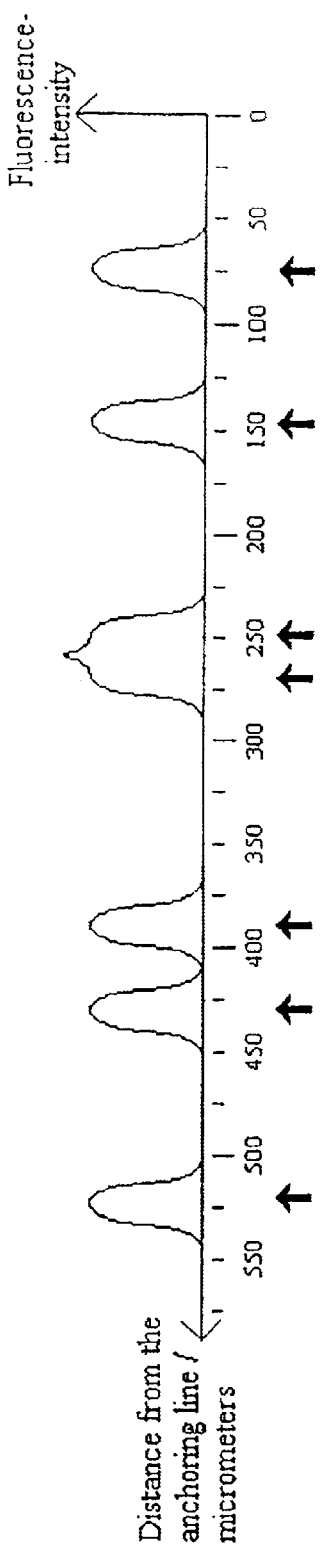

The results which are obtained are shown in FIG. 13C. At the illustrated address there are 7 different lengths of DNA molecules of approximately 150, 300, 500, 550, 780, 870 and 1040 kb (if the DNA molecules are stretched with 2 kb per micrometer).

EXAMPLE 14

Method for DNA Sequencing Using a Ligase-Based Sorting Procedure

This example is based on a ligase-based sorting procedure in which 65,536 sequencing ladders are sorted into 65,536 addresses. As opposed to other methods which use 4 sequencing ladders that each represent a base, in this method each of the 65,536 sequencing ladders will represent a sequence piece of 8 bases. This reduces the precision requirement for sorting by size compared with methods which only use 4 ladders. The length of the sequence reactions can thus be increased and it is also possible to utilise a wide range of methods for sorting polymers by size.

In this example, the sorting by size is illustrated by a method in which the lengths of the stretched DNA molecules is measured. Other variations are, however, conceivable, in which the sorting by size is performed directly on a scanning surface—for example measuring the DNA molecules' signal intensity after using a labelling method whereby the DNA molecules' signal intensity is proportional to the length etc. Variations are also conceivable in which the sequencing ladders are kept physically apart, released from the substrate at different times etc. making it possible to analyse each of the 65,536 sequencing ladders separately using a flow cytometer, mass spectrometry, nanopore analysis, gel sorting etc.

Method

1) A sequencing ladder is produced starting with a target sequence of e.g. 1 Mb, prepared as described herein.
2) The target DNA is methylated so that the cleavage sites for the restriction enzymes to be used in steps 3) and 6) are inactivated.
3) A 4base overhang is produced in the target DNA's arbitrary ends as described herein. The DNA molecules' arbitrary ends may, for example, be ligated to a DNA linker containing a binding site for a IIS enzyme that makes an overhang of 4 base pairs. The binding site is positioned to make an overhang in the actual target DNA. The molecules are then cleaved with the IIS enzyme.
4) The target DNA is then sorted as described in Example 12 by distributing the solution between 256 wells. The well walls are covered with sorting adaptors with 4-base overhangs that can complement the overhangs made in step 3). The sorting adaptors also contain a binding site for an IIS restriction enzyme, e.g. FokI, which is positioned so that overhangs can be formed comprising the four base pairs lying beside those cut in step 5.
5) The target DNA is ligated with the sorting adaptors and the tube is then washed so that the DNA that has not been ligated is removed.
6) Cleavage with the IIS enzyme is performed so that the target DNA loosens and new 4-base overhangs are formed.
7) The target DNA is distributed from the 256 wells between 256 microarrays as described in Example 12. All the microarrays are alike and consist of 256 addresses with sorting adaptors with 4-base overhangs that can complement the overhangs made in step 6). At address 1 the sorting adaptors have AAAA (SEQ ID NO:1) overhangs, at address 2 they have AAAC (SEQ ID NO:8) overhangs etc.
8) Ligase is added and the mixture incubated. At address 1 there will be target DNA with TTTT (SEQ ID NO:2) overhangs, at address 2 there will be target DNA with TTTG (SEQ ID NO:9) overhangs, etc.
9) The scanning surfaces are washed, the DNA molecules addressed and coloured using TOTO-1, YOYO-1 or similar.
10) A CCD camera or similar is used to photograph the addresses. The CCD camera, may for example, be set to take one photo per address.
11) Appropriate software is used to recognize the fluorescent DNA molecules, measure their lengths and then reconstruct the actual target sequence.

One way in which this might be performed is as follows:
1) To each well; add one aliquot with target DNA molecules containing arbitrary 4-bases overhangs, 10 µl 10×ligase buffer, 1 µl T4 DNA ligase (400 U/µl, NEB #202) and water to a final volume of 100 µl. Incubate at 16° C. for 12–16 hours.
2) Remove the liquid and wash the wells with 1×NE Buffer 4 one or several times.
3) Add 10 µl 10×NE Buffer 4, 4 units FokI (New England Biolabs, #109) per µg DNA and add water to a final volume of 100 µl. Incubate at 37° C. for 1 hour.
4) Inactivate at 65° C. for 20 minutes.
5) EtOH precipitate the DNA molecules from each well in separate tubes.
6) Dissolve the pellet and add 10 µl 10×ligase buffer, 1 µl T4 DNA ligase (400 U/µl, NEB #202) and water to a final volume of 100 µl. Incubate with the microarrays at 16° C. for 12–16 hours.
7) Stretch out, label and analyse the molecules.

Results

The presence or absence and size of molecules at particular addresses indicates both sequence information and its position. Thus if address 1 of microarray 1 contains DNA molecules of 100 micrometers, this indicates that the sequence corresponding to the octamer used (albeit by 2-step sorting) to bind that molecule is present at ®kb (e.g. TTTTTTTT (SEQ ID NO:14)). Similar the presence of 2 differently sized molecules would indicate a repeat of the particular sequence. The absence of any molecules at a particular address would indicate the absence of the sequence complementary to the immobilizing octamer in the target sequence.

A potential source of erroneous sorting in the above example is that rough-sorting adaptors may also function as fine-sorting adaptors. However, this problem can be avoided by having a cutting site for another restriction endonuclease in the rough-sorting adaptor which enables the rough-sorting adaptors to be cut away before scanning. Although it has not been mentioned in the above example, it is also important to terminate the end of the DNA piece that is not attached to the rough-sorting adaptors. This may, for example, be done by Klenow filling.

If Bensimon's method (Michalet et al., 1997, supra) is used in the above method for stretching DNA molecules, 1–2 million DNA molecules can be stretched on a scanning surface measuring 1.28×28 cm. Each of the 256 addresses will contain approximately 4–8.000 stretched DNA molecules. As a sequence piece with 8 base pairs will be repeated every 65,536th base pair, there will be on average 15 different lengths at each address if the target sequence is 1 Mb (1,000,000/65,536=15.2). Each length will thus be measured 260–520 times on average (4–8,000/15.2= 260–520).

EXAMPLE 15

Method for DNA Sequencing in Which the Target DNA Molecules are Anchored to a Fixed Reference Point In this method PNA octamers carrying a linear arrangement of magnifying tags (the signal chain) is hybridized to target DNA fixed on a scanning surface which is then scanned and the position of the region complementary to the octamers within the target sequence determined. The general procedure is shown in FIG. 14.

Methods
1) The starting point for the protocol is the anchoring of target double stranded DNA molecules to a fixed reference point on a scanning surface as described herein, for example to an anchoring line that is perpendicular to the scanning plate.
2) 65,536 permutations of conversion adaptors (ie. adapters carrying magnifying tags) consisting of a PNA octamer attached to a signal chain with a composition corresponding to the octamer are then added. The signals may be fluorescence labelled spheres, beads or carry other appropriate labels. The PNA molecules are thus hybridised with the target DNA molecules.
3) The molecules are stretched and their positions recorded as well as the composition of the signal chains.
4) Appropriate software is used to reconstruct the target sequence.

Results

The results are shown in FIG. 14. The distance between the signal chains and the fixed anchoring point provides information about the location of each sequence piece in the target sequence.

EXAMPLE 16

Sequencing and Optical Mapping Method Based on Sorting or Sorting Combined with Conversion This method makes it possible to map or sequence extra long DNA sequences, e.g. genomes, in a mapping or sequence reaction. The method can be used for optical mapping alone or for mapping plus sequencing. It is important to note that the method makes it possible to sequence many different target sequences in the same sequence reaction.

Method (Sorting Alone)
The method of Example 14 is followed but instead of step 1 the target DNA is cut with DNaseI or similar so that fragments of a few hundred bases are formed. Steps 2 to 8 are performed as described in Example 14. The scanning surfaces are then washed and the DNA molecules stretched. An optical mapping procedure or similar is then carried out. The scanning surface is scanned with a fluorescent scanner or similar and appropriate software is used to reconstruct the sequence.

Method (Sorting with Conversion)
Steps 1 to 6 are conducted as for the optical mapping method above, thereafter;
7) 256 conversion adaptors are added and ligated with the overhangs formed in step 6). The conversion adaptors may, for example, have binary signal chains in which the 1-signals are DNA sequences containing many cleavage sites for a specific restriction enzyme, while the 0-signals are DNA sequences that do not contain any such sites.
8) The converted DNA molecules from each well, is transferred to its own scanning surface and an optical mapping procedure is carried out with the restriction enzyme that has cutting sites in the 1 signals.
9) The scanning surface is scanned with a fluorescent scanner or similar and appropriate software is used to reconstruct the sequence.

EXAMPLE 17

Method for DNA Sequencing Based on Binary End Conversions and Nanopore Analysis It has been shown that an electric field can drive single-stranded RNA and DNA molecules through ion channels in a lipid membrane. The passage of the molecules can be detected as a transient decrease of ionic current. It has been shown that it is possible to discriminate between purines and pyrimidines because of their size difference. It has therefore been suggested that the method could be used for high-speed sequencing. It has however shown difficult to discriminate between different purines (Adenine or Guanine) and between different pyrimidines (Cytosine, Thymine or Uracil) because of their small size differences. In this example it is shown how this problem can be solved by converting the target DNA to a binary code consisting of purine/ pyrimidine signals.

Method

1) Fragments of the target DNA are produced by cleavage with DNase I or the like and treated to produce blunt ends.
2) The target DNA molecules are ligated with linkers containing one or more binding sites for IIS restriction enzymes (for example FokI).
3) overhangs are generated in the target DNA by cleavage with the IIS restriction enzyme.
4) The overhangs are treated with a phosphatase enzyme.
5) The overhangs are ligated with conversion adaptors. The adapters also contain direction tags to make software analysis easier.
6) The composition of purines/ pyrimidines is read with by nanopore analysis. The part of the target DNA that has not been converted may be used to obtain position information.
7) An appropriate software program is used to reconstruct the target sequence. The overhang region between the conversion adapter and target DNA can be compared with the sequence piece information as a proof-reading mechanism.

Results

The signal consists of a binary purine/pyrimidine code where A=purine+purine, C=purine+pyrimidine etc. This is illustrated in FIG. 15.

EXAMPLE 18

Use of Cells in the Generation of Signals in Sequencing Reactions

This example illustrates the use of cells both to generate signals and to themselves act as magnifying tags indicative of a particular base in a sequencing reaction.

Method

A) In this method reporter genes are used as the magnifying tags and their relative signal intensity on expression is used as an indicator of the relative position of particular bases in the sequence. The technique which is used and the results which are obtained are shown in FIG. 16.
1) A polymerase extension reaction is performed using target DNA as template and a sequencing primer that is attached to a single or double strand with an enhancer and reporter gene as illustrated in FIG. 16. The sequencing primer is used to bind to a known sequence in the target DNA indicative of the start of the sequence which will be sequenced.
2) A polymerase extension is performed with a primer mix that consists of four different primers. Each primer consists of universal (U) or random bases (N) except for the most 3' base that is either A, C, G or T. The primers are attached to four different reporter genes. Primers with an A in the most 3' position are attached to reporter gene A and so forth. The conversion primers used in this step bind the target DNA at random, except for the most 3' base which is critical for a successful polymerase extension.
3) One or more polymerase extension reactions are performed with primers that are complementary to the 5' ends of the primers used in step 1 and 2.
4) The converted DNA molecules are transformed/transfected into suitable cells.
5) The cells are grown under conditions that allow the reporter genes to be expressed.
6) The expression of the reporter genes are analyzed with a flow cytometer and suitable software is used to reconstruct the sequences.

B) In this method signals associated with different bases are directed to different locations within a cell or other structure indication of their position within a signal chain.
1) The target DNA is fragmented with DNase I or by a similar technique.
2) 16 base pairs per target DNA molecule are converted to a signal chain. 4 signals are used indicative of each of bases A, C, G or T. Each signal consists of a reporter gene A, C, G or T, linked to a promoter that will be expressed in a different location for each signal, ie. for 16 base pairs the signals are directed to 16 different locations by 16 different promoters. The location may be a cell or a group of cells in a multicellular organism. It may also be a location on a cell (e.g. a part of the outer membrane). The signal chain is transformed/transfected into the cell that gives rise to the organism/structure.
3) The cells are grown in conditions that allow the organism/structure to develop.
4) The distribution of the four different signals in each organism/structure is registered at the different locations to build up a picture of which base appears at which position along the sequence used to develop the signal chain.

Results

A) The signal intensity generated at particular locations may be examined. This is illustrated in FIG. 16. Since the signal intensity is inversely proportional to the distance between the enhancer and the reporter gene, the position of a particular signal (and hence base) relative to the start base may be established.

Ideally, to aid distinction between the different molecules which are created target nucleic acid molecules are initially sorted according to their terminal sequence such that the extension products differ by more than one base.

EXAMPLE 19

Method of Sequencing by Creating Sequencing Ladders Differing by Three Magnified Bases Each This method describes the formation of a sequencing ladder in which conversion (ie. magnification) and reading of the sequence are conducted on the same solid support. An important point with these procedures is that in addition to obtaining the base composition of short areas (6–9 bp or more, in increments of 3 bases) one also obtains information about their internal locations on larger DNA molecules (up to several kb) This is of importance to the reconstruction of the sequence information and the method can, for example, be used to complement sequence information derived through the previously mentioned alternatives. The principle is illustrated in FIG. 17 for the sequencing of a 9 base pair long polynucleotide.

Method

1) The DNA sequence that is to be sequenced is amplified by PCR. One of the primers is labelled with biotin at one end so that the DNA molecules can be fixed to a streptavidin substrate. The streptavidin is arranged in a thin line, so that the DNA molecules are fixed beside each other in a row.
2) The molecules are treated with DNase I (or similar) to generate random cuts. (step 1 of FIG. 17)

3) The cut ends are ligated to a polynucleotide that contains a binding site for a class II restriction endonuclease that cuts outside its own binding site (in this case EarI) (step 2 of FIG. 17).
4) Restriction endonuclease is then added to create an overhang in the polynucleotides (step 3 of FIG. 17).
5) Adapters are added that recognize and 1ligate specifically to the polynucleotide overhangs (step 4 of FIG. 17). Thereby, the top polynucleotide with an AGC overhang is ligated to an adapter with the AGC fragment combination etc.
6) The DNA molecules are straightened with the aid of liquid flow, an electric field or similar, so that the adapters labelled with fluorescence can be read with a fluorescence scanner.
7) The sequence is reconstructed by aligning the pieces with the sequence information.

Note that the relative position for each adapter varies according to where the polynucleotide was cut by DNaseI. In this way, each piece with sequence information can be given a relative position on the polynucleotide and this makes it easier to reconstruct the sequence.

Finally, it should be emphasized that reading several different DNA sequences on the same reading plate (FIG. 17) can increase the reading potential. For example, with the aid of PCR, one can amplify a larger number of genes with gene specific primers. Then unique overhangs are made on the amplified gene sequences. This can be done, for example, by using extra long primers in the last cycle and insert cutting sites for restriction endonucleases that cut seldom, etc. One can thereby hybridize the genes to a DNA chip where each square consists of oligonucleotides that are specific for the various genes. The DNA molecules that correspond to Gene A will thereby hybridize to Square A, Gene B to Square B, etc. This method is particularly appropriate for mass screening of the genomes of individuals when it is possible to pick out those specific areas in a genome that are of medical interest etc.

Parallel sequencing of different genes may also be achieved by amplification using gene-specific primers. Overhangs may then be generated that are specific to each gene before the genes are hybridized to the oligonucleotides on a DNA chip. The DNA chip is constructed in such a way that the oligonucleotides that are complementary to the different genes have different sites. In reality it is possible to create several thousand different addresses on the same reading plate so that it is possible to sequence several thousand genes in parallel.

A further alternative is to obtain positional information in two dimensions as illustrated in FIG. 18.
1) The starting point for the procedure is that the DNA molecules that are to be sequenced are cut into molecules of a few kb or longer. Then biotin is incorporated into the DNA molecules so that there are, on average, bases with biotin e.g. at intervals of a few hundred bases (more or fewer depending on what is required). The DNA molecules are then fixed with one end to a plate that is covered with streptavidin. The fixing mechanism for the ends should be something other than streptavidin/biotin.
2) The molecules are straightened with the aid of a liquid flow, an electric field or other means. The DNA molecules are anchored to the substrate by adding a reaction solution that creates a biotin-streptavidin binding.
3) The DNA molecules are then cut with DNaseI or other means before the free ends are ligated to the preadapters that contain binding sites for type IIS restriction endonucleases (not shown). By then cutting with the respective endonuclease, overhangs are produced that are ligated to adapters with sequence information.
4) An adapter with a fragment combination of ACGT is then ligated to the ACGT overhang, etc.
5) A liquid flow, electric field or a similar process is used to straighten the DNA adapters in a 90 degree direction to the direction of the DNA molecule that is to be sequenced, before they are anchored with the biotin/streptavidin system. When all the DNA molecules have been anchored to the substrate, the process can be repeated until the desired number of base pairs has been converted/magnified. Also note that the relative distances between the adapters correspond to the internal distances of the sequence pieces in the DNA molecule that is to be sequenced. It should also be mentioned that it is of course possible to sequence very many DNA molecules in parallel on one reading plate.

EXAMPLE 20

Method of Sequencing Using Adapters With Linkers to Space the Magnified Portions Away From the Target Molecule The method described below illustrates one technique in which more than one cycle of sequencing may be achieved. In this method, magnifying tags which are created are attached to a solid support. A linker spacing the tags from the sequence to which they correspond is subsequently removed and an adjacent portion of the target sequence may then be magnified. The procedure is shown in FIG. 19.

Method
1) The DNA molecule that is to be sequenced, ACGT-GAGCT (SEQ ID NO:15) is fixed with one end to a streptavidin-covered plate. The fixing mechanism should be a mechanism other than streptavidin/biotin.
2) The DNA molecule is ligated to a polynucleotide that contains a binding site for a type II restriction endonuclease with a cutting site outside of the binding site (e.g. BspMI as shown in FIG. 19).
3) In the next step the restriction endonuclease is added and cleavage forms an overhang with base from the DNA molecule that is be sequenced.
4) A solution with various adapters and ligases is then added. FIG. 19 shows an adapter that has recognized and bound to the ACGT (SEQ ID NO:16) overhang. In addition to fragments labelled with fluorescence that correspond to the ACGT (SEQ ID NO:16) overhang, two or more biotin molecules have been on the adapter.
5) The DNA molecule is straightened out with the aid of a liquid flow or an electric field, and the fragments may be fixed to the substrate as shown. (The function of the DNA linker region is to space the fragments away from the DNA molecule that is being sequenced. This leaves room for a new adapter in the next step.)
6) Cleavage is performed with SmaI and BspMI so that the DNA link is removed at the same time as a new overhang is formed consisting of the next four base pairs on the DNA molecule. This makes it possible to ligate a new adapter with fluorescence labelled fragments. The only difference is that this adapter does not contain a DNA link. The fluorescence labelled adapter will then be fixed to a new position on the streptavidin substrate. By using DNA links of different lengths, it is possible to perform multiple consecutive conversion cycles.

EXAMPLE 21

Use of Position Markers in Sequencing Methods

In this method position markers are associated with the molecule to be sequenced to assist positioning of the sequence information which is obtained.

Method

The method which is used is illustrated in FIG. 20. The starting point is a circular target DNA molecule of eg, 100 kb. The molecule contains two sequences marked with light and dark grey (in FIG. 20), that will be used as position markers.
1) The DNA molecules are methylated with Bst71I methylase.
2) The molecules are linearised with DNaseI or similar, after which an adaptor containing cleavage sites for Bst71I is added by ligation. (The cutting sites are placed so they can be used to make an overhang with the first four bases in the target DNA molecule. The two 4 bp overhangs will thereby be able to provide information on a continuous sequence on 8 bp.)
3) Cleavage is performed with Bst71I and the fragment adaptors are added and ligated.
4) The DNA molecules are converted to single-strand form before being anchored and stretched on a slide by means of molecular combing, an electric field or similar, at the same time as hybridising with fluorescent probes that recognize the fragments and position markers. It may also be relevant to colour the DNA molecules with YOYO-1 or similar.
5) The sequence pieces are then scanned using a fluorescent microscope/scanner and the distance to the probes that have attached to the position markers is then measured. This allows an approximate position to be assigned to each sequence piece of 8 bp on the DNA molecule to be sequenced.

EXAMPLE 22

Method of Sequencing Involving Sorting Followed by Magnification

In this method fragments are sorted on a solid support by virtue of their terminal 4 bases after which the end terminal of the molecule is attached to the solid support. The adjacent 4 bases may then be assessed by magnification. An example of this method is shown in FIG. 21.

Method

A DNA chip is used which is divided into 256 addresses. Each address contains sorting adaptors, an overhang, a binding site for a class IIS restriction endonuclease and a binding site for a restriction endonuclease that makes a blunt end cut. The overhangs vary from address to address so that address 1 has sorting adaptors with an AAAA (SEQ ID NO:1) overhang, address 2 has an AAAC (SEQ ID NO:8) overhang, etc. In addition all the addresses are covered with a molecule with binding properties, e.g. streptavidin.
1) The sorting starts by cutting the target DNA into pieces and treating the ends of the DNA pieces to form a 4-base overhang.
2) The fragments are introduced to the solid support carrying the sorting adaptors to which they are ligated. DNA pieces with a TTTT (SEQ ID NO:2) overhang will ligate to address 1 in which the sorting adaptors have the complementary overhang AAAA (SEQ ID NO:1), DNA pieces with a GTTT (SEQ ID NO:10) overhang will ligate to address 2 etc.
3) The other overhang on the DNA piece is treated so that the end can be anchored to the underlay. For example this may be achieved by a Klenow fill-in reaction to label the end with biotin, ligate the ends with biotin-labelled universal adaptors etc.
4) Cleavage with IIS and blunt end enzyme is performed (in this case illustrated with FokI and DraI). In this way a new overhang is obtained in the DNA piece that represents the next four bases.
5) Conversion adaptors are added to convert these bases into a signal chain.
6) The DNA molecules are stretched and scanned using e.g. a fluorescent scanner. The position of one end of the DNA molecule provides us with information about four bases, and the signal chain at the other end provides information about the next four.

EXAMPLE 23

Method for Preparing Target Molecules for Mapping Procedures, Profile Analysis and the Like The principle behind this protocol is to digest the target DNA with one or several nucleases that, preferentially, make cuts outside its own recognition sequence, for example IIS enzymes, but other kinds of nucleases may also be used., e.g. to generate overhangs ranging from −5 to +5. The overhangs are then ligated with signal chains consisting of one part containing sequence information and one part containing information about the nature of the overhang (i.e. which restriction enzyme that has made the overhang). Each of the digested molecules are thereby converted into signatures differing by the signal compositions at their ends and the length between the ends. By aligning ends with complementary sequences (e.g. alignment of one or more of the magnifying tags associated with the complementary overhangs created on digestion) it is possible to use the information to make a restriction map. The signatures may also be used to identify target sequences in a heterogeneous DNA population. The principle using FokI is shown in FIG. 22.

If we want to map FokI sites in a target DNA that is a 100 kb BAC clone dissolved in water we can use the following protocol:
1) Add 1 unit of FokI (New England Biolabs #109), 2.5 $\mu$l 10×NE Buffer 4, 1 $\mu$g BAC DNA and water to a final volume of 25 $\mu$l.
2) Incubate at 37° C. for 1 h.
3) Heat inactivation at 65° C. for 20 min.
4) Precipitate the DNA with EtOH.
5) Dissolve the pellet in water and add Phosphatase treated conversion adapters (the molar ratio between the conversion adapters and target DNA should be at least 50:1) 200 units T4 DNA ligase (New England Biolabs #202), 2.5 $\mu$l 10×T4 DNA ligase reaction buffer. Final volume: 25 $\mu$l.
6) Incubate at 16° C. for 4–16 h.

It is now possible to perform the analysis. It may however be preferable to perform a procedure to remove unligated adapters. For example;
7) Add 1.5–2×10$^8$ Dynabeads M-280 Streptavidin (Dynal #112.05 or #112.06) coated with adapters containing all permutations with 5', 4 bases overhangs, 2000 units T4 DNA ligase (New England Biolabs #202), 22.5 $\mu$l 10×T4 DNA ligase reaction buffer and water to a final volume of 250 $\mu$l.
8) Incubate at 16° C. for 4–16 h.
9) Precipitate the beads with a magnet as explained in "Biomagnetic Techniques in Molecular Biology", 3rd edition (distributed by Dynal AS, Norway) and remove the supernatant.
10) Precipitate the DNA molecules in the supernatant with EtOH.
11) Dissolve the DNA molecules in an appropriate solution and volume.

The conversion adapters used in this protocol may represent all 256 permutations of overhangs, only a subset of the 256 overhangs or overhangs with one or more degenerate bases. If the molecules are going to be analysed with an optical mapping strategy the signals may for example consist of 0-signals that are free of EcoRI sites and 1-signals containing a huge number of EcoRI sites.

The above procedure may also be repeated one or more times with other sets of restriction enzymes and signal chains before the molecules are analysed. It must however, be pointed out that the signal chains ligated with the overhangs generated in the first round must be protected from digestion of the enzymes used in the second round. This may be accomplished by using signal chains free of binding sites for the restriction enzymes used in the second round, methylating the sites, etc.

The procedure may also be performed in connection with a sorting procedure or other procedures that increase the sequence-length obtained in each end.

Restriction site positions within a target sequence may be determined by determining which restriction sites flank a particular restriction site partly by identifying the restriction site that is present at the other end of the resultant fragments of target DNA and partly by identifying other target fragments containing a complementary overhang and the restriction sites to which these fragments are linked. It is not necessary to determine the length of each fragment since the position can be determined quite precisely by the use of sufficient restriction enzymes.

This method has several important, advantageous features compared with conventional methods for optical mapping:
1) The resolution is much better: It is possible to distinguish between restriction sites separated by only a few base pairs while conventional techniques require at least a few hundred base pairs.
2) It is easier to make restriction maps with multiple restriction enzymes.
3) The statistical problems with the reconstruction is greatly reduced since the alignments are based upon the composition of signal-chains rather than uncertain measurements of DNA lengths between restriction sites that are only partially cut.
4) When enzymes which cleave outside their recognition site are used, each location in the map is based upon the length of the binding site plus the length of the overhang (usually 9 or more bases). Thus a restriction site may be identified on the basis of both the sequence of the binding site and the overhang it creates. This is advantageous compared with conventional genomic maps made with rare cleavage enzymes (8 bases).

---

What is claimed is:

1. A method of magnifying a signal associated with one or more nucleotide bases of a nucleotide sequence in a target nucleic acid molecule comprising the steps of:
- (A) treating said target nucleic acid molecule so that at least a region of said target nucleic acid molecule is converted into an adapter binding region which is a region suitable for binding an adapter molecule;
- wherein said adapter molecule comprises:
  - (i) one or more magnifying tags, or
  - (ii) a means for attaching one or more of said magnifying tags to said adapter binding region,
  - wherein said magnifying tag(s) correspond to: (a) one or more nucleotide bases of the adapter binding region or (b) one or more nucleotide bases adjacent to the adapter binding region or (c) one or more nucleotide bases which overlap the adapter binding region;
- (B) binding said adapter molecule to at least a portion of said adapter binding region created in step (A) to form a nucleic acid molecule:adapter molecule complex;
- (C) optionally, ligating said target nucleic acid molecule to said adapter molecule such that at least said magnifying tag(s) remain associated with said target nucleic acid molecule and to form a ligated nucleic acid molecule:adapter molecule complex;
- (D) treating the resulting complex of step (B) or the resulting complex of step (C) so that at least another region of said target nucleic acid molecule is converted into a form suitable for binding another adapter molecule, wherein said another region comprises one or more nucleotide bases which are not associated with the magnifying tags of step (B); and thereafter
- (E) repeating steps (B) to (D), with the proviso that the adapter molecule in each cycle of steps (B) to (C) binds to a region adjacent to a region of said target nucleic acid molecule to which the adapter molecule of a previous cycle bound, or the adapter molecule in each cycle of steps (B) to (C) binds to a region which overlaps with a region of said target nucleic acid molecule to which the adapter molecule of a previous cycle bound, and wherein the magnifying tags of each cycle of steps (A) to (C) are ligated together, to thereby magnify said signal.

2. The method as claimed in claim 1, wherein in step (A), said form is a single-stranded nucleic acid molecule.

3. The method as claimed in claim 1, wherein said magnifying tag(s) correspond to one or more nucleotide bases of said adapter binding region.

4. The method as claimed in claim 1, wherein each magnifying tag corresponds to at least 2 nucleotide bases in said adapter binding region or to at least 2 nucleotide bases adjacent to said adapter binding region.

5. The method as claimed in claim 1, wherein said magnifying tags together correspond to at least 2 nucleotide bases in said adapter binding region or to at least 2 nucleotide bases adjacent to said adapter binding region.

6. The method as claimed in claim 5, wherein said magnifying tags together correspond to at least 4 nucleotide bases in said adapter binding region or to at least 4 nucleotide bases adjacent to said adapter binding region.

7. The method as claimed in claim 1, wherein a chain of magnifying tags are associated with said target nucleic acid molecule.

8. The method as claimed in claim 7, wherein said chain comprises 4 or more magnifying tags corresponding to at least 4 contiguous nucleotide bases.

9. The method as claimed in claim 1, wherein said magnifying tags are nucleic acid sequences of at least 2 nucleotide bases in length.

10. The method as claimed in claim 9, wherein said magnifying tags are nucleic acid sequences of 10 to 30 nucleotide bases in length.

11. The method as claimed in claim 1, wherein said adapter molecule comprises a recognition site for a nuclease, which has a cleavage site separate from its recognition site.

12. The method as claimed in claim 1, wherein said adapter molecule comprises recognition sites for 2 or more nucleases, which have cleavage sites separate from their respective recognition sites, wherein cleavage with said nucleases produces single-stranded regions which are adjacent or overlapping.

13. The method as claimed in claim 1, wherein two or more adapter molecules are bound in step (B).

14. The method as claimed in claim 13, wherein said adapter molecules are bound to overlapping or adjacent regions.

15. The method as claimed in claim 14, wherein said adapter molecules are bound to overlapping regions thereby allowing the association of more than one magnifying tag with each nucleotide base.

16. The method as claimed in claim 1, wherein step (C) is performed.

17. The method as claimed in claim 1, further comprising the step of:
- (F) sequencing the target nucleic acid molecule by identifying the magnifying tags associated with the target nucleic acid molecule.

18. The method as claimed in claim 17, wherein 2 or more nucleotide bases are sequenced per cycle.

19. The method as claimed in claim 18, wherein 4 or more nucleotide bases are sequenced per cycle.

20. The method as claimed in claim 17, wherein the signal associated with each nucleotide base is magnified by increasing the number of times that said nucleotide base appears in said sequence.

21. The method as claimed in claim 17, wherein the resulting magnified signal is converted into readable signals and said sequencing is carried out by assessing the readable signals.

22. The method as claimed in claim 17, wherein each readable signal comprises a pattern made up of a single signal event which creates a unique signal on each magnifying tag.

23. The method as claimed in claim 1, wherein said method is performed on a sample comprising a heterogeneous mixture of target nucleic acid molecules.

24. The method as claimed in claim 17, wherein said method is performed on a sample comprising a heterogeneous mixture of target nucleic acid molecules.

* * * * *

SEQUENCE LISTING

```
<160> NUMBER OF SEQ ID NOS: 17

<210> SEQ ID NO 1
<211> LENGTH: 4
<212> TYPE: DNA
<213> ORGANISM: synthetic construct

<400> SEQUENCE: 1 aaaa                                                                    4

<210> SEQ ID NO 2
<211> LENGTH: 4
<212> TYPE: DNA
<213> ORGANISM: synthetic construct

<400> SEQUENCE: 2 tttt                                                                    4

<210> SEQ ID NO 3
<211> LENGTH: 5
<212> TYPE: DNA
<213> ORGANISM: synthetic construct

<400> SEQUENCE: 3 acgtt                                                                   5

<210> SEQ ID NO 4
<211> LENGTH: 4
<212> TYPE: DNA
<213> ORGANISM: synthetic construct
<220> FEATURE:
<221> NAME/KEY: Unsure
<222> LOCATION: (2)..(4)
<223> OTHER INFORMATION: n at positions 2, 3 and 4 is a or g or c or t

<400> SEQUENCE: 4 annn                                                                    4
```

-continued

```
<210> SEQ ID NO 5
<211> LENGTH: 4
<212> TYPE: DNA
<213> ORGANISM: synthetic construct
<220> FEATURE:
<221> NAME/KEY: unsure
<222> LOCATION: (2)..(4)
<223> OTHER INFORMATION: n at position 2, 3 and 4 is a or g or c or t

<400> SEQUENCE: 5 tnnn                                                              4

<210> SEQ ID NO 6
<211> LENGTH: 4
<212> TYPE: DNA
<213> ORGANISM: synthetic construct
<220> FEATURE:
<221> NAME/KEY: unsure
<222> LOCATION: (2)..(4)
<223> OTHER INFORMATION: n at positions 2, 3 and 4 is a or g or c or t

<400> SEQUENCE: 6 cnnn                                                              4

<210> SEQ ID NO 7
<211> LENGTH: 4
<212> TYPE: DNA
<213> ORGANISM: synthetic construct
<220> FEATURE:
<221> NAME/KEY: unsure
<222> LOCATION: (2)..(4)
<223> OTHER INFORMATION: n at positions 2, 3 and 4 is a or g or c or t

<400> SEQUENCE: 7 gnnn                                                              4

<210> SEQ ID NO 8
<211> LENGTH: 4
<212> TYPE: DNA
<213> ORGANISM: synthetic construct

<400> SEQUENCE: 8 aaac                                                              4

<210> SEQ ID NO 9
<211> LENGTH: 4
<212> TYPE: DNA
<213> ORGANISM: synthetic construct

<400> SEQUENCE: 9 tttg                                                              4

<210> SEQ ID NO 10
<211> LENGTH: 4
<212> TYPE: DNA
<213> ORGANISM: synthetic construct

<400> SEQUENCE: 10 gttt                                                              4

<210> SEQ ID NO 11
<211> LENGTH: 64
<212> TYPE: DNA
<213> ORGANISM: synthetic construct
<220> FEATURE:
<221> NAME/KEY: unsure
```

```
<222> LOCATION: (8)..(30)
<223> OTHER INFORMATION: n at positions 8-30 is a or g or c or t
<221> NAME/KEY: unsure
<222> LOCATION: (39)..(60)
<223> OTHER INFORMATION: n at positions 36-60 is a or g or c or t

<400> SEQUENCE: 11
agctgtgann nnnnnnnnnn nnnnnnnnnn agtctgcann nnnnnnnnnn nnnnnnnnnn      60
tgac                                                                  64

<210> SEQ ID NO 12
<211> LENGTH: 8
<212> TYPE: DNA
<213> ORGANISM: synthetic construct

<400> SEQUENCE: 12 aaaaaaaa                                                               8

<210> SEQ ID NO 13
<211> LENGTH: 8
<212> TYPE: DNA
<213> ORGANISM: synthetic construct

<400> SEQUENCE: 13 aaaaaaac                                                               8

<210> SEQ ID NO 14
<211> LENGTH: 8
<212> TYPE: DNA
<213> ORGANISM: synthetic construct

<400> SEQUENCE: 14 tttttttt                                                               8

<210> SEQ ID NO 15
<211> LENGTH: 9
<212> TYPE: DNA
<213> ORGANISM: synthetic construct

<400> SEQUENCE: 15 acgtgagct                                                              9

<210> SEQ ID NO 16
<211> LENGTH: 4
<212> TYPE: DNA
<213> ORGANISM: synthetic construct

<400> SEQUENCE: 16 acgt                                                                   4

<210> SEQ ID NO 17
<211> LENGTH: 4
<212> TYPE: DNA
<213> ORGANISM: synthetic construct

<400> SEQUENCE: 17 atgc                                                                   4
```